United States Patent
Li et al.

(10) Patent No.: US 10,415,053 B2
(45) Date of Patent: Sep. 17, 2019

(54) MATERIALS AND METHOD FOR INCREASING A PLANT'S RESISTANCE TO STRESS

(71) Applicant: IOWA STATE UNIVERSITY RESEARCH FOUNDATION, INC., Ames, IA (US)

(72) Inventors: Ling Li, Ames, IA (US); Eve Syrkin Wurtele, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 35 days.

(21) Appl. No.: 14/918,525

(22) Filed: Oct. 20, 2015

(65) Prior Publication Data
US 2016/0083745 A1 Mar. 24, 2016

Related U.S. Application Data

(60) Continuation-in-part of application No. 14/852,594, filed on Sep. 13, 2015, which is a division of application No. 13/314,139, filed on Dec. 7, 2011, now Pat. No. 9,157,091.

(60) Provisional application No. 61/446,460, filed on Feb. 24, 2011.

(51) Int. Cl.
C12N 15/82 (2006.01)
C07K 14/415 (2006.01)
A01H 5/10 (2018.01)

(52) U.S. Cl.
CPC ........... *C12N 15/8279* (2013.01); *A01H 5/10* (2013.01); *C07K 14/415* (2013.01); *C12N 15/8245* (2013.01); *C12N 15/8247* (2013.01); *C12N 15/8251* (2013.01); *C12N 15/8281* (2013.01); *C12N 15/8283* (2013.01); *C12N 2710/00043* (2013.01); *C12N 2830/008* (2013.01)

(58) Field of Classification Search
None
See application file for complete search history.

(56) References Cited

U.S. PATENT DOCUMENTS

| 5,792,920 A * | 8/1998 | Bridges | C07K 16/40 435/101 |
| 6,162,965 A * | 12/2000 | Hansen | C07K 14/195 435/252.2 |
| 2008/0113342 A1 | 5/2008 | Cao et al. | |
| 2008/0184386 A1 | 7/2008 | Cao et al. | |

OTHER PUBLICATIONS

* Li et al. (Plant Journal, 58:485-498; 2009).*
* Lin et al. (Planta, 225:153-164; 2006).*
* Li et al. (Metabolic Engineering, 12:387-391; 2010).*
* Comai et al. (Plant Molecular Biology, 15:373-381; 1990).*
* Müller-Röber et al. (EMBO Journal, 11:1229-1238; 1992).*
Zhang et al. (Molecular Plant; 1(3):510-527; May 2008) (Year: 2008).*
Li et al. (Plant Journal, 58:485-498; 2009) (Year: 2009).*
Li et al., (Plant Biotechnology J., 13(2):177-187, 2015) (Year: 2015).*
Doerks et al., (TIG,14:248-250, 1998) (Year: 1998).*
Smith et al. (Nature Biotechnology, 15:1222-1223, 1997) (Year: 1997).*
Bork et al. (TIG, 12:425-427, 1996) (Year: 1996).*
Stein et al. (Plant Cell, 731-746; 2006).*
Salanoubat et al. (GenBank Sequence Accession No. NP_001326492.1; Published Sep. 12, 2016).*
Comai et al., "Novel and useful properties of a chimeric plant promoter combining CaMV 35S and MAS elements," *Plant Molecular Biology*, 15: 373-381 (1990).
Li et al., "Chlamydomonas starch less mutant defective in ADP-glucose pyrophosphorylase hyper-accumulates triacylglycerol," *Metabolic Engineering*, 12: 387-391 (2010).
Li et al., "Identification of the novel protein QQS as a component of the starch metabolic network in *Arabidopsis* leaves," *Plant Journal*, 58(3): 485-498 (2009).
Li et al., "Uncovering Novel Signalling Interactions in Regulation of Plant Metabolic Networks," *Plant Biology*, Retrieved from the Internet: http://abstracts.aspb.org/pb2011/public/P14/P14009.html (2011).
Lin et al., "Genetic and transgenic perturbations of carbon reserve production in *Arabidopsis* seeds reveal metabolic interactions of biochemical pathways," *Planta*, 225: 153-164 (2006).
Muller-Rober et al., "Inhibition of the ADP-glucose pyrophosphorylase in transgenic potatoes leads to sugar-storing tubers and influences tuber formation and expression of tuber storage protein genes," *EMBO Journal*, 11: 1229-1238 (1992).
Seo et al., "Two splice variants of the IDD14 transcription factor competitively from nonfunctional heterodimers which may regulate starch metabolism," *Nature Comm.*, 2: 3-4 (2011).
Seo et al., "Two splice variants of the IDD14 transcription factor competitively from nonfunctional heterodimers which may regulate starch metabolism," *Nature Comm.*, 2:303, DOI: 10.1038 (2011).
Tanaka, "Flower Colour and cytochromes P450," *Phytochem Rev.*, 5: 283-291 (2006).
Wurtele et al., "ISURF Case #3844: High Protein Low Starch QQS Soybeans for Enhanced Value," *Iowa State Univ. Sci. & Tech.*, retrieved from the Internet: www.techtransfer.iastate.edu/documents/630141298651778854.pdf (2012).

(Continued)

*Primary Examiner* — Vinod Kumar
(74) *Attorney, Agent, or Firm* — Carol Larcher; Larcher & Chao Law Group

(57) ABSTRACT

Method of increasing resistance to a pathogen or a pest in a plant comprising introducing into the plant and expressing therein a polynucleotide comprising a nucleotide sequence encoding a Qua-Quine Starch (QQS) polypeptide; method of producing a plant with increased resistance to a pathogen or a pest comprising crossing a plant obtained in accordance with the above method with a second plant to produce progeny plants and selecting progeny plants with increased resistance to a pathogen or a pest; a plant with increased resistance to a pathogen or a pest; a seed of the plant; a hybrid of the plant; and a seed of the hybrid plant.

18 Claims, 6 Drawing Sheets

Specification includes a Sequence Listing.

(56) References Cited

OTHER PUBLICATIONS

Wurtele et al., "Starch-controlling gene fuels more protein in soybean plants," *Iowa State Univ. News Service,* retrieved from the Internet: www.news.iastate.edu/news/2011/apr/wurtele (2012).
Search Report & Written Opinion issued in Int'l App. No. PCT/US2011/063850 (2012).

* cited by examiner

```
  1 ctcagaagaa gcctcctttc gatctgtcag ccattgaaga aacctccttt cgatctgtca
 61 gccattgaag atcagaagaa acaagactca cacggtcagc cattgaagaa gcctcctctc
121 attacctctc atcaaacatc tagatctgta cccaaacctt atccctttt ccttatttct
181 cgctttgtct attcttaatc tgattaatac ttgttgttgt tccaggttat agaagatctg
241 ggttgtgtta tatgcttcat tttctccaca gcgaccagtt ggtgtttggt tcttagattc
301 atgaagacca atagagagca ggaaatttac gttgaaagaa gcttcaaacc aaacaattca
361 acaattcaga atttgatgga cattgaaagg ttcattttgc ctcacacttc tacatcaggt
421 gtcgcaaggc tcaaaatgag ggtcatatca tgggtcgggc ttcagttcta caactactga
481 tattgggcct tatcacaaat tagttatagg gccattgtat ccaatattta atatctctgt
541 aaacttgttt aatggttatt ttgttctaat gcccattaca actaga [SEQ ID NO: 1]
```

FIG. 1a

MKTNREQEIYVERSFKPNNSTIQNLMDIERFILPHTSTSGVARLKMRVISWVGLQFYNY [SEQ ID NO: 2]

FIG. 1b

SEQUENCE LISTING

```
<160> NUMBER OF SEQ ID NOS: 4

<210> SEQ ID NO 1
<211> LENGTH: 586
<212> TYPE: DNA
<213> ORGANISM: Arabidopsis thaliana QQS

<400> SEQUENCE: 1
ctcagaagaa gcctcctttc gatctgtcag ccattgaaga aacctccttt cgatctgtca    60
gccattgaag atcagaagaa acaagactca cacggtcagc cattgaagaa gcctcctctc   120
attacctctc atcaaacatc tagatctgta cccaaacctt atccctttt ccttatttct    180 cgctttgtct attcttaatc tgattaatac ttgttgttgt tccaggttat agaagatctg   240
ggttgtgtta tatgcttcat tttctccaca gcgaccagtt ggtgtttggt tcttagattc   300
atgaagacca atagagagca ggaaatttac gttgaaagaa gcttcaaacc aaacaattca   360
acaattcaga atttgatgga cattgaaagg ttcattttgc ctcacacttc tacatcaggt   420
gtcgcaaggc tcaaaatgag ggtcatatca tgggtcgggc ttcagttcta caactactga   480
tattgggcct tatcacaaat tagttatagg gccattgtat ccaatattta atatctctgt   540
aaacttgttt aatggttatt ttgttctaat gcccattaca actaga              586

<210> SEQ ID NO 2
<211> LENGTH: 59
<212> TYPE: PRT
<213> ORGANISM: Arabidopsis thaliana QQS

<400> SEQUENCE: 2

Met Lys Thr Asn Arg Glu Gln Glu Ile Tyr Val Glu Arg Ser Phe Lys
1               5                   10                  15

Pro Asn Asn Ser Thr Ile Gln Asn Leu Met Asp Ile Glu Arg Phe Ile
            20                  25                  30
```

```
Leu Pro His Thr Ser Thr Ser Gly Val Ala Arg Leu Lys Met Arg Val
        35                  40                  45

Ile Ser Trp Val Gly Leu Gln Phe Tyr Asn Tyr
    50                  55

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
cctcccaggc atggcagtcc                                             20

<210> SEQ ID NO 4
<211> LENGTH: 18
<212> TYPE: DNA
<213> ORGANISM: Artificial
<220> FEATURE:
<223> OTHER INFORMATION: Synthetic

<400> SEQUENCE: 4
ccatcaaggc tccgctgg                                               18
```

MATERIALS AND METHOD FOR INCREASING A PLANT'S RESISTANCE TO STRESS

CROSS REFERENCE TO RELATED APPLICATIONS

This application is a continuation-in-part of co-pending patent application Ser. No. 14/852,594 filed Sep. 13, 2015, as a divisional of U.S. Pat. No. 9,157,091, which issued Oct. 13, 2015, and claims priority to U.S. provisional application No. 61/446,460, filed Feb. 24, 2011, the contents of all of which are incorporated herein by reference in their entireties.

STATEMENT REGARDING FEDERALLY SPONSORED RESEARCH OR DEVELOPMENT

The invention disclosed herein was made with support from the Government of the United States of America under Grant Nos. MCB0209789 and MCB0951170 awarded by the National Science Foundation. The Government of the United States of America has certain rights in the invention.

TECHNICAL FIELD

This disclosure relates to materials and a method for increasing a plant's resistance to stress, such as abiotic (e.g., salt, drought, pollution) or biotic (e.g., pathogens and pests) stress. This disclosure also relates to the expression of Qua-Quine Starch (QQS) in a plant, which is at risk for infection with a pathogen or a pest and the wild-type of which does not otherwise express QQS, and the selection of transgenic plants with increased resistance to the pathogen or the pest, as well as tissue culture, crossing and backcrossing plants, regenerable cells, and seeds.

BACKGROUND

The qua-quine starch (QQS) gene (locus ID At3g30720; GenBank Accession Nos. EU805808.1 and NM_113075.4) has been found to have an effect on plant biochemical components in *Arabidopsis*. The QQS gene encodes a protein that contains 59 amino acids, has no known function, has no sequence similarity to other proteins in *Arabidopsis* or other organisms, has no known catalytic motifs, and no known structural motifs. Analysis of the QQS promoter indicates that it has a CCA1 binding site motif (AAAAATCT) at position −734, a TGA1 binding site motif (TGACGTGG; bZip transcription factor function) at position −504, an UPRMOTIFIAT motif (TGACGTGG; unfold protein response) at position −504, an ABRE-like binding site motif (GACGTGGC; ABA function) at position −503, and an ACGTABREMPTIFA2OSEM motif (ACGTGGC; ABA function) at position −502. QQS RNA transcripts increase during pollen development (from uninucleate microspores to bicellular pollen to tricellular pollen to mature pollen) in WT (WT) *Arabidopsis*, reaching peak levels in mature pollen. In wild type (WT) *Arabidopsis*, activity of the QQS promoter as determined using the β-glucuronidase (GUS) gene reporter system is evident at 2 days after imbibition (DAI) in hypocotyls and root tips. As seedlings grow, QQS expression expands to the vasculature, mesophyll cells, hyadothodes, and trichomes of leaf blades and petioles. Microscopic dissection indicates no expression is detected in shoot meristem; the dark GUS staining in the shoot tip is associated with the adjacent vasculature. GUS activity is higher in mature leaves compared to young emerging leaves; it consistently appears somewhat unevenly distributed, and is predominantly located in the vasculature; this pattern is maintained throughout development. QQS expression is low in flower buds; however, by flower opening QQS expression is evident in pedicels, sepals, filaments, mature pollen, stigma papillae and styles, but not in petals. During silique development, QQS expression rises in the stigma papillae and style, and becomes apparent throughout the maternal tissues of the silique wall and receptacle. QQS is expressed in roots throughout development. Expression is highest in the root tip, specifically the root cap, columella cells and peripheral cap, and to a lesser extent in the root meristem region, but not in the epidermis. QQS is expressed at the site of lateral root initiation, and in the root tip and vasculature during its emergence; as the lateral root matures, expression remains detectable throughout the root cortex vasculature. GUS activity driven by the QQS promoter was higher in the Atss3 (starch synthase 3) single mutant than in WT under virtually all conditions. Expression was detectable throughout the entire seedling at 2 DAI, as well as later in development, in particular in leaves, flowers and roots. Although the general pattern of expression is similar in the Atss3 mutant and WT, QQS is expressed ectopically in petals in the Atss3 mutant. QQS RNA accumulates neither in the nucleus nor in the plastids. Expression of QQS promoter-GUS in the Atss2/Atss3 double-mutant background was more nuanced, but was in general similar to or somewhat lower than that in WT throughout leaf development. QQS transcripts increased seven-fold during the diurnal cycle in the Atss3 mutant compared to WT *Arabidopsis*; QQS protein levels also increased in the Atss3 mutant compared to WT *Arabidopsis*. Analysis of QQS RNAi (interfering RNA) mutants showed that starch content increased 20-30% at the end of the light cycle (about the same increase as observed in Atss3 mutants) due to increased starch biosynthesis and not decreased starch degradation; there was no difference in starch content at the end of the dark cycle. Starch content decreased to WT level within four hours of the dark cycle. All of the above examples are described in Li et al., Plant Journal 58: 485-498 (2009).

QQS expression has been observed to be tightly linked with a variety of developmental, environmental, and genetic perturbations (see, e.g., Arendsee et al., Trends in Plant Sci doi:10.1016/j.tplants.2014.07.003 (2014); Li et al. (2009), supra; and Li et al., Plant Biotech J: 13(2): 177-187 (2015)). Its role, however, in such perturbations has not been elucidated. For example, PEN3 (Penetration Resistance 3 (At1g59870, PEN3, ABC binding cassette transporter gene) confers non-host resistance to fungal and oomycete pathogens. QQS has been reported to be the only gene that is up-regulated in pen3 knock-out (KO) mutants; however, QQS is up-regulated in infected and non-infected mutants (Stein et al., Plant Cell 18(3): 731-746 (2006)). As another example, two syntaxins, namely SYP121 (At3g11820, PEN1) and SYP122 (At3g52400) confer resistance to powdery mildews. Knock-outs of these genes result in increased sensitivity to these pathogens; QQS has been reported to be the only gene that is up-regulated in both (Zhang et al. (2008)). In contrast, while PEN3 and EXL1 are up-regulated following exposure to some pathogens, QQS is down-regulated in response to infection by some pathogens, such as *Pseudomonas syringae* (Kwon et al., Planta 236(3): 887-900 (2012); and Thilmony et al., Plant J. 46(1): 34-53 (2006)). When *Arabidopsis* plants were inoculated with *Phytopthera infestans*, QQS reportedly was first down-regulated at 6 hrs post-inoculation and then up-regulated at 12 and 24 hrs post-inoculation (Scheel et al., Experiment ID "E-GEOD-5616" in ArrayExpress).

In view of the foregoing, it is an object of the present disclosure to provide materials and a method for increasing a plant's resistance to a pathogen or a pest. More specifically, it is an object of the present disclosure to express Qua-Quine Starch (QQS) in a plant, which is at risk for infection with a pathogen or a pest and the wild-type of which does not otherwise express QQS, and selecting transgenic plants with increased resistance to the pathogen or the pest. This and other objects and advantages, as well as inventive features, will become apparent from the detailed description provided herein.

SUMMARY

A method of increasing resistance to a pathogen or a pest in a plant is provided. The method comprises introducing into the plant, the wild-type of which does not express Qua-Quine Starch (QQS), and expressing therein a polynucleotide comprising a nucleotide sequence encoding a QQS polypeptide having the amino acid sequence as set forth in SEQ ID NO: 2, wherein the nucleotide sequence is operably linked to a promoter. In an embodiment, the method comprises (a) transforming plant cells with a polynucleotide comprising a nucleotide sequence encoding a QQS polypeptide having the amino acid sequence as set forth in SEQ ID NO: 2, and wherein the nucleotide sequence is operably linked to a promoter; (b) regenerating transgenic plants from the transformed plant cells; and (c) identifying and selecting a transformed plant from the transgenic plants which exhibits increased resistance to a pathogen or a pest as compared to an untransformed plant of the same species lacking the QQS polypeptide and grown under similar conditions, wherein the increased resistance to a pathogen or a pest is due to the expression of the QQS polypeptide in the selected transformed plant. The promoter can be constitutive, inducible, developmentally specific, synthetic or hybrid. The constitutive promoter can be a cauliflower mosaic virus 35S promoter. The developmentally specific promoter can be a seed-specific promoter. The pathogen can be a bacterium, a virus, a fungus, or a seed plant. The pest can be an insect (such as an aphid), a plasmodiophorid, a mite, or a nematode. The plant can be a crop plant, such as soybean. The plant can be a monocot or a dicot.

Another method of producing a plant with increased resistance to a pathogen or a pest is provided. The method comprises crossing a plant obtained in accordance with the above method with a second plant to produce progeny plants and selecting progeny plants with increased resistance to a pathogen or a pest.

In view of the above methods, a plant, the wild-type of which does not comprise and express QQS and into which a polynucleotide comprising a nucleotide sequence encoding a QQS polypeptide having the amino acid sequence as set forth in SEQ ID NO: 2 has been introduced and expressed therein, is provided. The nucleotide sequence is operably linked to a promoter. The plant has increased resistance to a pathogen or a pest. Also provided is a seed of the plant, a hybrid of the plant, and a seed of the hybrid.

BRIEF DESCRIPTION OF FIGURES

FIG. 1a is the nucleotide sequence of the *Arabidopsis thaliana* Qua-Quine Starch (QQS) cDNA [SEQ ID NO: 1].

FIG. 1b is the amino acid sequence of the *Arabidopsis thaliana* QQS protein [SEQ ID NO: 2].

DETAILED DESCRIPTION

Figure 2:
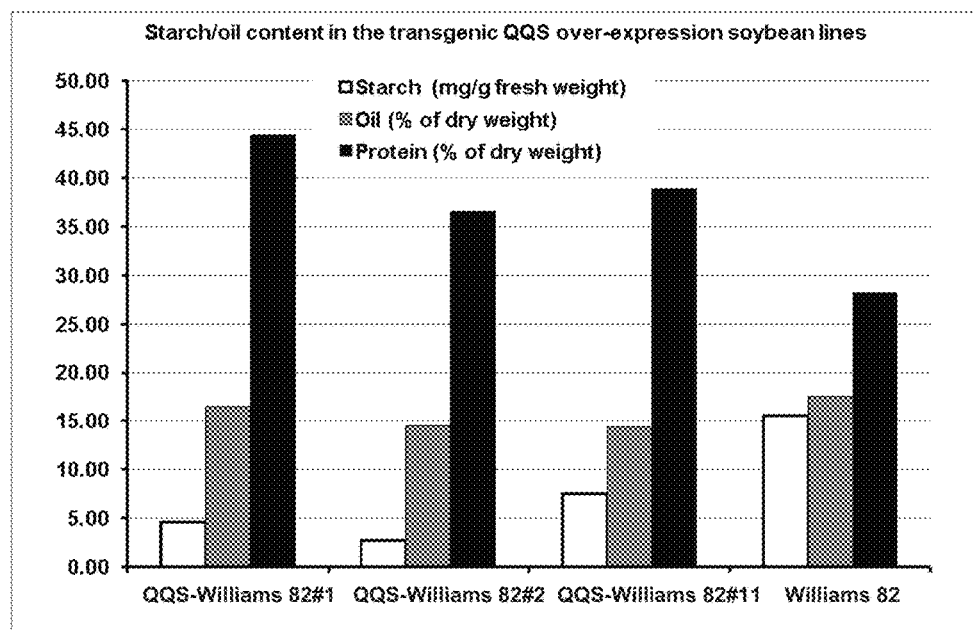
FIG. 2 is a bar graph of starch content (mg/g fresh weight), oil (% dry weight), and protein (% dry weight) in transgenic soybean lines vs. WT (Williams 82) soybean.

The present disclosure is predicated, at least in part, on the surprising and unexpected discovery that the qua-quine starch (QQS) gene (locus tag At3g30720; GenBank Accession Nos. EU805808.1 and NM_113075.4), which encodes a protein that contains 59 amino acids, has an effect on biochemical components in *Arabidopsis*, has no sequence similarity to other proteins in *Arabidopsis* or other organisms, has no known catalytic motifs, and no known structural motifs, also has an effect on biochemical components in other plants. The ability to modify the amount of at least one biochemical component in a plant by expressing QQS in the plant enables the generation of plant lines with more desirable biochemical component compositions without conducting extensive breeding studies.

In view of the above, a method of modifying the amount of at least one biochemical component in a plant is provided. The method comprises expressing QQS in the plant, the WT of which does not express QQS, in an amount (i.e., an effective amount, e.g., a biochemical component-modifying amount), or at a level (i.e., an effective level, e.g., a biochemical component-modifying level), that modifies the amount of at least one biochemical component in the plant. When QQS is expressed in the plant (the wild-type of which does not express QQS) and the amount of at least one biochemical component in the plant is modified, QQS is being expressed in the plant in an amount, or at a level, that modifies the amount of at least one biochemical component in the plant. The method can be used to produce a food product (or a component or an ingredient thereof) for human consumption, feed (or a component or an ingredient thereof) for non-human animal consumption, or an industrial product (i.e., any and all non-food products, or components or ingredients thereof), such as in accordance with methods described herein. In this regard, the "biochemical component," as described herein below, e.g., a biochemical component, which is increased in amount, or a plant (or part thereof), in which a biochemical component is increased/decreased in amount, can be the food product (or a component or an ingredient thereof), the feed (or a component or an ingredient thereof), or the industrial product (or a component or an ingredient thereof).

By "biochemical component" is meant any fraction of the composition of a plant (e.g., carbon fraction, nitrogen fraction, phosphorus fraction, or ion fraction), any class of compounds/ions of which a fraction is comprised (e.g., polysaccharides, sugars, organic acids, phenolics, tannins, hemicelluloses, lipids, terpenoids, cellulose and lignin of the carbon fraction; protein, amino acid, alkaloid, nitrate and nucleic acid of the nitrogen fraction; phosphate, polyphosphate, phospholipid, nucleic acid, and sugar phosphate of the phosphorus fraction; and potassium, calcium, magnesium, salt, and heavy metal of the ion fraction), and any compound of which a class of compounds is comprised that is built-up in a plant and can be mobilized to support biosynthesis for growth or other plant functions (see, e.g., Chapin, III et al., Ann. Rev. of Ecology and Systematics 21: 423-447 (1990) and references cited therein, all of which are hereby incorporated by reference in their entireties). Examples of plant lipid classes include neutral lipids, such as triacylglycerol, diacylglycerol, and monoacylglycerol, and polar lipids, such as monogalactosyldiacylglycerol, digalactosyldiacylglycerol, phosphatidylglycerol, phosphatidylcholine, phosphatidylethanolamine, phosphatidylinositol, phsophatidylserine, and sulfoquinovosyldiacylglycerol. Common plant fatty acids include palmitic acid, palmitoleic acid, palmitolenic acid, stearic acid, oleic acid, linoleic acid, linolenic acid, arachidic acid, eicosenoic acid, eicosadienoic acid, and erucic acid. A "biochemical component" is intended to encompass a compound that can be formed by one or more types of storage processes (e.g., starch and amino acids) and a compound that can serve a storage role and a non-storage role (e.g., ribulose bis-phosphate carboxylase (RUBISCO) and tannins). The biochemical component can be protein, lipid (e.g., oil), polyketide, isoprenoid, and/or carbohydrate (e.g., starch).

By "modifying" is meant increasing or decreasing the amount of a biochemical component. In this regard, the expression of QQS in the plant can modify one or more biochemical components by increasing the amount of one or more biochemical components, decreasing the amount of one or more biochemical components, or simultaneously increasing the amount of one of more biochemical components and decreasing the amount of one or more other biochemical components. Thus, the biochemical component can be protein, and the amount of protein in the seeds, for example, of the plant expressing QQS can be increased compared to the amount of protein in the seeds of the WT plant. Additionally or alternatively, the biochemical component can be lipid (e.g., oil), and the amount of lipid (e.g., oil) in the seeds, for example, of the plant expressing QQS can be decreased compared to the amount of lipid (e.g., oil) in the seeds of the WT plant. Also, additionally or alternatively, the biochemical component can be carbohydrate (e.g., starch), and the amount of carbohydrate (e.g., starch) in the leaves, seeds, or leaves and seeds, for example, of the plant expressing QQS can be decreased compared to the amount of carbohydrate (e.g., starch) in the leaves, seeds, or leaves and seeds, respectively, of the WT plant. The amount of at least one biochemical component can be modified, such as by increasing or decreasing, by at least about 5%, 10%, 15%, 20%, 25%, 30%, 35%, 40%, 45%, 50%, 55%, 60%, 65%, 70%, 75%, 80%, 85%, 90%, 95% or more. For example, as demonstrated herein, when the plant is soybean and the biochemical component is protein, the amount of protein in the seeds of the soybean can be increased by at least about 30%, such as 32.63% (based on dry weight), at least about 45%, such as 47.08% (based on dry weight), at least about 60%, such as 60.63% (based on dry weight), or more.

When the amount of at least one biochemical component is modified by increasing the amount of the biochemical component, it can be preferable and even desirable to supplement the growing conditions of the plant, such as soil or other media in which the plant is grown, with a composition that provides one or more nutrients essential to the growth of the plant and/or the increased production of at least one biochemical component in the plant. The composition can be inorganic (e.g., mineral), organic (e.g., derived from a plant and/or animal), or a combination thereof. The composition can be of natural origin, synthetic origin, or a combination thereof. An example of such a composition is a fertilizer (e.g., Miracle Gro Excel 15-5-15). A fertilizer typically provides, in varying proportions, macronutrients, such as nitrogen, phosphorus, potassium, calcium, magnesium, and sulfur. A fertilizer also typically provides, in varying proportions, micronutrients, such as boron, chlorine, copper, iron, manganese, molybdenum, and zinc. Other nutrients, such as carbon, hydrogen, and oxygen, are typically supplied by water and carbon dioxide. If desired, the composition (e.g., fertilizer) can be a controlled-release composition. In this regard, the components of the controlled-release composition can be released at the same rate or at different rates and/or in the same amounts or in different amounts. An excess amount of a given biochemical component can be released from a plant, which expresses a biochemical-component modifying amount/level of QQS, into its environment as part of the plant's normal growth/development or life cycle.

Also provided is a method of increasing resistance to a stress, such as an abiotic (e.g., salt, drought, pollution) or biotic (e.g., pathogen or a pest) stress, in a plant. The method comprises introducing into the plant, the wild-type of which does not comprise and express QQS, and expressing therein a polynucleotide comprising a nucleotide sequence encoding a QQS polypeptide having the amino acid sequence as set forth in SEQ ID NO: 2, wherein the nucleotide sequence is operably linked to a promoter. In an embodiment, the method comprises (a) transforming plant cells with a polynucleotide comprising a nucleotide sequence encoding a QQS polypeptide having the amino acid sequence as set forth in SEQ ID NO: 2, and wherein the nucleotide sequence is operably linked to a promoter; (b) regenerating transgenic plants from the transformed plant cells; and (c) identifying and selecting a transformed plant from the transgenic plants which exhibits increased resistance to a pathogen or a pest as compared to an untransformed plant of the same species lacking the QQS polypeptide and grown under similar conditions, wherein the increased resistance to a pathogen or pest is due to the expression of the QQS polypeptide in the selected transformed plant. The promoter can be constitutive, inducible, developmentally specific, synthetic or hybrid. The constitutive promoter can be a cauliflower mosaic virus 35S promoter. The developmentally specific promoter can be a seed-specific promoter. The pathogen can be a bacterium, a virus, a fungus, or a seed plant. The pest can be an insect (such as an aphid), a plasmodiophorid, a mite, or a nematode.

The plant can be any plant in which the modification of the amount of a biochemical component or the increase in resistance to a pathogen or a pest is desired. For example, the plant can be a monocot or a dicot. Examples of plants include agriculturally important plants, such as cereal crops, industrial plants, legumes, fruits, vegetables, root plants, turf grasses, woody plants, tropical plants, nuts, ornamental plants, medicinal plants, and fungi, among others, and, more specifically, corn, soybean, wheat, barley, oat, flax, kiwicha, bulgur, quinoa, millet, sorghum, sugarcane, potato, sweet potato, cotton, rice (e.g., indica and japonica), rye, canola, oilseed rape, sunflower, tobacco, beans, alfalfa, Bermudagrass, perennial ryegrass, switchgrass, tall fescue, turf grasses, American elm, American chestnut, cork oak tree, eucalyptus, pine, poplar, rubber tree, banana, blackberry, blueberry, strawberry, raspberry, cantaloupe, melon, cucumber, eggplant, tomato, lettuce, radish, mushroom, carrot, cassava, onion, lentil, pea, chickpea, pigeonpea, cowpea, red clover, bean, lima bean, kidney bean, broad bean, velvet bean, tepary bean, pepper, broccoli, spinach, squash, pumpkin, mustard, mustard greens, Indian mustard, apple, pear, peach, cherry, plum, grape, cabbage, cauliflower, brussel sprouts, citrus, orange, lemon, lime, grapefruit, tangerine, clementine, pomegranate, kiwi, starfruit, anise, papaya, pineapple, coffee, groundnut, palm kernel, walnut, peanut, almond, pecans, chestnuts, macadamia nuts, hazelnuts, sunflower, endive, leek, beet, turnip, clover, red clover, barrel clover, carnation, chrysanthemum, orchids, petunia, rose, ginseng, hemp, opium poppy, African locust bean, African oil bean, tarwi, tamarind, Mung bean, Sesban bean, Lablab bean, Jack-bean, lupin, and milkweed.

The pathogen can be a bacterium, a virus, a fungus, or a seed plant. The pest can be an insect (such as an aphid), a plasmodiophorid, a mite, or a nematode.

The bacterium can be any plant bacterium. Examples include, but are not limited to, a Firmicute, an Actinobacterium, or a Proteobacterium. The Proteobacterium can be an Alphaproteobacterium, a Betaproteobacterium, or a Gammaproteobacterium. The Alphaproteobacterium can be an *Agrobacterium*, a *Sphingomonas*, or a *Candidatus Liberibacter*. The Betaproteobacterium can be an *Acidovorax*, a *Burkholderia*, a *Ralstonia*, or a *Xylophilus*. The Gammaproteobacterium can be an Enterobacteriaceae, a Pseudomonodaceae, or a Xanthomonodaceae. The Enterobacteriaceae can be *Brenneria*, *Dickeya*, *Enterobacter*, *Erwinia*, *Ewingella*, *Pantoea*, *Pectobacterium*, *Candidatus Phlomobacter*, *Samsonia*, or *Serratia*. The Pseudomonodaceae can be *Pseudomonas*. The Xanthomonodaceae can be *Xanthomonas* or *Xylella*. The bacterium can be a *Clavibacter, Curtobacterium, Rathayibacter, Leifsonia, Nocardia, Rhodococcus, Streptomyces, Bacillus, Clostridium, Spiroplasma, Candidatus Phytoplasma*, or *Microbacteria*. Specific examples of bacteria include, but are not limited to, *Clavibacter michiganensis* or a subspecies thereof, *Curtobacterium flaccumfaciens, Rathayibacter rathayi, Rathayibacter tritici, Rathayibacter toxicus, Leifsonia xyli* or subspecies thereof, *Rhodococcus fascians, Sphingomonas suberifaciens, Sphingomonas melonis, Agrobacterium vitis, Agrobacterium tumefaciens, Agrobacterium rubi, Acrobacterium larrymoorei, Acidovorax avenae, A. avenae citrulli, A. avenae avenae, Burkholderia cepacia, Burkholderia gladioli, Burkholderia andropogonis, Burkholderia caryophylli, Burkholderia glumae, Burkholderia plantarii, Dickeya dadantii, Dickeya solani, Erwinia amylovora, Ralstonia solanacearum, Ralstonia syzygii, Candidatus Phlomobacter fragariae, Candidatus Liberibacter asiaticus, Pectobacterium carotovorum, Pectobacterium atrosepticum, Pseudomonas syringae, Pseudomonas savastanoi, Pseudomonas marginalis, Pseudomonas viridiflava, Xanthomonas arboricola, Xanthomonas axonopodis, Xanthomonas campestris, Xanthomonas hortorum, Xanthomonas oryzae, Xanthomonas axonopodis, Xanthomonas translucens, Xanthomonas vasicola*, or *Xylella fastidiosa*. According to Mansfield et al. (Mol. Plant Pathol. 13: 614-629 (2012)), the top bacterial plant pathogens are *Pseudomonas syringae* pathovars, *Ralstonia solanacearum, Agrobacterium tumefaciens, Xanthomonas oryze* pv. *oryze, Xanthomonas campestris* pathovars, *Xanthomonas axonopodis* pv. *manihotis, Erwinia amylovora, Xylella fastidiosa, Dickeya dadantii, Dickeya solani, Pectobacterium carotovorum*, and *Pectobacterium atrosepticum*.

The fungus can be any plant fungus. Examples include, but are not limited to, Ascomycetes, such as *Fusarium* spp. (causal agents of *Fusarium* wilt disease), *Fusarium graminearum, Fusarium oxysporum, Thielaviopsis* spp. (causal agents of canker rot, black root rot, and *Thielaviopsis* root rot), *Verticillium* spp., *Magnaporthe grisea* (causal agent of blast of rice and gray leaf spot in turfgrasses), *Magnaporthe oryzae, Sclerotinia sclerotiorum* (white mold), and powdery mildews. Other examples include Basidiomycetes, such as *Ustilago* spp., *Ustilago maydis, Rhizoctonia* spp., *Rhizoctonia solani, Phakospora pachyrhizi* (causal agent of soybean rust), *Puccinia* spp. (causal agents of severe rusts of virtually all cereal grains and cultivated grasses), and *Armillaria* spp. ("honey fungus" species; virulent pathogens of trees and produce-eligible mushrooms). According to Dean et al. (Mol. Plant Pathol. 13: 414-430 (2012)), the top ten plant fungal pathogens are *Magnaporthe oryzae, Botrytis cinerea, Puccinia* spp., *Fusarium graminearum, Fusarium oxysporum, Blumeria graminis, Mycosphaerella graminicola, Colletotrichum* spp., *Ustilago maydis*, and *Melampsora lini*. According to Kamoun et al. (Mol. Plant Pathol. 16: 413-434 (2015)), the top ten oomycetes are *Phytophthora infestans* (late blight), *Hyaloperonospora arabidopsidis* (downy mildew), *Phytophthora ramorum* (sudden oak death and *Ramorum* disease), *Phytophthora sojae* (stem and root rot), *Phytophthora capsici* (blight, stem and fruit rot, and various others), *Plasmopara viticola* (downy mildew), *Phytophthora cinnamomi* (root rot and dieback), *Phytophthora parsitica* (root and stem rot and various others), *Pythium ultimum* (damping off and root rot), and *Albugo candida* (white rust).

The seed plant can be dodder, mistletoe, or witchweed. Such plants are hemi-parasitic or parasitic on other plants.

The virus can be any plant virus. The virus can be transmitted through sap, by an insect, by a nematode, by a plasmodiophorid, by a mite, by a seed, or by pollen. Examples include, but are not limited to, members of the genera Alfamoviruses (e.g., Bromoviridae), Alphacryptoviruses (e.g., Partitiviridae), Badnaviruses, Betacryptoviruses (e.g., Partitiviridae), Bigeminiviruses (e.g., Geminiviridae), Bromoviruses (e.g., Bromoviridae), Bymoviruses (e.g., Potyviridae), Capilloviruses, Carlaviruses, Carmoviruses (e.g., Tombusviridae), Caulimoviruses, Closteroviruses, Comoviruses (e.g., Comoviridae), Cucumoviruses (e.g., Bromoviridae), Cytorhabdoviruses (e.g., Rhabdoviridae), Dianthoviruses, Enamoviruses, Fabaviruses (e.g., Comoviridae), Cucumoviruses (e.g., Bromoviridae), Cytorhabdoviruses (e.g., Rhabdoviridae), Dianthoviruses, Enamoviruses, Fabaviruses (e.g., Comoviridae), Fijiviruses (e.g., Reoviridae), Furoviruses, Hordeiviruses, Hybrigeminiviruses (e.g., Geminiviridae), Idaeoviruses, Ilarviruses (e.g. Bromoviridae), Ipomoviruses (e.g. Potyviridae), Luteoviruses, Machlomoviruses, Macluraviruses, Marafiviruses, Monogeminiviruses (e.g., Geminiviridae), Nanaviruses, Ncroviruses, Nepoviruses (e.g., Comoviridae), Nucleorhabdoviruses (e.g., Rhabdoviridae), Oryzaviruses (e.g., Reoviridae), Ourmiaviruses, Phytoreoviruses (e.g., Reoviridae), Potexviruses, Potyviruses (e.g., Potyviridae), Rymoviruses (e.g., Potyviridae), Sequiviruses (e.g., Sequiviridae), Sobemoviruses, Tenuiviruses, Tobamoviruses, Tobraviuses, Tombusviruses (e.g., Tombusviridae), Tospoviruses (e.g. Bunyaviridae), Trichoviruses, Tymoviruses, Umbraviruses, unassigned potyviruses (e.g., Potyviridae), unassigned rhabdoviruses (e.g. Rhabodiviridae), Varicosaviruses, Waikaviruses (e.g., Sequiviridae), and ungrouped viruses. Other examples of viruses include, but are not limited to, citrus tristeza virus, barley yellow dwarf virus, potato leafroll virus, and tomato bushy stunt virus. According to Scholthof et al. (Mol. Plant Pathol. 12: 938-954 (2011)), the top ten plant viruses are tobacco mosaic virus, tomato spotted wilt virus, tomato yellow leaf curl virus, cucumber mosaic virus, potato virus Y, cauliflower mosaic virus, African cassava mosaic virus, plum pox virus, Brome mosaic virus, and potato virus X.

Examples of viruses transmitted through sap include, but are not limited to, tobacco mosaic virus, potato virus X, potato virus Y, and a cucumber mosaic virus.

Examples of viruses transmitted by insects include, but are not limited to, Rhabdoviridae, Reoviridae, Potyvirus, Cucumovirus, Luteovirus, Begomovirus, Tospovirus, Comovirus, Sobemovirus, tomato yellow leaf curl virus, tomato pseudo-curly top virus, tomato spotted wilt virus, and lettuce infectious yellow virus. The insect can be an aphid, a whitefly, a hopper, a thrip, or a beetle. Aphids can spread Potyvirus, Cucumovirus, and Luteovirus. Whiteflies can spread Begomovirus, tomato yellow leaf curl virus, and lettuce infectious yellow virus. Hoppers can spread Rhabdoviridae, Reoviridae, and tomato pseudo-curly top virus. *Thrips* can spread Tospovirus and tomato spotted wilt virus. Beetles can spread Comovirus and Sobemovirus.

Nematodes can spread Nepovirus, Tobravirus, tobacco ringspot virus, and tobacco rattle virus, for example. According to Jones et al. (Mol. Plant Pathol. 14: 946-961 (2013)), the top ten nematodes are root-knot nematodes (i.e., *Meloidogyne* spp.), cyst nematodes (i.e., *Heterodera* spp. and *Globodera* spp.), root lesion nematodes (i.e., *Pratylenchus* spp.), the burrowing nematode (i.e., *Radopholus similis*), *Ditylenchus dipsaci*, the pine wilt nematode (i.e., *Bursaphelenchus xylophilus*), the reniform nematode (i.e., *Rotylenchulus reniformis*), *Xiphinema index*, Nacobbus *aberrans*, and *Aphelenchoides besseyi*.

Plasmodiophorids can spread Benyvirus, Bymovirus, Furovirus, Pecluvirus, Pomovirus, barley yellow mosaic virus, and beet necrotic yellow vein virus, for example.

Mites can spread Rymovirus, Tritimovirus, and wheat streak mosaic virus.

Seed can spread Hordeivirus, bean common mosaic virus, and barley stripe mosaic virus, for example.

QQS can be expressed in the plant using any suitable method as is known in the art. For example, QQS can be introduced into the plant as a transgene using electroporation, microprojectile bombardment, *Agrobacterium*-mediated transformation (as exemplified herein in Example 1), and direct contact of protoplasts. Transformation/transfection (as well as other techniques used to introduce DNA into a plant or fungus) and regeneration of monocots and dicots is a matter of routine. The particular method employed will depend, in part, on the type of plant or fungus to be transformed/transfected. For example, numerous protocols are described in *Agrobacterium* Protocols, $2^{nd}$ ed., Vols. 1 and 2, Methods in Molecular Biology, which was edited by Kan Wang and published by Humana Press, Totowa, N.J., and which is specifically incorporated herein by reference in its entirety. Such protocols include the floral dip transformation method and methods of transforming leaf explants, cotyledon explants, and root explants, as well as specific protocols for transformation of barrel clover, tobacco, barley, corn, rice (indica and japonica), rye, sorghum, wheat, canola, cotton, Indian mustard, sunflower, alfalfa, chickpea, clover, pea, peanut, pigeonpea, red clover, soybean, tepary bean, taro, cabbage, cucumber, eggplant, lettuce, tomato, carrot, cassava, potato, sweet potato, yam, Bermudagrass, perennial ryegrass, switchgrass, tall fescue, turf grasses, American elm, cork oak, eucalyptus tree, pine, poplar, rubber tree, banana, citrus, coffee, papaya, pineapple, sugarcane, American chestnut, apple, blueberry, grapevine, strawberry, walnut, carnation, chrysanthemum, orchids, petunia, rose, ginseng, hemp, opium poppy, and mushroom. Other methods of *Agrobacterium*-mediated transformation of cereals are described by Shrawat et al., Plant Biotech. J. 4(6): 575-603 (November 2006), which is specifically incorporated herein by reference in its entirety. Other methods of transformation of legumes are described by Somers et al., Plant Physiol. 131(3): 892-899 (March 2003), which is specifically incorporated herein by reference in its entirety. Methods useful for the transformation of rice are described by Giri et al., Biotech. Adv. 18(8): 653-683 (December 2000), and Hiei et al., Plant Mol. Biol. 35(1-2): 205-218 (September 1997), both of which are specifically incorporated herein by reference in their entireties. Vasil et al., Methods Molec. Biol. 111: 349-358 (1999), and Jones et al., Plant Methods 1(1): 5 (Sep. 5, 2005), both of which are specifically incorporated herein by reference in their entireties, describe methods useful for the transformation of wheat. The use of direct DNA uptake in barley has been described by Lazzeri, Methods Molec. Biol. 49: 95-106 (1996), which is specifically incorporated herein by reference in its entirety. The use of temporary immersion in a bioreactor system to transform strawberries is described by Hanhineva et al., BMC Biotech. 7: 11 (2007), which is specifically incorporated herein by reference in its entirety. The introduction of transgenes into plastids, such as chloroplasts, specifically chloroplasts in tobacco, has been described by Daniell et al., Trends Biotech. 23(5): 238-245 (May 2005), which is specifically incorporated herein by reference in its entirety. In this regard, Lutz et al., Plant Physiol. 145(4): 1201-1210 (2007) (specifically incorporated herein by reference in its entirety), provides guidance in the selection of vectors for transformation of the plastid genome in higher plants. Somatic embryogenesis of species-specific chloroplast vectors also has application in plants, such as soybean, carrot, and cotton, for example. Other methods useful for the transformation of beets have been described by Golovko et al., Tsitol. Genet. 39(3): 30-36 (May-June 2005), which is specifically incorporated herein by reference in its entirety.

A nucleotide sequence, which encodes the coding domain sequence (CDS) of QQS, can be incorporated into a vector or a cassette (collectively referred to herein as vectors) for expression in a plant. Numerous expression vectors suitable for stable transformation of plant cells or for the establishment of transgenic plants have been described (see, e.g., Weissbach et al., Methods for Plant Molecular Biology, Academic Press, New York, N.Y. (1989); and Gelvin et al., Plant Molecular Biology Manual, Kluwer Academic Publishers, Norwell, Mass. (1990)). The Ti plasmid from *Agrobacterium tumefaciens* or a binary *Agrobacterium* vector (Bevan, Nucl. Acids Res. 12: 8711-8721 (1984)) can be used to transform monocots and dicots. Non-Ti vectors, such as viral vectors, can be used to transfer DNA into plant cells, tissues, embryos, and plants. Non-Ti vectors can be introduced through the use of liposome-mediated transformation, polyethylene glycol (PEG)-mediated transformation, viral transfection, micro-injection, vacuum infiltration, electroporation of plant protoplasts, microprojectile bombardment, silicon carbide wiskers, and the like. See, e.g., Ammirato et al., Handbook of Plant Cell Culture—Crop Species, MacMillan Pub. Co. (1984); Shimamoto et al., Nature 338: 274-276 (1989); Fromm et al., Bio/Technology 8: 833-839 (1990); and Vasil et al., Biol. Technology 8: 429-434 (1990).

In addition to a coding sequence, a plant transformation/transfection vector comprises one or more 5' and 3' transcriptional regulatory sequences. Transcriptional regulatory sequences can include a promoter, a transcription initiation site, a transcription termination site, a polyadenylation signal, and a 3' terminator region (e.g., PI-II terminator region of potato, octopine synthase 3' terminator region, or nopaline synthase 3' terminator region). If a conventional, nuclear processed intron is present, one or more RNA processing signals, such as intron splice sites, also can be included. Any suitable promoter can be used. In this regard, the QQS promoter can be used. Alternatively, a non-QQS promoter can be used. The promoter can be constitutive, synthetic (e.g., hybrid), inducible, developmentally regulated, environmentally regulated, hormonally regulated, chemically regulated, cell-specific, or tissue-specific (e.g., seed-specific), for example. Constitutive promoters include the cauliflower mosaic virus (CaMV) 35S promoter, the nopaline synthase promoter, and the octopine synthase promoter. Environmentally regulated, inducible promoters include promoters that are induced by light, for example. The napin promoter, the phaseolin promoter, and the DC3 promoter are examples of seed-specific promoters, whereas the dru1 promoter, the 2A11 promoter, and the tomato polygalacturonase promoter are examples of fruit-specific promoters, and PTA29, PTA26, and PTA13 are examples of pollen-specific promoters. The pBAN promoter is a seed coat promoter in *Arabidopsis*, whereas p26, p63, and p63tr are early seed promoters from *Arabidopsis* (see, e.g., U.S. Pat. App. Pub. No. 2009/0031450). Examples of root-specific promoters are described in U.S. Pat. Nos. 5,618,988; 5,837,848; and 5,905,186. Other promoters are induced by auxin, cytokinin, gibberellin, methyl jasmonate, salicylic acid, heat, light, and the like.

In view of the above, a vector comprising a nucleotide sequence, which encodes the coding sequence of QQS, operably linked to a non-native promoter, which promotes expression of the nucleotide sequence in a plant, wherein the plant is other than *Arabidopsis*, is also provided. The nucleotide sequence preferably encodes the amino acid sequence of SEQ ID NO: 2. An example of such a nucleotide sequence is SEQ ID NO: 1, although one of ordinary skill in the art will appreciate that, due to the degeneracy of the genetic code, numerous other nucleotide sequences can encode the amino acid sequence of SEQ ID NO: 2. In this regard, one of ordinary skill in the art will also appreciate that one or more mutations can be introduced into the nucleotide sequence, thereby leading to changes in the amino acid sequence of QQS. If a mutation is introduced into the amino acid sequence of QQS, preferably the mutation does not alter the function of QQS or it improves the function of QQS in some way. By "non-native" is meant that the promoter is other than that which promotes the expression of QQS in WT *Arabidopsis*. "Non-native" is intended to encompass the use of other *Arabidopsis* promoters, i.e., other non-QQS promoters. As indicated above, the promoter can be any suitable promoter, such as a constitutive promoter, e.g., the cauliflower mosaic virus 35S promoter, a synthetic promoter (e.g., hybrid), an inducible promoter, a developmentally specific promoter, e.g., a seed-specific promoter, and a synthetic promoter, e.g., a hybrid promoter. Promoters that are highly active in soybean, e.g., a constitutive polyubiquitin promoter and an early embryo-specific heat shock protein 90-like promoter, are described in U.S. Pat. App. Pub. No. 2010/0186119. The method of modifying the amount of at least one biochemical component in a plant described herein is not limited to the use of a vector comprising a nucleotide sequence encoding the coding sequence of QQS operably linked to a non-native promoter; a vector comprising a nucleotide sequence encoding the coding sequence of QQS operably linked to the QQS promoter also can be used.

Following transformation/transfection (or other such methods of introducing DNA into a plant), plants can be selected using a dominant selectable marker (e.g., antibiotic or herbicide resistance) incorporated into the vector/cassette. After transformed/transfected plants are selected, they are grown to maturity. Plants showing a modified amount of at least one biochemical component are identified. Modulation can be confirmed through analysis of mRNA expression using Northern blots, RT-PCR, micro-arrays, or next generation sequencing, or through analysis of protein expression/accumulation using immunoblots, Western blots, or gel shift assays.

In view of the above, a transgenic plant, or part thereof, is also provided. The transgenic plant, or part thereof, comprises and expresses QQS as a transgene and at least one biochemical component is present in an amount that differs from the amount present in a corresponding WT plant, or part thereof, which does not express QQS. By "part thereof" is mean any part of a plant such as, but not limited to, root, stem, leaf, flower, stamen, pollen, pistil, seed, and the like. The transgenic plant can be any plant as indicated above, such as, but not limited to, soybean. In an embodiment, a plant, the wild-type of which does not comprise and express QQS and into which a polynucleotide comprising a nucleotide sequence encoding a QQS polypeptide having the amino acid sequence as set forth in SEQ ID NO: 2 has been introduced and expressed therein, is provided. The nucleotide sequence is operably linked to a promoter. The plant has increased protein content or increased resistance to a pathogen or a pest. Also provided is a seed of the plant, a hybrid of the plant, and a seed of the hybrid.

Also provided is a tissue culture of regenerable cells of the transgenic plant. By "tissue culture" is meant a composition comprising isolated cells, which can be the same or different, or a collection of such cells organized into one or more parts of a plant. Exemplary types of tissue cultures include an explant, a callus, an embryo, and a plantlet. By "regenerable" is meant that the cells can regenerate a plant like the transgenic plant from which the tissue culture was derived. Plant tissue culture techniques are known in the art (see, for example, Smith, *Plant Tissue Culture: Techniques and Experiments,* 2nd. ed., Academic Press (2000); and *Plant Tissue Culture, Development, and Biotechnology*, Trigiano and Gray, eds., CRC Press (2010), both of which are incorporated by reference in their entireties) and exemplified herein (see Example 2).

A method of producing a food or industrial product is also provided. "Food" includes food (or a component or an ingredient thereof) for human consumption as well as feed (or a component or an ingredient thereof) for non-human animal consumption. "Industrial" includes any and all non-food products (or components or ingredients thereof). The method can comprise preparing the food product (or a component or an ingredient thereof) or the industrial product (or a component or an ingredient thereof) from a cultivated transgenic plant as described above, e.g., soybean, or a cultivated plant regenerated from a tissue culture as described above. Thus, the present disclosure provides an improved method of producing a food product or an industrial product, wherein the improvement comprises preparing the food product or the industrial product from a cultivated transgenic plant or a cultivated plant regenerated from a tissue culture as described above.

Soybeans, for example, can be used in their entireties but are commonly processed into two primary products, i.e., soybean protein (meal) and crude soybean oil. Both of these products are commonly further refined for particular uses. The crude soybean oil can be broken down into glycerol, fatty acids, and sterols. The soybean protein can be divided into soy flour concentrates and isolates. Examples of "food" products made from soybean include, but are not limited to, coffee creamers, margarine, mayonnaise, salad dressings, shortenings, bakery products, chocolate coatings, cereal, beer, aquaculture feed, bee feed, calf feed replacers, fish feed, livestock feed, poultry feed, and pet feed. Examples of "industrial" products include, but are not limited to, binders, wood composites, anti-static agents, caulking compounds, solvents, disinfectants, fungicides, inks, paints, protective coatings, wallboard, anti-foam agents, and rubber.

If desired, the plants described herein can be used in plant breeding methods. For example, plant breeding methods can be used to introduce one or more other traits, e.g., higher yield, into the plants described herein. See, for example, the methods described in U.S. Pat. App. Pub. No. 2004/0060082, which published Mar. 25, 2004, and is hereby incorporated by reference in its entirety. Thus, another method of producing a plant with increased protein content or increased resistance to a pathogen or a pest is provided. The method comprises crossing a plant obtained in accordance with an above method with a second plant to produce progeny plants and selecting progeny plants with increased protein content or increased resistance to a pathogen or a pest.

The methods described herein can be used to assess other proteins with obscure features (POF) in plants. Desirably, the POF shares certain characteristics with QQS, such as no sequence similarity to other proteins within the same plant, or no sequence similarity to other proteins in other plant species, such as related plant species within the same family, no known catalytic motifs, and no known structural motifs. Initially, the POF can be identified by comparing its primary amino acid sequence to other amino acid sequences in databases, such as PFAM, TIGRFAM, SMART, and Superfamily, using a statistical model of a consensus sequence for a group of homologous and/or orthologous polypeptides, such as a Hidden Markov Model (HMM) (see, e.g., Durbin et al., *Biological Sequence Analysis Probabilistic Models of Proteins and Nucleic Acids*, Cambridge University Press, Cambridge, UK (1988)), and finding no matches (Gollery et al., Genome Biol. 7: R57 (2006)). Examples of POFs identified in *Arabidopsis* by this method include: Locus ID AT1G01110, AT1G01130, AT1G01240, AT1G01400, AT1G01440, AT1G01500, AT1G01550, AT1G01725, AT1G01730, AT1G01810, AT1G01840, AT1G01990, AT1G02070, AT1G02110, AT1G02290, AT1G02320, AT1G02350, AT1G02380, AT1G02405, AT1G02450, AT1G02490, AT1G02540, AT1G02570, AT1G02700, AT1G02710, AT1G02870, AT1G02960, AT1G02965, AT1G02990, AT1G03055, AT1G03080, AT1G03090, AT1G03106, AT1G03170, AT1G03180, AT1G03200, AT1G03240, AT1G03260, AT1G03290, AT1G03320, AT1G03340, AT1G03420, AT1G03600, AT1G03660, AT1G03730, AT1G03780, AT1G03820, AT1G03910, AT1G04000, AT1G04030, AT1G04070, AT1G04200, AT1G04230, AT1G04330, AT1G04650, AT1G04660, AT1G04670, AT1G04750, AT1G04800, AT1G04930, AT1G04985, AT1G05040, AT1G05060, AT1G05065, AT1G05085, AT1G05090, AT1G05205, AT1G05210, AT1G05220, AT1G05320, AT1G05330, AT1G05340, AT1G05360, AT1G05385, AT1G05420, AT1G05430, AT1G05440, AT1G05450, AT1G05490, AT1G05575, AT1G05720, AT1G05780, AT1G05860, AT1G05894, AT1G06010, AT1G06135, AT1G06225, AT1G06240, AT1G06320, AT1G06420, AT1G06475, AT1G06500, AT1G06510, AT1G06540, AT1G06660, AT1G06770, AT1G06920, AT1G06923, AT1G06930, AT1G06950, AT1G06980, AT1G07020, AT1G07040, AT1G07060, AT1G07090, AT1G07135, AT1G07190, AT1G07290, AT1G07300, AT1G07330, AT1G07473, AT1G07476, AT1G07500, AT1G07680, AT1G07690, AT1G07795, AT1G07860, AT1G07910, AT1G07970, AT1G07985, AT1G07990, AT1G08020, AT1G08030, AT1G08035, AT1G08060, AT1G08180, AT1G08300, AT1G08380, AT1G08480, AT1G08520, AT1G08530, AT1G08580, AT1G09415, AT1G09470, AT1G09483, AT1G09645, AT1G09812, AT1G09950, AT1G09995, AT1G10100, AT1G10140, AT1G10155, AT1G10170, AT1G10180, AT1G10220, AT1G10250, AT1G10380, AT1G10385, AT1G10417, AT1G10420, AT1G10522, AT1G10530, AT1G10620, AT1G10650, AT1G10660, AT1G10690, AT1G10710, AT1G10790, AT1G10800, AT1G10840, AT1G10990, AT1G11070, AT1G11120, AT1G11240, AT1G11320, AT1G11400, AT1G11430, AT1G11440, AT1G11470, AT1G11480, AT1G11520, AT1G11655, AT1G11690, AT1G11850, AT1G11905, AT1G11915, AT1G12020, AT1G12040, AT1G12064, AT1G12080, AT1G12330, AT1G12380, AT1G12450, AT1G12530, AT1G12660, AT1G12670, AT1G12805, AT1G12810, AT1G12830, AT1G12845, AT1G13030, AT1G13220, AT1G13360, AT1G13390, AT1G13605, AT1G13607, AT1G13608, AT1G13609, AT1G13620, AT1G13650, AT1G13670, AT1G13755, AT1G13930, AT1G13990, AT1G14180, AT1G14280, AT1G14345, AT1G14450, AT1G14620, AT1G14630, AT1G14710, AT1G14755, AT1G14990, AT1G15010, AT1G15215, AT1G15230, AT1G15260, AT1G15270, AT1G15280, AT1G15320, AT1G15350, AT1G15385, AT1G15400, AT1G15415, AT1G15590, AT1G15600, AT1G15610, AT1G15620, AT1G15630, AT1G15640, AT1G15757, AT1G15770, AT1G15800, AT1G15825, AT1G15830, AT1G15840, AT1G15900, AT1G15940, AT1G16000, AT1G16020, AT1G16025, AT1G16080, AT1G16170, AT1G16500, AT1G16515, AT1G16630, AT1G16690, AT1G16730, AT1G16770, AT1G16790, AT1G16810, AT1G16840, AT1G16850, AT1G16860, AT1G16910, AT1G16950, AT1G16960, AT1G17030, AT1G17080, AT1G17090, AT1G17140, AT1G17270, AT1G17285, AT1G17300, AT1G17345, AT1G17350, AT1G17360, AT1G17400, AT1G17490, AT1G17510, AT1G17665, AT1G17780, AT1G17870, AT1G17900, AT1G17940, AT1G18000, AT1G18010, AT1G18060, AT1G18190, AT1G18220, AT1G18290, AT1G18380, AT1G18470, AT1G18510, AT1G18620, AT1G18730, AT1G18750, AT1G18810, AT1G18840, AT1G18850, AT1G18950, AT1G19010, AT1G19020, AT1G19030, AT1G19240, AT1G19330, AT1G19360, AT1G19394, AT1G19397, AT1G19400, AT1G19500, AT1G19520, AT1G19530, AT1G19620, AT1G19960, AT1G19980, AT1G19990, AT1G20070, AT1G20100, AT1G20180, AT1G20280, AT1G20290, AT1G20310, AT1G20430, AT1G20460, AT1G20530, AT1G20640, AT1G20690, AT1G20770, AT1G20830, AT1G20890, AT1G20970, AT1G21010, AT1G21020, AT1G21050, AT1G21170, AT1G21323, AT1G21330, AT1G21360, AT1G21370, AT1G21390, AT1G21395, AT1G21475, AT1G21500, AT1G21510, AT1G21520, AT1G21560, AT1G21580, AT1G21600, AT1G21610, AT1G21695, AT1G21740, AT1G21770, AT1G21830, AT1G21840, AT1G21940, AT1G21950, AT1G22010, AT1G22030, AT1G22060, AT1G22110, AT1G22120, AT1G22140, AT1G22230, AT1G22260, AT1G22275, AT1G22335, AT1G22420, AT1G22470, AT1G22590, AT1G22600, AT1G22680, AT1G22770, AT1G22790, AT1G22850, AT1G22885, AT1G22890, AT1G22970, AT1G22980, AT1G23040, AT1G23050, AT1G23060, AT1G23110, AT1G23150, AT1G23170, AT1G23230, AT1G23270, AT1G23510, AT1G23530, AT1G23540, AT1G23650, AT1G23830, AT1G23840, AT1G23850, AT1G24050, AT1G24060, AT1G24145, AT1G24160, AT1G24270, AT1G24310, AT1G24370, AT1G24380, AT1G24390, AT1G24460, AT1G24560, AT1G24575, AT1G24600, AT1G24706, AT1G24822, AT1G24851, AT1G24938, AT1G24996, AT1G25025, AT1G25097, AT1G25112, AT1G25170, AT1G25180, AT1G25275, AT1G25400, AT1G25425, AT1G25540, AT1G26110, AT1G26140, AT1G26180, AT1G26210, AT1G26290, AT1G26350, AT1G26600, AT1G26650, AT1G26665, AT1G26710, AT1G26720, AT1G26750, AT1G27020, AT1G27030, AT1G27090, AT1G27300, AT1G27385, AT1G27435, AT1G27510, AT1G27550, AT1G27610, AT1G27640, AT1G27670, AT1G27690, AT1G27695, AT1G27710, AT1G27790, AT1G27850, AT1G27990, AT1G28060, AT1G28080, AT1G28100, AT1G28135, AT1G28140, AT1G28150, AT1G28190, AT1G28240, AT1G28250, AT1G28260, AT1G28327, AT1G28375, AT1G28395, AT1G28400, AT1G28530, AT1G28540, AT1G28560, AT1G28630, AT1G28760, AT1G29010, AT1G29170, AT1G29179, AT1G29195, AT1G29270, AT1G29290, AT1G29300, AT1G29355, AT1G29480, AT1G29530, AT1G29540, AT1G29560, AT1G29580, AT1G29610, AT1G29620, AT1G29820, AT1G29830, AT1G29970, AT1G29980, AT1G30050, AT1G30190, AT1G30250, AT1G30260, AT1G30475, AT1G30515, AT1G30757, AT1G30795, AT1G30814, AT1G30835, AT1G30845, AT1G30850, AT1G30880, AT1G31050, AT1G31060, AT1G31130, AT1G31150, AT1G31175, AT1G31200, AT1G31250, AT1G31270, AT1G31335, AT1G31460, AT1G31520, AT1G31580, AT1G31620, AT1G31750, AT1G31772, AT1G31835, AT1G31870, AT1G31940, AT1G31960, AT1G31990, AT1G32000, AT1G32010, AT1G32040, AT1G32260, AT1G32290, AT1G32310, AT1G32337, AT1G32370, AT1G32390, AT1G32460, AT1G32570, AT1G32583, AT1G32610, AT1G32630, AT1G32650, AT1G32670, AT1G32680, AT1G32690, AT1G32720, AT1G32810, AT1G32920, AT1G32928, AT1G32975, AT1G33055, AT1G33135, AT1G33490, AT1G33500, AT1G33607, AT1G33640, AT1G33700, AT1G33710, AT1G33810, AT1G33820, AT1G33850, AT1G33860, AT1G34000, AT1G34010, AT1G34047, AT1G34095, AT1G34245, AT1G34280, AT1G34315, AT1G34350, AT1G34400, AT1G34440, AT1G34490, AT1G34520, AT1G34550, AT1G34570, AT1G34590, AT1G34630, AT1G34640, AT1G34730, AT1G34770, AT1G34910, AT1G35030, AT1G35040, AT1G35080, AT1G35100, AT1G35183, AT1G35230, AT1G35320, AT1G35340, AT1G35375, AT1G35430, AT1G35435, AT1G35500, AT1G35513, AT1G35570, AT1G35614, AT1G35617, AT1G35640, AT1G35663, AT1G35780, AT1G35820, AT1G35880, AT1G35890, AT1G35900, AT1G36020, AT1G36100, AT1G36230, AT1G36320, AT1G36380, AT1G36395, AT1G36640, AT1G36670, AT1G36675, AT1G36745, AT1G36756, AT1G36763, AT1G36925, AT1G36940, AT1G36960, AT1G36970, AT1G36990, AT1G37000, AT1G37010, AT1G37015, AT1G37037, AT1G37045, AT1G38380, AT1G38630, AT1G38790, AT1G38950, AT1G39350, AT1G40080, AT1G40087, AT1G40115, AT1G40125, AT1G40129, AT1G40133, AT1G40230, AT1G41650, AT1G41750, AT1G41770, AT1G41810, AT1G41820, AT1G41855, AT1G41870, AT1G41900, AT1G41920, AT1G42080, AT1G42190, AT1G42367, AT1G42393, AT1G42430, AT1G42515, AT1G42550, AT1G42580, AT1G42630, AT1G42700, AT1G42710, AT1G42740, AT1G42960, AT1G43205, AT1G43230, AT1G43310, AT1G43320, AT1G43330, AT1G43415, AT1G43570, AT1G43580, AT1G43590, AT1G43660, AT1G43720, AT1G43730, AT1G43777, AT1G43790, AT1G43810, AT1G43850, AT1G43920, AT1G43940, AT1G43970, AT1G44000, AT1G44010, AT1G44085, AT1G44222, AT1G44414, AT1G44740, AT1G44770, AT1G44780, AT1G44850, AT1G44875, AT1G44920, AT1G44930, AT1G44960, AT1G44990, AT1G45150, AT1G45165, AT1G45170, AT1G45230, AT1G45233, AT1G45248, AT1G45403, AT1G45688, AT1G46336, AT1G47200, AT1G47280, AT1G47310, AT1G47317, AT1G47395, AT1G47400, AT1G47410, AT1G47420, AT1G47485, AT1G47495, AT1G47640, AT1G47660, AT1G47680, AT1G47690, AT1G47700, AT1G47770, AT1G47783, AT1G47813, AT1G47820, AT1G47940, AT1G47970, AT1G48145, AT1G48170, AT1G48200, AT1G48250, AT1G48280, AT1G48290, AT1G48325, AT1G48330, AT1G48360, AT1G48380, AT1G48440, AT1G48460, AT1G48510, AT1G48530, AT1G48580, AT1G48720, AT1G48730, AT1G48780, AT1G48840, AT1G49000, AT1G49005, AT1G49110, AT1G49140, AT1G49150, AT1G49260, AT1G49290, AT1G49310, AT1G49330, AT1G49410, AT1G49490, AT1G49500, AT1G49510, AT1G49680, AT1G49700, AT1G49715, AT1G49800, AT1G49840, AT1G49870, AT1G49930, AT1G49940, AT1G49975, AT1G50020, AT1G50080, AT1G50150, AT1G50220, AT1G50290, AT1G50350, AT1G50530, AT1G50660, AT1G50710, AT1G50730, AT1G50800, AT1G50910, AT1G50930, AT1G51000, AT1G51010, AT1G51030, AT1G51080, AT1G51100, AT1G51130, AT1G51355, AT1G51400, AT1G51405, AT1G51430, AT1G51840, AT1G51915, AT1G51920, AT1G51970, AT1G52080, AT1G52087, AT1G52090, AT1G52140, AT1G52155, AT1G52220, AT1G52270, AT1G52320, AT1G52390, AT1G52410, AT1G52430, AT1G52440, AT1G52450, AT1G52550, AT1G52565, AT1G52615, AT1G52680, AT1G52720, AT1G52780, AT1G52825, AT1G52827, AT1G52840, AT1G52855, AT1G52905, AT1G53035, AT1G53040, AT1G53180, AT1G53250, AT1G53260, AT1G53265, AT1G53285, AT1G53380, AT1G53400, AT1G53450, AT1G53460, AT1G53480, AT1G53490, AT1G53560, AT1G53610, AT1G53620, AT1G53625, AT1G53640, AT1G53645, AT1G53760, AT1G53770, AT1G53785, AT1G53800, AT1G53935, AT1G53970, AT1G54110, AT1G54120, AT1G54180, AT1G54200, AT1G54215, AT1G54217, AT1G54300, AT1G54420, AT1G54445, AT1G54470, AT1G54575, AT1G54640, AT1G54680, AT1G54700, AT1G54720, AT1G54730, AT1G54740, AT1G54770, AT1G54780, AT1G54840, AT1G54860, AT1G54880, AT1G54920, AT1G54923, AT1G54926, AT1G54950, AT1G54955, AT1G54970, AT1G55080, AT1G55160, AT1G55220, AT1G55250, AT1G55330, AT1G55365, AT1G55400, AT1G55475, AT1G55535, AT1G55540, AT1G55545, AT1G55675, AT1G55710, AT1G55800, AT1G55928, AT1G55990, AT1G56020, AT1G56060, AT1G56085, AT1G56100, AT1G56180, AT1G56200, AT1G56260, AT1G56270, AT1G56320, AT1G56415, AT1G56420, AT1G56530, AT1G56553, AT1G56555, AT1G56660, AT1G57540, AT1G57565, AT1G57670, AT1G57680, AT1G57760, AT1G58055, AT1G58120, AT1G58150, AT1G58225, AT1G58235, AT1G58242, AT1G58250, AT1G58330, AT1G58420, AT1G58460, AT1G58520, AT1G58766, AT1G59077, AT1G59510, AT1G59520, AT1G59535, AT1G59590, AT1G59600, AT1G59722, AT1G59835, AT1G59840, AT1G59865, AT1G59885, AT1G59920, AT1G59930, AT1G60000, AT1G60010, AT1G60060, AT1G60240, AT1G60250, AT1G60380, AT1G60460, AT1G60560, AT1G60610, AT1G60640, AT1G60720, AT1G60870, AT1G60983, AT1G60987, AT1G61000, AT1G61030, AT1G61080, AT1G61090, AT1G61095, AT1G61097, AT1G61100, AT1G61170, AT1G61200, AT1G61255, AT1G61340, AT1G61410, AT1G61450, AT1G61688, AT1G61780, AT1G61900, AT1G61920, AT1G62000, AT1G62045, AT1G62060, AT1G62070, AT1G62080, AT1G62190, AT1G62210, AT1G62220, AT1G62225, AT1G62240, AT1G62250, AT1G62440, AT1G62480, AT1G62690, AT1G62780, AT1G62855, AT1G62870, AT1G62890, AT1G62935, AT1G63055, AT1G63060, AT1G63105, AT1G63240, AT1G63245, AT1G63300, AT1G63310, AT1G63522, AT1G63530, AT1G63535, AT1G63540, AT1G63610, AT1G63670, AT1G63720, AT1G63960, AT1G64050, AT1G64080, AT1G64107, AT1G64140, AT1G64180, AT1G64295, AT1G64320, AT1G64330, AT1G64340, AT1G64355, AT1G64360, AT1G64370, AT1G64385, AT1G64405, AT1G64490, AT1G64560, AT1G64680, AT1G64690, AT1G64700, AT1G64800, AT1G64870, AT1G64990, AT1G65010, AT1G65090, AT1G65110, AT1G65120, AT1G65130, AT1G65200, AT1G65230, AT1G65270, AT1G65295, AT1G65342, AT1G65352, AT1G65470, AT1G65490, AT1G65500, AT1G65510, AT1G65710, AT1G65720, AT1G65845, AT1G66070, AT1G66080, AT1G66145, AT1G66190, AT1G66235, AT1G66245, AT1G66480, AT1G66790, AT1G66820, AT1G66840, AT1G66890, AT1G66940, AT1G67025, AT1G67035, AT1G67040, AT1G67050, AT1G67060, AT1G67080, AT1G67170, AT1G67195, AT1G67230, AT1G67350, AT1G67540, AT1G67635, AT1G67670, AT1G67700, AT1G67775, AT1G67790, AT1G67855, AT1G67860, AT1G67865, AT1G67870, AT1G67910, AT1G67920, AT1G67930, AT1G67950, AT1G68250, AT1G68330, AT1G68350, AT1G68430, AT1G68440, AT1G68490, AT1G68500, AT1G68680, AT1G68700, AT1G68725, AT1G68765, AT1G68790, AT1G68795, AT1G68845, AT1G68870, AT1G68875, AT1G68905, AT1G68907, AT1G68910, AT1G68935, AT1G68945, AT1G69050, AT1G69160, AT1G69170, AT1G69230, AT1G69280, AT1G69320, AT1G69380, AT1G69390, AT1G69430, AT1G69470, AT1G69760, AT1G69825, AT1G69935, AT1G69970, AT1G69980, AT1G70100, AT1G70160, AT1G70200, AT1G70220, AT1G70350, AT1G70470, AT1G70505, AT1G70620, AT1G70760, AT1G70770, AT1G70780, AT1G70895, AT1G70900, AT1G70985, AT1G70990, AT1G71015, AT1G71080, AT1G71110, AT1G71190, AT1G71235, AT1G71240, AT1G71310, AT1G71430, AT1G71470, AT1G71730, AT1G71740, AT1G71760, AT1G71780, AT1G71865, AT1G71910, AT1G71940, AT1G72020, AT1G72080, AT1G72240, AT1G72380, AT1G72390, AT1G72410, AT1G72420, AT1G72430, AT1G72490, AT1G72530, AT1G72580, AT1G72590, AT1G72600, AT1G72645, AT1G72690, AT1G72720, AT1G72790, AT1G73060, AT1G73090, AT1G73120, AT1G73130, AT1G73165, AT1G73177, AT1G73240, AT1G73350, AT1G73470, AT1G73510, AT1G73603, AT1G73607, AT1G73770, AT1G73790, AT1G73840, AT1G73885, AT1G73940, AT1G73965, AT1G73970, AT1G74045, AT1G74055, AT1G74160, AT1G74220, AT1G74530, AT1G74860, AT1G74880, AT1G75060, AT1G75110, AT1G75150, AT1G75160, AT1G75180, AT1G75190, AT1G75260, AT1G75310, AT1G75360, AT1G75550, AT1G75730, AT1G75770, AT1G75810, AT1G75860, AT1G75870, AT1G76070, AT1G76185, AT1G76200, AT1G76230, AT1G76250, AT1G76340, AT1G76405, AT1G76450, AT1G76480, AT1G76600, AT1G76610, AT1G76660, AT1G76740, AT1G76780, AT1G76820, AT1G76840, AT1G76850, AT1G76910, AT1G76955, AT1G76960, AT1G76965, AT1G76980, AT1G77150, AT1G77270, AT1G77310, AT1G77350, AT1G77400, AT1G77500, AT1G77540, AT1G77655, AT1G77765, AT1G77855, AT1G77885, AT1G77890, AT1G77910, AT1G77960, AT1G78030, AT1G78070, AT1G78110, AT1G78150, AT1G78170, AT1G78650, AT1G78790, AT1G78810, AT1G78815, AT1G78880, AT1G78890, AT1G78895, AT1G78995, AT1G79020, AT1G79060, AT1G79070, AT1G79090, AT1G79100, AT1G79110, AT1G79160, AT1G79170, AT1G79200, AT1G79260, AT1G79390, AT1G79420, AT1G79430, AT1G79660, AT1G79830, AT1G79915, AT1G79970, AT1G79975, AT1G80000, AT1G80110, AT1G80180, AT1G80200, AT1G80210, AT1G80240, AT1G80245, AT1G80310, AT1G80540, AT1G80610, AT1G80700, AT1G80810, AT1G80860, AT1G80865, AT1G80890, AT1G80910, AT1G80940, AT1G80980, AT2G01031, AT2G01060, AT2G01100, AT2G01120, AT2G01175, AT2G01200, AT2G01300, AT2G01310, AT2G01340, AT2G01400, AT2G01505, AT2G01580, AT2G01590, AT2G01620, AT2G01640, AT2G01650, AT2G01670, AT2G01755, AT2G01800, AT2G01870, AT2G01913, AT2G01940, AT2G01960, AT2G01990, AT2G02070, AT2G02280, AT2G02350, AT2G02370, AT2G02440, AT2G02490, AT2G02510, AT2G02515, AT2G02520, AT2G02795, AT2G02835, AT2G02840, AT2G02880, AT2G02910, AT2G02950, AT2G03010, AT2G03070, AT2G03150, AT2G03180, AT2G03310, AT2G03320, AT2G03420, AT2G03440, AT2G03540, AT2G03570, AT2G03580, AT2G03630, AT2G03680, AT2G03810, AT2G03830, AT2G03932, AT2G03937, AT2G04000, AT2G04025, AT2G04034, AT2G04039, AT2G04045, AT2G04046, AT2G04063, AT2G04135, AT2G04235, AT2G04280, AT2G04305, AT2G04320, AT2G04340, AT2G04360, AT2G04370, AT2G04380, AT2G04410, AT2G04460, AT2G04480, AT2G04495, AT2G04515, AT2G04600, AT2G04675, AT2G04790, AT2G04795, AT2G04800, AT2G04870, AT2G04925, AT2G05000, AT2G05030, AT2G05117, AT2G05120, AT2G05185, AT2G05270, AT2G05290, AT2G05310, AT2G05350, AT2G05360, AT2G05370, AT2G05500, AT2G05564, AT2G05620, AT2G05645, AT2G05647, AT2G05752, AT2G05915, AT2G05950, AT2G06005, AT2G06010, AT2G06040, AT2G06095, AT2G06140, AT2G06166, AT2G06200, AT2G06230, AT2G06390, AT2G06420, AT2G06480, AT2G06555, AT2G06570, AT2G06620, AT2G06630, AT2G06645, AT2G06750, AT2G06775, AT2G06820, AT2G06906, AT2G06908, AT2G06914, AT2G07000, AT2G07190, AT2G07215, AT2G07280, AT2G07290, AT2G07310, AT2G07440, AT2G07505, AT2G07520, AT2G07669, AT2G07672, AT2G07673, AT2G07674, AT2G07676, AT2G07678, AT2G07679, AT2G07691, AT2G07692, AT2G07701, AT2G07702, AT2G07705, AT2G07706, AT2G07708, AT2G07710, AT2G07713, AT2G07714, AT2G07719, AT2G07721, AT2G07722, AT2G07724, AT2G07728, AT2G07738, AT2G07760, AT2G07772, AT2G07773, AT2G07774, AT2G07775, AT2G07776, AT2G07777,
AT2G07779, AT2G07787, AT2G07795, AT2G07880,
AT2G07981, AT2G08986, AT2G09388, AT2G09840,
AT2G09865, AT2G09900, AT2G10020, AT2G10070,
AT2G10090, AT2G10105, AT2G10110, AT2G10175,
AT2G10285, AT2G10340, AT2G10360, AT2G10380,
AT2G10390, AT2G10470, AT2G10550, AT2G10555,
AT2G10560, AT2G10602, AT2G10608, AT2G10850,
AT2G10870, AT2G10920, AT2G10930, AT2G10965,
AT2G10975, AT2G10980, AT2G11005, AT2G11015,
AT2G11090, AT2G11135, AT2G11370, AT2G11405,
AT2G11462, AT2G11570, AT2G11620, AT2G11626,
AT2G11775, AT2G11910, AT2G12110, AT2G12120,
AT2G12130, AT2G12170, AT2G12290, AT2G12320,
AT2G12400, AT2G12405, AT2G12465, AT2G12475,
AT2G12505, AT2G12610, AT2G12685, AT2G12700,
AT2G12875, AT2G12905, AT2G12935, AT2G12945,
AT2G13125, AT2G13126, AT2G13270, AT2G13320,
AT2G13430, AT2G13450, AT2G13500, AT2G13510,
AT2G13550, AT2G13650, AT2G13660, AT2G13690,
AT2G13730, AT2G13760, AT2G13770, AT2G13865,
AT2G13975, AT2G14000, AT2G14020, AT2G14045,
AT2G14095, AT2G14240, AT2G14247, AT2G14340,
AT2G14390, AT2G14460, AT2G14590, AT2G14600,
AT2G14635, AT2G14680, AT2G14700, AT2G14730,
AT2G14760, AT2G14774, AT2G14800, AT2G14810,
AT2G14850, AT2G14890, AT2G14910, AT2G14935,
AT2G15000, AT2G15020, AT2G15185, AT2G15290,
AT2G15327, AT2G15340, AT2G15345, AT2G15420,
AT2G15500, AT2G15520, AT2G15535, AT2G15550,
AT2G15600, AT2G15670, AT2G15800, AT2G15815,
AT2G15830, AT2G15860, AT2G15880, AT2G15890,
AT2G15930, AT2G15960, AT2G16015, AT2G16020,
AT2G16070, AT2G16170, AT2G16190, AT2G16200,
AT2G16270, AT2G16340, AT2G16365, AT2G16385,
AT2G16410, AT2G16485, AT2G16575, AT2G16586,
AT2G16595, AT2G16630, AT2G16676, AT2G16820,
AT2G17110, AT2G17160, AT2G17240, AT2G17300,
AT2G17320, AT2G17340, AT2G17350, AT2G17442,
AT2G17540, AT2G17550, AT2G17695, AT2G17710,
AT2G17723, AT2G17780, AT2G17785, AT2G17787,
AT2G17960, AT2G17972, AT2G17990, AT2G18070,
AT2G18200, AT2G18210, AT2G18240, AT2G18270,
AT2G18410, AT2G18440, AT2G18610, AT2G18680,
AT2G18690, AT2G18830, AT2G18870, AT2G18876,
AT2G18910, AT2G18920, AT2G18930, AT2G18970,
AT2G19000, AT2G19090, AT2G19180, AT2G19200,
AT2G19220, AT2G19270, AT2G19290, AT2G19300,
AT2G19320, AT2G19340, AT2G19390, AT2G19420,
AT2G19460, AT2G19530, AT2G19700, AT2G19802,
AT2G19850, AT2G19893, AT2G19950, AT2G20080,
AT2G20142, AT2G20150, AT2G20208, AT2G20230,
AT2G20240, AT2G20250, AT2G20310, AT2G20390,
AT2G20410, AT2G20463, AT2G20480, AT2G20495,
AT2G20500, AT2G20515, AT2G20585, AT2G20590,
AT2G20595, AT2G20616, AT2G20620, AT2G20625,
AT2G20700, AT2G20740, AT2G20760, AT2G20820,
AT2G20825, AT2G20835, AT2G20870, AT2G20875,
AT2G20890, AT2G20920, AT2G20970, AT2G20980,
AT2G21080, AT2G21180, AT2G21185, AT2G21195,
AT2G21237, AT2G21290, AT2G21385, AT2G21465,
AT2G21560, AT2G21640, AT2G21660, AT2G21720,
AT2G21725, AT2G21780, AT2G21800, AT2G21820,
AT2G21870, AT2G21960, AT2G21970, AT2G21980,
AT2G22000, AT2G22080, AT2G22121, AT2G22122,
AT2G22140, AT2G22270, AT2G22320, AT2G22340,
AT2G22470, AT2G22510, AT2G22520, AT2G22560,
AT2G22790, AT2G22795, AT2G22805, AT2G22807,
AT2G22820, AT2G22840, AT2G22890, AT2G22905,
AT2G22940, AT2G22941, AT2G23040, AT2G23090,
AT2G23093, AT2G23110, AT2G23120, AT2G23130,
AT2G23270, AT2G23370, AT2G23390, AT2G23440,
AT2G23490, AT2G23530, AT2G23670, AT2G23690,
AT2G23755, AT2G23920, AT2G23985, AT2G24100,
AT2G24285, AT2G24310, AT2G24330, AT2G24340,
AT2G24410, AT2G24440, AT2G24460, AT2G24550,
AT2G24617, AT2G24625, AT2G24762, AT2G24780,
AT2G24910, AT2G24945, AT2G24960, AT2G24970,
AT2G25185, AT2G25250, AT2G25260, AT2G25270,
AT2G25510, AT2G25565, AT2G25605, AT2G25625,
AT2G25670, AT2G25680, AT2G25685, AT2G25720,
AT2G25735, AT2G25920, AT2G25930, AT2G25990,
AT2G26110, AT2G26120, AT2G26340, AT2G26520,
AT2G26770, AT2G26810, AT2G26840, AT2G26880,
AT2G27090, AT2G27100, AT2G27180, AT2G27250,
AT2G27280, AT2G27285, AT2G27315, AT2G27380,
AT2G27385, AT2G27390, AT2G27402, AT2G27535,
AT2G27540, AT2G27630, AT2G27650, AT2G27730,
AT2G27775, AT2G27830, AT2G27840, AT2G27950,
AT2G28020, AT2G28130, AT2G28230, AT2G28240,
AT2G28330, AT2G28410, AT2G28430, AT2G28540,
AT2G28570, AT2G28605, AT2G28625, AT2G28725,
AT2G28755, AT2G28780, AT2G28870, AT2G28910,
AT2G29045, AT2G29180, AT2G29620, AT2G29790,
AT2G29880, AT2G29920, AT2G29995, AT2G30115,
AT2G30120, AT2G30230, AT2G30280, AT2G30350,
AT2G30370, AT2G30380, AT2G30395, AT2G30430,
AT2G30480, AT2G30505, AT2G30560, AT2G30680,
AT2G30700, AT2G30760, AT2G30820, AT2G30925,
AT2G30930, AT2G30942, AT2G30960, AT2G30985,
AT2G31035, AT2G31040, AT2G31081, AT2G31082,
AT2G31083, AT2G31085, AT2G31090, AT2G31120,
AT2G31130, AT2G31150, AT2G31160, AT2G31270,
AT2G31345, AT2G31410, AT2G31480, AT2G31490,
AT2G31590, AT2G31600, AT2G31700, AT2G31710,
AT2G31751, AT2G31850, AT2G31930, AT2G31945,
AT2G32130, AT2G32190, AT2G32200, AT2G32210,
AT2G32235, AT2G32240, AT2G32275, AT2G32380,
AT2G32760, AT2G32840, AT2G32890, AT2G32970,
AT2G32980, AT2G33180, AT2G33233, AT2G33250,
AT2G33390, AT2G33400, AT2G33435, AT2G33470,
AT2G33490, AT2G33520, AT2G33585, AT2G33690,
AT2G33720, AT2G33793, AT2G33850, AT2G33855,
AT2G34010, AT2G34100, AT2G34110, AT2G34120,
AT2G34123, AT2G34150, AT2G34185, AT2G34220,
AT2G34230, AT2G34240, AT2G34270, AT2G34310,
AT2G34315, AT2G34330, AT2G34510, AT2G34530,
AT2G34580, AT2G34585, AT2G34640, AT2G34655,
AT2G34670, AT2G34690, AT2G34730, AT2G34780,
AT2G34800, AT2G34870, AT2G34910, AT2G35070,
AT2G35075, AT2G35080, AT2G35090, AT2G35110,
AT2G35200, AT2G35215, AT2G35230, AT2G35260,
AT2G35290, AT2G35470, AT2G35480, AT2G35585,
AT2G35612, AT2G35670, AT2G35710, AT2G35733,
AT2G35736, AT2G35750, AT2G35790, AT2G35810,
AT2G35820, AT2G35830, AT2G35850, AT2G35870,
AT2G35900, AT2G35950, AT2G36030, AT2G36040,
AT2G36145, AT2G36220, AT2G36255, AT2G36295,
AT2G36400, AT2G36420, AT2G36440, AT2G36485,
AT2G36550, AT2G36695, AT2G36724, AT2G36835,
AT2G36885, AT2G36895, AT2G36920, AT2G36940,
AT2G37035, AT2G37070, AT2G37080, AT2G37100,
AT2G37195, AT2G37300, AT2G37370, AT2G37380,
AT2G37530, AT2G37610, AT2G37680, AT2G37750,
AT2G37860, AT2G37910, AT2G37920, AT2G37975,
AT2G38090, AT2G38140, AT2G38160, AT2G38220,
AT2G38350, AT2G38430, AT2G38440, AT2G38465,
AT2G38570, AT2G38580, AT2G38690, AT2G38695,
AT2G38790, AT2G38823, AT2G38890, AT2G39000,
AT2G39160, AT2G39170, AT2G39200, AT2G39300,

| | | | | | | | |
|---|---|---|---|---|---|---|---|
| AT2G39370, | AT2G39500, | AT2G39520, | AT2G39560, | AT3G07790, | AT3G07910, | AT3G07950, | AT3G08030, |
| AT2G39680, | AT2G39855, | AT2G39870, | AT2G39950, | AT3G08490, | AT3G08550, | AT3G08610, | AT3G08630, |
| AT2G40020, | AT2G40060, | AT2G40070, | AT2G40085, | AT3G08640, | AT3G08650, | AT3G08670, | AT3G08780, |
| AT2G40095, | AT2G40113, | AT2G40316, | AT2G40390, | AT3G08880, | AT3G08955, | AT3G09000, | AT3G09032, |
| AT2G40410, | AT2G40475, | AT2G40530, | AT2G40550, | AT3G09050, | AT3G09085, | AT3G09130, | AT3G09162, |
| AT2G40630, | AT2G40680, | AT2G40765, | AT2G40955, | AT3G09180, | AT3G09280, | AT3G09430, | AT3G09450, |
| AT2G41150, | AT2G41230, | AT2G41260, | AT2G41280, | AT3G09730, | AT3G09750, | AT3G09770, | AT3G09860, |
| AT2G41350, | AT2G41390, | AT2G41400, | AT2G41420, | AT3G09922, | AT3G09950, | AT3G10020, | AT3G10116, |
| AT2G41440, | AT2G41570, | AT2G41610, | AT2G41650, | AT3G10120, | AT3G10195, | AT3G10525, | AT3G10572, |
| AT2G41730, | AT2G41760, | AT2G41770, | AT2G41780, | AT3G10650, | AT3G10810, | AT3G10830, | AT3G10880, |
| AT2G41800, | AT2G41810, | AT2G41905, | AT2G41945, | AT3G10930, | AT3G10980, | AT3G11030, | AT3G11060, |
| AT2G41960, | AT2G41990, | AT2G42040, | AT2G42050, | AT3G11160, | AT3G11300, | AT3G11310, | AT3G11325, |
| AT2G42130, | AT2G42180, | AT2G42190, | AT2G42260, | AT3G11405, | AT3G11560, | AT3G11590, | AT3G11600, |
| AT2G42280, | AT2G42310, | AT2G42320, | AT2G42340, | AT3G11640, | AT3G11670, | AT3G11690, | AT3G11745, |
| AT2G42370, | AT2G42395, | AT2G42540, | AT2G42610, | AT3G11760, | AT3G11800, | AT3G11810, | AT3G11860, |
| AT2G42640, | AT2G42760, | AT2G42840, | AT2G42860, | AT3G11880, | AT3G12190, | AT3G12210, | AT3G12320, |
| AT2G42900, | AT2G42950, | AT2G42955, | AT2G42975, | AT3G12345, | AT3G12510, | AT3G12650, | AT3G12840, |
| AT2G43110, | AT2G43250, | AT2G43390, | AT2G43450, | AT3G12870, | AT3G12910, | AT3G12920, | AT3G12955, |
| AT2G43540, | AT2G43630, | AT2G43780, | AT2G43795, | AT3G12960, | AT3G12970, | AT3G12977, | AT3G13130, |
| AT2G43945, | AT2G43950, | AT2G43990, | AT2G44010, | AT3G13175, | AT3G13227, | AT3G13240, | AT3G13275, |
| AT2G44080, | AT2G44195, | AT2G44200, | AT2G44280, | AT3G13360, | AT3G13370, | AT3G13403, | AT3G13410, |
| AT2G44420, | AT2G44510, | AT2G44600, | AT2G44640, | AT3G13420, | AT3G13435, | AT3G13460, | AT3G13480, |
| AT2G44735, | AT2G44740, | AT2G44760, | AT2G44820, | AT3G13500, | AT3G13520, | AT3G13630, | AT3G13674, |
| AT2G44850, | AT2G45000, | AT2G45060, | AT2G45250, | AT3G13677, | AT3G13780, | AT3G13845, | AT3G13857, |
| AT2G45260, | AT2G45380, | AT2G45403, | AT2G45450, | AT3G13910, | AT3G13950, | AT3G13960, | AT3G13980, |
| AT2G45480, | AT2G45520, | AT2G45690, | AT2G45780, | AT3G14060, | AT3G14190, | AT3G14280, | AT3G14340, |
| AT2G45860, | AT2G45900, | AT2G45930, | AT2G45980, | AT3G14395, | AT3G14430, | AT3G14480, | AT3G14560, |
| AT2G46000, | AT2G46060, | AT2G46080, | AT2G46180, | AT3G14595, | AT3G14670, | AT3G14750, | AT3G14760, |
| AT2G46200, | AT2G46250, | AT2G46360, | AT2G46375, | AT3G14780, | AT3G14830, | AT3G14840, | AT3G14870, |
| AT2G46380, | AT2G46390, | AT2G46455, | AT2G46490, | AT3G14880, | AT3G14900, | AT3G14910, | AT3G14920, |
| AT2G46540, | AT2G46550, | AT2G46640, | AT2G46735, | AT3G15000, | AT3G15095, | AT3G15110, | AT3G15115, |
| AT2G46820, | AT2G46830, | AT2G46915, | AT2G46940, | AT3G15230, | AT3G15240, | AT3G15250, | AT3G15280, |
| AT2G46980, | AT2G47010, | AT2G47020, | AT2G47115, | AT3G15310, | AT3G15340, | AT3G15351, | AT3G15357, |
| AT2G47200, | AT2G47360, | AT2G47480, | AT2G47485, | AT3G15358, | AT3G15395, | AT3G15400, | AT3G15420, |
| AT2G47530, | AT2G47660, | AT2G47690, | AT2G47720, | AT3G15440, | AT3G15550, | AT3G15560, | AT3G15630, |
| AT2G47840, | AT2G47910, | AT2G47930, | AT2G47950, | AT3G15750, | AT3G15760, | AT3G15770, | AT3G15780, |
| AT2G48040, | AT2G48050, | AT2G48060, | AT2G48070, | AT3G15820, | AT3G15830, | AT3G15840, | AT3G15860, |
| AT2G48075, | AT2G48090, | AT2G48120, | AT3G01060, | AT3G15900, | AT3G15910, | AT3G15950, | AT3G16000, |
| AT3G01130, | AT3G01160, | AT3G01170, | AT3G01230, | AT3G16040, | AT3G16070, | AT3G16200, | AT3G16220, |
| AT3G01240, | AT3G01250, | AT3G01323, | AT3G01325, | AT3G16330, | AT3G16660, | AT3G16670, | AT3G16750, |
| AT3G01345, | AT3G01430, | AT3G01435, | AT3G01513, | AT3G16895, | AT3G16930, | AT3G17120, | AT3G17155, |
| AT3G01516, | AT3G01670, | AT3G01680, | AT3G01700, | AT3G17160, | AT3G17190, | AT3G17350, | AT3G17460, |
| AT3G01710, | AT3G01720, | AT3G01730, | AT3G01740, | AT3G17580, | AT3G17780, | AT3G17890, | AT3G17900, |
| AT3G01810, | AT3G01860, | AT3G01940, | AT3G01950, | AT3G17930, | AT3G17950, | AT3G18050, | AT3G18240, |
| AT3G01960, | AT3G02120, | AT3G02125, | AT3G02170, | AT3G18250, | AT3G18300, | AT3G18310, | AT3G18350, |
| AT3G02180, | AT3G02220, | AT3G02240, | AT3G02370, | AT3G18410, | AT3G18485, | AT3G18510, | AT3G18540, |
| AT3G02390, | AT3G02420, | AT3G02500, | AT3G02555, | AT3G18560, | AT3G18700, | AT3G18770, | AT3G18800, |
| AT3G02560, | AT3G02640, | AT3G02670, | AT3G02680, | AT3G18940, | AT3G19020, | AT3G19030, | AT3G19055, |
| AT3G02790, | AT3G02860, | AT3G02900, | AT3G02930, | AT3G19120, | AT3G19180, | AT3G19200, | AT3G19220, |
| AT3G03020, | AT3G03070, | AT3G03130, | AT3G03150, | AT3G19250, | AT3G19330, | AT3G19340, | AT3G19530, |
| AT3G03160, | AT3G03170, | AT3G03210, | AT3G03420, | AT3G19540, | AT3G19550, | AT3G19650, | AT3G19660, |
| AT3G03460, | AT3G03560, | AT3G03570, | AT3G03770, | AT3G19750, | AT3G19790, | AT3G19800, | AT3G19900, |
| AT3G03773, | AT3G03870, | AT3G03930, | AT3G04020, | AT3G19920, | AT3G20070, | AT3G20155, | AT3G20340, |
| AT3G04040, | AT3G04160, | AT3G04310, | AT3G04510, | AT3G20350, | AT3G20362, | AT3G20430, | AT3G20450, |
| AT3G04550, | AT3G04560, | AT3G04640, | AT3G04740, | AT3G20490, | AT3G20555, | AT3G20557, | AT3G20680, |
| AT3G04903, | AT3G04943, | AT3G04945, | AT3G04960, | AT3G20720, | AT3G20760, | AT3G20850, | AT3G20865, |
| AT3G04990, | AT3G05010, | AT3G05020, | AT3G05080, | AT3G20900, | AT3G20920, | AT3G20980, | AT3G21000, |
| AT3G05110, | AT3G05130, | AT3G05220, | AT3G05320, | AT3G21055, | AT3G21080, | AT3G21260, | AT3G21290, |
| AT3G05330, | AT3G05410, | AT3G05460, | AT3G05550, | AT3G21320, | AT3G21400, | AT3G21465, | AT3G21570, |
| AT3G05570, | AT3G05725, | AT3G05727, | AT3G05730, | AT3G21680, | AT3G21710, | AT3G21865, | AT3G22070, |
| AT3G05830, | AT3G05900, | AT3G05935, | AT3G05937, | AT3G22090, | AT3G22210, | AT3G22231, | AT3G22235, |
| AT3G05980, | AT3G06020, | AT3G06070, | AT3G06090, | AT3G22240, | AT3G22270, | AT3G22380, | AT3G22415, |
| AT3G06145, | AT3G06180, | AT3G06360, | AT3G06435, | AT3G22430, | AT3G22510, | AT3G22680, | AT3G22790, |
| AT3G06545, | AT3G06547, | AT3G06600, | AT3G06610, | AT3G22820, | AT3G22840, | AT3G22942, | AT3G23040, |
| AT3G06670, | AT3G06710, | AT3G06750, | AT3G06780, | AT3G23165, | AT3G23167, | AT3G23170, | AT3G23172, |
| AT3G06790, | AT3G06840, | AT3G06870, | AT3G06890, | AT3G23245, | AT3G23290, | AT3G23295, | AT3G23440, |
| AT3G06895, | AT3G06960, | AT3G07005, | AT3G07150, | AT3G23590, | AT3G23650, | AT3G23715, | AT3G23720, |
| AT3G07180, | AT3G07195, | AT3G07210, | AT3G07425, | AT3G23727, | AT3G23740, | AT3G23850, | AT3G23860, |
| AT3G07440, | AT3G07510, | AT3G07560, | AT3G07568, | AT3G23910, | AT3G24160, | AT3G24180, | AT3G24225, |
| AT3G07580, | AT3G07640, | AT3G07710, | AT3G07730, | AT3G24250, | AT3G24255, | AT3G24280, | AT3G24380, |

AT3G24490, AT3G24506, AT3G24508, AT3G24510,
AT3G24513, AT3G24517, AT3G24535, AT3G24630,
AT3G24640, AT3G24680, AT3G24690, AT3G24750,
AT3G24770, AT3G24780, AT3G25080, AT3G25130,
AT3G25200, AT3G25400, AT3G25545, AT3G25590,
AT3G25597, AT3G25640, AT3G25655, AT3G25690,
AT3G25720, AT3G25727, AT3G25805, AT3G25870,
AT3G25882, AT3G25905, AT3G26000, AT3G26110,
AT3G26235, AT3G26616, AT3G26710, AT3G26750,
AT3G26800, AT3G26850, AT3G26855, AT3G26890,
AT3G26910, AT3G26950, AT3G26960, AT3G27025,
AT3G27030, AT3G27050, AT3G27100, AT3G27130,
AT3G27210, AT3G27250, AT3G27350, AT3G27370,
AT3G27390, AT3G27420, AT3G27520, AT3G27590,
AT3G27630, AT3G27750, AT3G27770, AT3G27800,
AT3G27906, AT3G27930, AT3G27990, AT3G28020,
AT3G28110, AT3G28120, AT3G28155, AT3G28220,
AT3G28190, AT3G28240, AT3G28260, AT3G28280,
AT3G28350, AT3G28370, AT3G28420, AT3G28455,
AT3G28530, AT3G28560, AT3G28590, AT3G28670,
AT3G28720, AT3G28770, AT3G29010, AT3G29033,
AT3G29034, AT3G29075, AT3G29080, AT3G29130,
AT3G29140, AT3G29185, AT3G29210, AT3G29220,
AT3G29265, AT3G29280, AT3G29300, AT3G29305,
AT3G29385, AT3G29420, AT3G29450, AT3G29470,
AT3G29560, AT3G29570, AT3G29600, AT3G29610,
AT3G29636, AT3G29700, AT3G29763, AT3G29785,
AT3G29786, AT3G29790, AT3G29796, AT3G30150,
AT3G30160, AT3G30190, AT3G30200, AT3G30220,
AT3G30250, AT3G30320, AT3G30350, AT3G30360,
AT3G30370, AT3G30490, AT3G30510, AT3G30520,
AT3G30580, AT3G30590, AT3G30610, AT3G30645,
AT3G30650, AT3G30660, AT3G30670, AT3G30690,
AT3G30700, AT3G30720, AT3G30725, AT3G30730,
AT3G30750, AT3G30751, AT3G30755, AT3G30816,
AT3G30820, AT3G30840, AT3G30843, AT3G30845,
AT3G30848, AT3G31300, AT3G31310, AT3G31320,
AT3G31330, AT3G31350, AT3G31370, AT3G31400,
AT3G31406, AT3G31430, AT3G31540, AT3G31900,
AT3G31910, AT3G31915, AT3G31940, AT3G31955,
AT3G32050, AT3G32070, AT3G32100, AT3G32120,
AT3G32150, AT3G32160, AT3G32180, AT3G32190,
AT3G32200, AT3G32330, AT3G32410, AT3G32896,
AT3G32902, AT3G32903, AT3G32904, AT3G32930,
AT3G32960, AT3G33064, AT3G33073, AT3G33080,
AT3G33131, AT3G33187, AT3G33230, AT3G33293,
AT3G33393, AT3G33448, AT3G33494, AT3G33572,
AT3G42070, AT3G42090, AT3G42120, AT3G42130,
AT3G42140, AT3G42190, AT3G42200, AT3G42240,
AT3G42250, AT3G42254, AT3G42300, AT3G42310,
AT3G42320, AT3G42350, AT3G42380, AT3G42390,
AT3G42430, AT3G42436, AT3G42473, AT3G42480,
AT3G42490, AT3G42510, AT3G42520, AT3G42540,
AT3G42556, AT3G42560, AT3G42590, AT3G42610,
AT3G42680, AT3G42700, AT3G42723, AT3G42725,
AT3G42740, AT3G42750, AT3G42780, AT3G42786,
AT3G42800, AT3G42810, AT3G42870, AT3G42920,
AT3G42970, AT3G42990, AT3G43110, AT3G43140,
AT3G43150, AT3G43153, AT3G43160, AT3G43260,
AT3G43280, AT3G43290, AT3G43330, AT3G43410,
AT3G43420, AT3G43450, AT3G43470, AT3G43480,
AT3G43500, AT3G43528, AT3G43580, AT3G43583,
AT3G43680, AT3G43682, AT3G43760, AT3G43770,
AT3G43833, AT3G43850, AT3G43863, AT3G43870,
AT3G43880, AT3G43900, AT3G43910, AT3G43930,
AT3G43940, AT3G43970, AT3G44020, AT3G44040,
AT3G44070, AT3G44115, AT3G44140, AT3G44150,
AT3G44170, AT3G44210, AT3G44230, AT3G44235,
AT3G44280, AT3G44370, AT3G44430, AT3G44440,
AT3G44450, AT3G44470, AT3G44570, AT3G44580,
AT3G44690, AT3G44716, AT3G44750, AT3G44755,
AT3G44760, AT3G44770, AT3G44935, AT3G44950,
AT3G44960, AT3G44980, AT3G45040, AT3G45050,
AT3G45093, AT3G45110, AT3G45120, AT3G45160,
AT3G45200, AT3G45230, AT3G45320, AT3G45360,
AT3G45370, AT3G45443, AT3G45577, AT3G45730,
AT3G45755, AT3G45820, AT3G45830, AT3G45900,
AT3G45910, AT3G46150, AT3G46220, AT3G46240,
AT3G46270, AT3G46300, AT3G46310, AT3G46360,
AT3G46380, AT3G46390, AT3G46430, AT3G46630,
AT3G46750, AT3G46880, AT3G46890, AT3G47070,
AT3G47100, AT3G47230, AT3G47240, AT3G47295,
AT3G47320, AT3G47410, AT3G47490, AT3G47510,
AT3G47630, AT3G47675, AT3G47833, AT3G47836,
AT3G47850, AT3G47920, AT3G47965, AT3G48020,
AT3G48120, AT3G48180, AT3G48185, AT3G48200,
AT3G48220, AT3G48231, AT3G48470, AT3G48490,
AT3G48510, AT3G48550, AT3G48630, AT3G48640,
AT3G48660, AT3G48675, AT3G48710, AT3G48860,
AT3G49055, AT3G49230, AT3G49250, AT3G49270,
AT3G49280, AT3G49290, AT3G49300, AT3G49305,
AT3G49307, AT3G49410, AT3G49460, AT3G49490,
AT3G49540, AT3G49550, AT3G49570, AT3G49580,
AT3G49590, AT3G49770, AT3G49790, AT3G49820,
AT3G49840, AT3G49890, AT3G49990, AT3G50040,
AT3G50250, AT3G50320, AT3G50340, AT3G50370,
AT3G50373, AT3G50376, AT3G50430, AT3G50540,
AT3G50550, AT3G50570, AT3G50580, AT3G50610,
AT3G50640, AT3G50685, AT3G50800, AT3G50900,
AT3G50910, AT3G50925, AT3G51010, AT3G51100,
AT3G51230, AT3G51290, AT3G51350, AT3G51500,
AT3G51510, AT3G51540, AT3G51580, AT3G51610,
AT3G51640, AT3G51650, AT3G51750, AT3G51890,
AT3G51970, AT3G52040, AT3G52070, AT3G52105,
AT3G52110, AT3G52115, AT3G52170, AT3G52220,
AT3G52230, AT3G52240, AT3G52360, AT3G52420,
AT3G52480, AT3G52520, AT3G52540, AT3G52550,
AT3G52620, AT3G52700, AT3G52710, AT3G52740,
AT3G52770, AT3G52860, AT3G53235, AT3G53270,
AT3G53320, AT3G53350, AT3G53470, AT3G53540,
AT3G53630, AT3G53670, AT3G53860, AT3G53970,
AT3G54000, AT3G54060, AT3G54170, AT3G54310,
AT3G54500, AT3G54520, AT3G54530, AT3G54630,
AT3G54680, AT3G54710, AT3G54730, AT3G54750,
AT3G54880, AT3G55060, AT3G55160, AT3G55250,
AT3G55420, AT3G55570, AT3G55600, AT3G55646,
AT3G55690, AT3G55720, AT3G55760, AT3G55790,
AT3G55860, AT3G55880, AT3G55910, AT3G55930,
AT3G56010, AT3G56160, AT3G56220, AT3G56250,
AT3G56260, AT3G56290, AT3G56360, AT3G56390,
AT3G56410, AT3G56430, AT3G56480, AT3G56500,
AT3G56590, AT3G56610, AT3G56650, AT3G56670,
AT3G56720, AT3G56750, AT3G56790, AT3G56870,
AT3G56910, AT3G57110, AT3G57160, AT3G57200,
AT3G57210, AT3G57320, AT3G57360, AT3G57400,
AT3G57420, AT3G57440, AT3G57450, AT3G57500,
AT3G57690, AT3G57780, AT3G57785, AT3G57850,
AT3G57860, AT3G57930, AT3G57950, AT3G57990,
AT3G58010, AT3G58020, AT3G58050, AT3G58080,
AT3G58110, AT3G58230, AT3G58280, AT3G58300,
AT3G58320, AT3G58330, AT3G58470, AT3G58480,
AT3G58540, AT3G58770, AT3G58840, AT3G58870,
AT3G59090, AT3G59300, AT3G59370, AT3G59390,
AT3G59430, AT3G59460, AT3G59490, AT3G59640,
AT3G59680, AT3G59800, AT3G59840, AT3G59870,
AT3G59880, AT3G59900, AT3G59930, AT3G60070,
AT3G60200, AT3G60230, AT3G60310, AT3G60320,
AT3G60380, AT3G60480, AT3G60520, AT3G60560,
AT3G60590, AT3G60650, AT3G60680, AT3G60760,
AT3G60850, AT3G60890, AT3G60930, AT3G61370,

AT3G61380, AT3G61500, AT3G61570, AT3G61660, AT3G61670, AT3G61710, AT3G61780, AT3G61840, AT3G61870, AT3G61898, AT3G61920, AT3G61930, AT3G62070, AT3G62140, AT3G62320, AT3G62350, AT3G62370, AT3G62380, AT3G62400, AT3G62450, AT3G62480, AT3G62490, AT3G62500, AT3G62510, AT3G62580, AT3G62640, AT3G62650, AT3G62680, AT3G62730, AT3G62790, AT3G62920, AT3G62990, AT3G63020, AT3G63040, AT3G63050, AT3G63100, AT3G63160, AT3G63180, AT3G63270, AT3G63420, AT3G63430, AT4G00280, AT4G00310, AT4G00355, AT4G00440, AT4G00450, AT4G00525, AT4G00530, AT4G00580, AT4G00585, AT4G00695, AT4G00770, AT4G00890, AT4G00920, AT4G00930, AT4G00950, AT4G00955, AT4G01090, AT4G01150, AT4G01170, AT4G01245, AT4G01290, AT4G01340, AT4G01360, AT4G01500, AT4G01525, AT4G01530, AT4G01535, AT4G01590, AT4G01670, AT4G01735, AT4G01895, AT4G01915, AT4G01935, AT4G01960, AT4G01985, AT4G01995, AT4G02000, AT4G02030, AT4G02040, AT4G02090, AT4G02140, AT4G02160, AT4G02170, AT4G02210, AT4G02270, AT4G02425, AT4G02465, AT4G02482, AT4G02530, AT4G02550, AT4G02715, AT4G02725, AT4G02760, AT4G02800, AT4G02810, AT4G02830, AT4G02870, AT4G02880, AT4G02920, AT4G03090, AT4G03150, AT4G03165, AT4G03180, AT4G03305, AT4G03380, AT4G03505, AT4G03580, AT4G03600, AT4G03620, AT4G03680, AT4G03740, AT4G03750, AT4G03820, AT4G03940, AT4G03970, AT4G03975, AT4G03979, AT4G04030, AT4G04155, AT4G04190, AT4G04273, AT4G04330, AT4G04394, AT4G04396, AT4G04398, AT4G04423, AT4G04470, AT4G04480, AT4G04525, AT4G04614, AT4G04635, AT4G04650, AT4G04730, AT4G04745, AT4G04820, AT4G04925, AT4G04980, AT4G05070, AT4G05095, AT4G05145, AT4G05290, AT4G05370, AT4G05400, AT4G05523, AT4G05553, AT4G05560, AT4G05580, AT4G05581, AT4G05616, AT4G05631, AT4G05632, AT4G05636, AT4G05640, AT4G06490, AT4G06534, AT4G06603, AT4G06637, AT4G06672, AT4G06676, AT4G06716, AT4G06724, AT4G06728, AT4G06735, AT4G06740, AT4G07380, AT4G07452, AT4G07460, AT4G07485, AT4G07500, AT4G07515, AT4G07523, AT4G07524, AT4G07526, AT4G07666, AT4G07675, AT4G07740, AT4G07800, AT4G07825, AT4G07868, AT4G07932, AT4G07940, AT4G07943, AT4G07965, AT4G08013, AT4G08025, AT4G08028, AT4G08039, AT4G08056, AT4G08097, AT4G08098, AT4G08111, AT4G08130, AT4G08140, AT4G08200, AT4G08230, AT4G08240, AT4G08270, AT4G08310, AT4G08330, AT4G08336, AT4G08395, AT4G08485, AT4G08510, AT4G08540, AT4G08555, AT4G08593, AT4G08602, AT4G08630, AT4G08710, AT4G08730, AT4G08740, AT4G08760, AT4G08810, AT4G08820, AT4G08868, AT4G08869, AT4G08874, AT4G08875, AT4G08876, AT4G08895, AT4G08910, AT4G09030, AT4G09060, AT4G09070, AT4G09153, AT4G09170, AT4G09210, AT4G09220, AT4G09260, AT4G09270, AT4G09290, AT4G09390, AT4G09550, AT4G09580, AT4G09630, AT4G09647, AT4G09680, AT4G09700, AT4G09840, AT4G09850, AT4G09860, AT4G09880, AT4G09890, AT4G09965, AT4G09970, AT4G09984, AT4G10060, AT4G10080, AT4G10090, AT4G10140, AT4G10180, AT4G10230, AT4G10265, AT4G10270, AT4G10330, AT4G10613, AT4G10660, AT4G10670, AT4G10700, AT4G10800, AT4G10810, AT4G10820, AT4G10845, AT4G10860, AT4G10870, AT4G10890, AT4G10910, AT4G10930, AT4G10970, AT4G11020, AT4G11100, AT4G11211, AT4G11385, AT4G11393, AT4G11430, AT4G11700, AT4G11720, AT4G11780, AT4G11870, AT4G11910, AT4G11940, AT4G11990, AT4G12000, AT4G12005, AT4G12070, AT4G12220, AT4G12350, AT4G12370, AT4G12380, AT4G12540, AT4G12580, AT4G12680, AT4G12700, AT4G12735, AT4G12760, AT4G12770, AT4G12780, AT4G12930, AT4G12940, AT4G12970, AT4G12990, AT4G13095, AT4G13140, AT4G13150, AT4G13195, AT4G13200, AT4G13220, AT4G13235, AT4G13266, AT4G13270, AT4G13320, AT4G13340, AT4G13470, AT4G13500, AT4G13520, AT4G13530, AT4G13540, AT4G13690, AT4G13740, AT4G13955, AT4G13968, AT4G14100, AT4G14104, AT4G14120, AT4G14200, AT4G14270, AT4G14272, AT4G14276, AT4G14315, AT4G14380, AT4G14385, AT4G14450, AT4G14530, AT4G14590, AT4G14615, AT4G14650, AT4G14690, AT4G14723, AT4G14760, AT4G14810, AT4G14950, AT4G14970, AT4G14990, AT4G15030, AT4G15096, AT4G15140, AT4G15150, AT4G15160, AT4G15460, AT4G15540, AT4G15563, AT4G15640, AT4G15650, AT4G15710, AT4G15733, AT4G15735, AT4G15820, AT4G15885, AT4G15950, AT4G15970, AT4G15990, AT4G16000, AT4G16040, AT4G16060, AT4G16090, AT4G16140, AT4G16170, AT4G16215, AT4G16240, AT4G16320, AT4G16400, AT4G16444, AT4G16447, AT4G16450, AT4G16460, AT4G16515, AT4G16695, AT4G16810, AT4G16840, AT4G16845, AT4G16850, AT4G16980, AT4G17000, AT4G17030, AT4G17080, AT4G17110, AT4G17130, AT4G17215, AT4G17240, AT4G17250, AT4G17310, AT4G17430, AT4G17540, AT4G17590, AT4G17600, AT4G17620, AT4G17700, AT4G17713, AT4G17790, AT4G17930, AT4G17960, AT4G17990, AT4G18000, AT4G18070, AT4G18080, AT4G18090, AT4G18140, AT4G18280, AT4G18310, AT4G18320, AT4G18335, AT4G18395, AT4G18400, AT4G18420, AT4G18470, AT4G18490, AT4G18500, AT4G18501, AT4G18510, AT4G18540, AT4G18570, AT4G18580, AT4G18593, AT4G18600, AT4G18610, AT4G18650, AT4G18660, AT4G18670, AT4G18680, AT4G18690, AT4G18823, AT4G18830, AT4G18850, AT4G18860, AT4G19070, AT4G19095, AT4G19100, AT4G19140, AT4G19160, AT4G19190, AT4G19200, AT4G19240, AT4G19270, AT4G19280, AT4G19290, AT4G19305, AT4G19320, AT4G19350, AT4G19360, AT4G19430, AT4G19480, AT4G19620, AT4G19905, AT4G19950, AT4G19980, AT4G20020, AT4G20095, AT4G20150, AT4G20160, AT4G20190, AT4G20250, AT4G20290, AT4G20330, AT4G20350, AT4G20390, AT4G20470, AT4G20500, AT4G20510, AT4G20690, AT4G20715, AT4G20720, AT4G20880, AT4G21010, AT4G21105, AT4G21140, AT4G21215, AT4G21445, AT4G21460, AT4G21500, AT4G21620, AT4G21700, AT4G21720, AT4G21740, AT4G21780, AT4G21865, AT4G21890, AT4G21920, AT4G21950, AT4G22000, AT4G22160, AT4G22190, AT4G22210, AT4G22214, AT4G22217, AT4G22235, AT4G22270, AT4G22320, AT4G22400, AT4G22420, AT4G22430, AT4G22440, AT4G22470, AT4G22510, AT4G22600, AT4G22740, AT4G22800, AT4G22830, AT4G22850, AT4G22860, AT4G22920, AT4G22980, AT4G23020, AT4G23090, AT4G23110, AT4G23330, AT4G23493, AT4G23496, AT4G23610, AT4G23760, AT4G23770, AT4G23780, AT4G23870, AT4G23880, AT4G23885, AT4G23890, AT4G23910, AT4G23970, AT4G23980, AT4G24030, AT4G24110, AT4G24150, AT4G24175, AT4G24265, AT4G24275, AT4G24300, AT4G24370, AT4G24410, AT4G24500, AT4G24590, AT4G24600, AT4G24610, AT4G24680, AT4G24700, AT4G24720, AT4G24900, AT4G24930, AT4G24950, AT4G24972, AT4G24980, AT4G25030, AT4G25070, AT4G25170, AT4G25315, AT4G25430, AT4G25510, AT4G25515, AT4G25520, AT4G25620, AT4G25670, AT4G25690,

AT4G25760, AT4G25845, AT4G26020, AT4G26030, AT5G01840, AT5G01881, AT5G01910, AT5G01970,
AT4G26040, AT4G26060, AT4G26130, AT4G26170, AT5G02000, AT5G02020, AT5G02090, AT5G02120,
AT4G26190, AT4G26240, AT4G26290, AT4G26320, AT5G02160, AT5G02200, AT5G02220, AT5G02390,
AT4G26410, AT4G26450, AT4G26630, AT4G26850, AT5G02420, AT5G02440, AT5G02502, AT5G02510,
AT4G26960, AT4G26965, AT4G27020, AT4G27030, AT5G02520, AT5G02550, AT5G02640, AT5G02650,
AT4G27120, AT4G27330, AT4G27380, AT4G27390, AT5G02660, AT5G02680, AT5G02690, AT5G02720,
AT4G27410, AT4G27415, AT4G27430, AT4G27500, AT5G02740, AT5G02770, AT5G02850, AT5G03050,
AT4G27510, AT4G27530, AT4G27580, AT4G27595, AT5G03060, AT5G03090, AT5G03110, AT5G03120,
AT4G27610, AT4G27630, AT4G27652, AT4G27654, AT5G03130, AT5G03210, AT5G03345, AT5G03400,
AT4G27657, AT4G27660, AT4G27810, AT4G27850, AT5G03420, AT5G03440, AT5G03460, AT5G03545,
AT4G27930, AT4G27980, AT4G28005, AT4G28025, AT5G03550, AT5G03560, AT5G03670, AT5G03710,
AT4G28085, AT4G28100, AT4G28160, AT4G28170, AT5G03740, AT5G03750, AT5G03830, AT5G03890,
AT4G28180, AT4G28190, AT4G28210, AT4G28230, AT5G03900, AT5G03920, AT5G03930, AT5G03950,
AT4G28240, AT4G28260, AT4G28280, AT4G28290, AT5G03990, AT5G04000, AT5G04030, AT5G04045,
AT4G28310, AT4G28330, AT4G28340, AT4G28460, AT5G04080, AT5G04090, AT5G04190, AT5G04290,
AT4G28690, AT4G28740, AT4G28760, AT4G28770, AT5G04470, AT5G04520, AT5G04650, AT5G04670,
AT4G28810, AT4G28840, AT4G28870, AT4G28920, AT5G04730, AT5G04750, AT5G04790, AT5G04840,
AT4G28930, AT4G29020, AT4G29030, AT4G29200, AT5G04860, AT5G04910, AT5G05020, AT5G05180,
AT4G29273, AT4G29280, AT4G29285, AT4G29290, AT5G05190, AT5G05220, AT5G05240, AT5G05250,
AT4G29300, AT4G29305, AT4G29520, AT4G29560, AT5G05300, AT5G05310, AT5G05360, AT5G05480,
AT4G29660, AT4G29780, AT4G29790, AT4G29870, AT5G05640, AT5G05660, AT5G05800, AT5G05840,
AT4G29960, AT4G30010, AT4G30050, AT4G30064, AT5G05930, AT5G05950, AT5G05965, AT5G06010,
AT4G30070, AT4G30074, AT4G30090, AT4G30130, AT5G06043, AT5G06190, AT5G06240, AT5G06265,
AT4G30150, AT4G30230, AT4G30390, AT4G30450, AT5G06270, AT5G06280, AT5G06380, AT5G06590,
AT4G30460, AT4G30630, AT4G30662, AT4G30670, AT5G06610, AT5G06710, AT5G06790, AT5G06890,
AT4G30730, AT4G30740, AT4G30750, AT4G30770, AT5G06930, AT5G06980, AT5G06990, AT5G07020,
AT4G30780, AT4G30790, AT4G30993, AT5G07170, AT5G07330, AT5G07380, AT5G07490,
AT4G31030, AT4G31080, AT4G31090, AT4G31115, AT5G07570, AT5G07730, AT5G07790, AT5G07890,
AT4G31260, AT4G31280, AT4G31340, AT4G31380, AT5G07940, AT5G07950, AT5G07970, AT5G07980,
AT4G31430, AT4G31440, AT4G31510, AT4G31550, AT5G08010, AT5G08040, AT5G08055, AT5G08060,
AT4G31560, AT4G31570, AT4G31600, AT4G31730, AT5G08090, AT5G08120, AT5G08150, AT5G08185,
AT4G31805, AT4G31830, AT4G31875, AT4G31880, AT5G08210, AT5G08220, AT5G08240, AT5G08270,
AT4G31960, AT4G32020, AT4G32030, AT4G32080, AT5G08315, AT5G08320, AT5G08400, AT5G08450,
AT4G32090, AT4G32100, AT4G32105, AT4G32110, AT5G08505, AT5G08540, AT5G08770, AT5G09225,
AT4G32190, AT4G32230, AT4G32240, AT4G32460, AT5G09270, AT5G09310, AT5G09390, AT5G09480,
AT4G32560, AT4G32590, AT4G32680, AT4G32695, AT5G09520, AT5G09530, AT5G09670, AT5G09860,
AT4G32770, AT4G32860, AT4G32960, AT4G32970, AT5G09960, AT5G09980, AT5G09990, AT5G09995,
AT4G33130, AT4G33310, AT4G33320, AT4G33380, AT5G10010, AT5G10040, AT5G10110, AT5G10310,
AT4G33480, AT4G33560, AT4G33590, AT4G33600, AT5G10320, AT5G10430, AT5G10590, AT5G10660,
AT4G33610, AT4G33625, AT4G33640, AT4G33660, AT5G10670, AT5G10680, AT5G10700, AT5G10710,
AT4G33666, AT4G33690, AT4G33740, AT4G33750, AT5G10745, AT5G10850, AT5G10890, AT5G10950,
AT4G33780, AT4G33800, AT4G33890, AT4G33925, AT5G11030, AT5G11070, AT5G11090, AT5G11120,
AT4G33960, AT4G33970, AT4G33980, AT4G34080, AT5G11220, AT5G11280, AT5G11390, AT5G11420,
AT4G34090, AT4G34190, AT4G34265, AT4G34412, AT5G11530, AT5G11600, AT5G11630, AT5G11680,
AT4G34550, AT4G34560, AT4G34600, AT4G34630, AT5G11760, AT5G11780, AT5G11810, AT5G11830,
AT4G34690, AT4G35170, AT4G35240, AT4G35295, AT5G11870, AT5G11970, AT5G11990, AT5G12010,
AT4G35360, AT4G35400, AT4G35430, AT4G35510, AT5G12050, AT5G12160, AT5G12170, AT5G12230,
AT4G35530, AT4G35725, AT4G35940, AT4G35980, AT5G12235, AT5G12240, AT5G12290, AT5G12340,
AT4G35987, AT4G36100, AT4G36105, AT4G36170, AT5G12360, AT5G12430, AT5G12470, AT5G12880,
AT4G36370, AT4G36440, AT4G36460, AT4G36500, AT5G12930, AT5G12990, AT5G13090, AT5G13240,
AT4G36510, AT4G36515, AT4G36520, AT4G36560, AT5G13250, AT5G13260, AT5G13310, AT5G13340,
AT4G36830, AT4G36925, AT4G36980, AT4G37030, AT5G13390, AT5G13470, AT5G13500, AT5G13540,
AT4G37090, AT4G37110, AT4G37130, AT4G37240, AT5G13560, AT5G13590, AT5G13610, AT5G13620,
AT4G37290, AT4G37295, AT4G37300, AT4G37440, AT5G13655, AT5G13660, AT5G13825, AT5G13880,
AT4G37445, AT4G37450, AT4G37685, AT4G37700, AT5G13940, AT5G13950, AT5G13970, AT5G14020,
AT4G37740, AT4G37810, AT4G37820, AT4G37920, AT5G14090, AT5G14105, AT5G14110, AT5G14150,
AT4G37925, AT4G38060, AT4G38070, AT4G38080, AT5G14210, AT5G14290, AT5G14330, AT5G14380,
AT4G38100, AT4G38120, AT4G38225, AT4G38280, AT5G14410, AT5G14560, AT5G14690, AT5G14710,
AT4G38330, AT4G38490, AT4G38500, AT4G38680, AT5G14730, AT5G14920, AT5G14930, AT5G14970,
AT4G38750, AT4G38760, AT4G38820, AT4G38980, AT5G14990, AT5G15000, AT5G15190, AT5G15260,
AT4G39190, AT4G39235, AT4G39300, AT4G39320, AT5G15320, AT5G15360, AT5G15420, AT5G15560,
AT4G39360, AT4G39380, AT4G39403, AT4G39420, AT5G15600, AT5G15725, AT5G15780, AT5G15802,
AT4G39430, AT4G39440, AT4G39450, AT4G39610, AT5G15960, AT5G15970, AT5G15990, AT5G16030,
AT4G39630, AT4G39670, AT4G39675, AT4G39690, AT5G16060, AT5G16100, AT5G16110, AT5G16160,
AT4G39745, AT4G39750, AT4G39790, AT4G39840, AT5G16200, AT5G16250, AT5G16453, AT5G16470,
AT4G39860, AT4G39900, AT4G39917, AT4G39920, AT5G16486, AT5G16520, AT5G16550, AT5G16610,
AT4G39930, AT4G40020, AT4G40045, AT4G40090, AT5G16660, AT5G16730, AT5G16940, AT5G16950,
AT5G01015, AT5G01030, AT5G01075, AT5G01080, AT5G17070, AT5G17130, AT5G17160, AT5G17190,
AT5G01225, AT5G01280, AT5G01350, AT5G01370, AT5G17280, AT5G17340, AT5G17360, AT5G17460,
AT5G01570, AT5G01690, AT5G01730, AT5G01790, AT5G17510, AT5G17520, AT5G17590, AT5G17610,

AT5G17650, AT5G17870, AT5G17910, AT5G18130,
AT5G18150, AT5G18250, AT5G18310, AT5G18403,
AT5G18407, AT5G18420, AT5G18440, AT5G18540,
AT5G18636, AT5G18690, AT5G18710, AT5G18720,
AT5G18730, AT5G18740, AT5G18850, AT5G18880,
AT5G19070, AT5G19172, AT5G19190, AT5G19230,
AT5G19260, AT5G19315, AT5G19340, AT5G19480,
AT5G19540, AT5G19570, AT5G19710, AT5G19800,
AT5G19810, AT5G19875, AT5G19900, AT5G19950,
AT5G19970, AT5G19980, AT5G20045, AT5G20100,
AT5G20120, AT5G20130, AT5G20170, AT5G20200,
AT5G20370, AT5G20450, AT5G20460, AT5G20610,
AT5G20635, AT5G20760, AT5G20770, AT5G20790,
AT5G20820, AT5G20935, AT5G21020, AT5G21050,
AT5G21070, AT5G21080, AT5G21110, AT5G21125,
AT5G21280, AT5G21910, AT5G21940, AT5G22040,
AT5G22090, AT5G22120, AT5G22150, AT5G22160,
AT5G22170, AT5G22180, AT5G22190, AT5G22210,
AT5G22270, AT5G22280, AT5G22310, AT5G22340,
AT5G22390, AT5G22430, AT5G22450, AT5G22520,
AT5G22530, AT5G22545, AT5G22555, AT5G22650,
AT5G22680, AT5G22790, AT5G22875, AT5G22970,
AT5G23035, AT5G23100, AT5G23110, AT5G23160,
AT5G23180, AT5G23200, AT5G23212, AT5G23390,
AT5G23410, AT5G23460, AT5G23490, AT5G23510,
AT5G23610, AT5G23640, AT5G23700, AT5G23890,
AT5G23920, AT5G24060, AT5G24130, AT5G24165,
AT5G24250, AT5G24310, AT5G24313, AT5G24314,
AT5G24316, AT5G24355, AT5G24450, AT5G24480,
AT5G24500, AT5G24570, AT5G24590, AT5G24610,
AT5G24630, AT5G24640, AT5G24655, AT5G24690,
AT5G24740, AT5G24860, AT5G24880, AT5G24890,
AT5G24920, AT5G24980, AT5G25000, AT5G25070,
AT5G25200, AT5G25210, AT5G25240, AT5G25250,
AT5G25260, AT5G25265, AT5G25270, AT5G25280,
AT5G25360, AT5G25425, AT5G25460, AT5G25500,
AT5G25570, AT5G25580, AT5G25590, AT5G25600,
AT5G25750, AT5G25754, AT5G25757, AT5G25870,
AT5G25920, AT5G26020, AT5G26070, AT5G26080,
AT5G26100, AT5G26160, AT5G26230, AT5G26270,
AT5G26350, AT5G26620, AT5G26622, AT5G26640,
AT5G26650, AT5G26692, AT5G26717, AT5G26720,
AT5G26731, AT5G26760, AT5G26770, AT5G26790,
AT5G26800, AT5G26805, AT5G26820, AT5G26840,
AT5G26850, AT5G26890, AT5G26970, AT5G27020,
AT5G27170, AT5G27180, AT5G27210, AT5G27260,
AT5G27290, AT5G27330, AT5G27340, AT5G27440,
AT5G27500, AT5G27590, AT5G27606, AT5G27710,
AT5G27730, AT5G27760, AT5G27800, AT5G27860,
AT5G27890, AT5G27940, AT5G27990, AT5G28070,
AT5G28090, AT5G28110, AT5G28120, AT5G28130,
AT5G28140, AT5G28170, AT5G28190, AT5G28240,
AT5G28270, AT5G28295, AT5G28320, AT5G28400,
AT5G28410, AT5G28420, AT5G28430, AT5G28440,
AT5G28463, AT5G28480, AT5G28482, AT5G28484,
AT5G28490, AT5G28500, AT5G28550, AT5G28560,
AT5G28600, AT5G28610, AT5G28615, AT5G28620,
AT5G28623, AT5G28630, AT5G28720, AT5G28730,
AT5G28785, AT5G28790, AT5G28800, AT5G28810,
AT5G28820, AT5G28823, AT5G28860, AT5G28910,
AT5G28920, AT5G28950, AT5G28960, AT5G28990,
AT5G29020, AT5G29050, AT5G29070, AT5G29090,
AT5G29210, AT5G29576, AT5G29602, AT5G29613,
AT5G30341, AT5G30495, AT5G30520, AT5G31685,
AT5G31752, AT5G31753, AT5G31787, AT5G31838,
AT5G31873, AT5G32161, AT5G32169, AT5G32312,
AT5G32405, AT5G32410, AT5G32590, AT5G32600,
AT5G32605, AT5G32610, AT5G32619, AT5G32621,
AT5G32775, AT5G33230, AT5G33300, AT5G33303,
AT5G33355, AT5G33380, AT5G33390, AT5G33393,
AT5G33715, AT5G33806, AT5G33898, AT5G34358,
AT5G34450, AT5G34540, AT5G34581, AT5G34820,
AT5G34830, AT5G34838, AT5G34860, AT5G34881,
AT5G34883, AT5G34887, AT5G34905, AT5G34910,
AT5G34970, AT5G34980, AT5G35010, AT5G35020,
AT5G35035, AT5G35080, AT5G35090, AT5G35110,
AT5G35120, AT5G35195, AT5G35230, AT5G35270,
AT5G35290, AT5G35300, AT5G35320, AT5G35460,
AT5G35470, AT5G35475, AT5G35480, AT5G35490,
AT5G35510, AT5G35540, AT5G35603, AT5G35604,
AT5G35646, AT5G35695, AT5G35732, AT5G35737,
AT5G35753, AT5G35760, AT5G35792, AT5G35870,
AT5G35880, AT5G35890, AT5G35945, AT5G36001,
AT5G36020, AT5G36035, AT5G36040, AT5G36060,
AT5G36070, AT5G36080, AT5G36100, AT5G36190,
AT5G36228, AT5G36280, AT5G36650, AT5G36690,
AT5G36710, AT5G36720, AT5G36735, AT5G36780,
AT5G36800, AT5G36810, AT5G36900, AT5G36920,
AT5G36925, AT5G36960, AT5G37010, AT5G37050,
AT5G37120, AT5G37190, AT5G37240, AT5G37360,
AT5G37385, AT5G37473, AT5G37474, AT5G37475,
AT5G37478, AT5G37480, AT5G37550, AT5G37730,
AT5G37840, AT5G37880, AT5G38050, AT5G38060,
AT5G38080, AT5G38090, AT5G38190, AT5G38300,
AT5G38310, AT5G38317, AT5G38320, AT5G38330,
AT5G38380, AT5G38400, AT5G38595, AT5G38660,
AT5G38720, AT5G38750, AT5G38770, AT5G38790,
AT5G38880, AT5G38980, AT5G39140, AT5G39170,
AT5G39200, AT5G39205, AT5G39210, AT5G39240,
AT5G39365, AT5G39520, AT5G39530, AT5G39570,
AT5G39600, AT5G39790, AT5G39800, AT5G39880,
AT5G40070, AT5G40080, AT5G40110, AT5G40155,
AT5G40180, AT5G40450, AT5G40460, AT5G40500,
AT5G40520, AT5G40595, AT5G40600, AT5G40620,
AT5G40640, AT5G40690, AT5G40700, AT5G40710,
AT5G40730, AT5G40740, AT5G40800, AT5G40855,
AT5G40900, AT5G40960, AT5G40970, AT5G40980,
AT5G41020, AT5G41100, AT5G41110, AT5G41140,
AT5G41190, AT5G41270, AT5G41320, AT5G41505,
AT5G41560, AT5G41620, AT5G41640, AT5G41660,
AT5G41780, AT5G41790, AT5G41810, AT5G41860,
AT5G41910, AT5G41960, AT5G41980, AT5G42030,
AT5G42060, AT5G42070, AT5G42110, AT5G42146,
AT5G42223, AT5G42232, AT5G42235, AT5G42242,
AT5G42290, AT5G42330, AT5G42530, AT5G42635,
AT5G42660, AT5G42710, AT5G42750, AT5G42765,
AT5G42780, AT5G42785, AT5G42797, AT5G42825,
AT5G42900, AT5G42920, AT5G42955, AT5G42957,
AT5G42960, AT5G43000, AT5G43070, AT5G43150,
AT5G43185, AT5G43230, AT5G43260, AT5G43285,
AT5G43310, AT5G43401, AT5G43405, AT5G43480,
AT5G43490, AT5G43510, AT5G43513, AT5G43720,
AT5G43750, AT5G43770, AT5G43880, AT5G43970,
AT5G44005, AT5G44010, AT5G44040, AT5G44060,
AT5G44150, AT5G44313, AT5G44350, AT5G44565,
AT5G44570, AT5G44575, AT5G44580, AT5G44650,
AT5G44660, AT5G44780, AT5G44820, AT5G44860,
AT5G44880, AT5G44973, AT5G45113, AT5G45330,
AT5G45350, AT5G45410, AT5G45460, AT5G45573,
AT5G45660, AT5G45710, AT5G45740, AT5G45830,
AT5G46020, AT5G46115, AT5G46120, AT5G46220,
AT5G46295, AT5G46300, AT5G46310, AT5G46320,
AT5G46440, AT5G46500, AT5G46620, AT5G46730,
AT5G46770, AT5G46795, AT5G46871, AT5G46873,
AT5G46874, AT5G46877, AT5G47090, AT5G47110,
AT5G47170, AT5G47400, AT5G47410, AT5G47455,
AT5G47480, AT5G47490, AT5G47570, AT5G47580,
AT5G47635, AT5G47830, AT5G47870, AT5G47920,
AT5G47940, AT5G48080, AT5G48175, AT5G48200,
AT5G48205, AT5G48210, AT5G48280, AT5G48310,

AT5G48335, AT5G48340, AT5G48420, AT5G48470, AT5G48500, AT5G48515, AT5G48520, AT5G48530, AT5G48595, AT5G48605, AT5G48610, AT5G48657, AT5G48720, AT5G48790, AT5G48830, AT5G48860, AT5G48920, AT5G48953, AT5G49015, AT5G49090, AT5G49100, AT5G49110, AT5G49170, AT5G49210, AT5G49250, AT5G49260, AT5G49280, AT5G49380, AT5G49400, AT5G49410, AT5G49440, AT5G49525, AT5G49550, AT5G49590, AT5G49640, AT5G49670, AT5G49680, AT5G49710, AT5G49790, AT5G49830, AT5G49900, AT5G50090, AT5G50175, AT5G50190, AT5G50200, AT5G50290, AT5G50335, AT5G50350, AT5G50360, AT5G50375, AT5G50410, AT5G50420, AT5G50500, AT5G50540, AT5G50560, AT5G50565, AT5G50610, AT5G50645, AT5G50660, AT5G50665, AT5G50710, AT5G50830, AT5G50840, AT5G50880, AT5G50910, AT5G51090, AT5G51105, AT5G51170, AT5G51195, AT5G51200, AT5G51230, AT5G51330, AT5G51390, AT5G51420, AT5G51430, AT5G51510, AT5G51530, AT5G51545, AT5G51580, AT5G51650, AT5G51680, AT5G51840, AT5G51845, AT5G51850, AT5G51960, AT5G52065, AT5G52080, AT5G52110, AT5G52130, AT5G52140, AT5G52200, AT5G52220, AT5G52280, AT5G52290, AT5G52310, AT5G52410, AT5G52420, AT5G52430, AT5G52500, AT5G52530, AT5G52547, AT5G52550, AT5G52580, AT5G52605, AT5G52780, AT5G52800, AT5G52870, AT5G52890, AT5G52900, AT5G52950, AT5G52960, AT5G52965, AT5G52970, AT5G52975, AT5G52980, AT5G53020, AT5G53030, AT5G53045, AT5G53110, AT5G53220, AT5G53280, AT5G53410, AT5G53440, AT5G53620, AT5G53650, AT5G53660, AT5G53670, AT5G53690, AT5G53710, AT5G53740, AT5G53800, AT5G53860, AT5G53880, AT5G53895, AT5G53900, AT5G53905, AT5G53930, AT5G53960, AT5G54062, AT5G54067, AT5G54095, AT5G54145, AT5G54150, AT5G54215, AT5G54350, AT5G54410, AT5G54440, AT5G54460, AT5G54480, AT5G54540, AT5G54585, AT5G54790, AT5G54850, AT5G54870, AT5G54930, AT5G54950, AT5G54970, AT5G55010, AT5G55030, AT5G55060, AT5G55120, AT5G55131, AT5G55132, AT5G55135, AT5G55210, AT5G55330, AT5G55340, AT5G55350, AT5G55360, AT5G55370, AT5G55420, AT5G55430, AT5G55490, AT5G55500, AT5G55507, AT5G55610, AT5G55620, AT5G55640, AT5G55650, AT5G55660, AT5G55680, AT5G55710, AT5G55750, AT5G55790, AT5G55820, AT5G55870, AT5G55893, AT5G55980, AT5G56070, AT5G56075, AT5G56100, AT5G56120, AT5G56170, AT5G56210, AT5G56240, AT5G56250, AT5G56368, AT5G56369, AT5G56520, AT5G56540, AT5G56550, AT5G56770, AT5G56780, AT5G56795, AT5G56850, AT5G56880, AT5G57000, AT5G57060, AT5G57070, AT5G57080, AT5G57180, AT5G57310, AT5G57340, AT5G57345, AT5G57370, AT5G57400, AT5G57410, AT5G57420, AT5G57460, AT5G57500, AT5G57510, AT5G57650, AT5G57685, AT5G57730, AT5G57760, AT5G57790, AT5G57880, AT5G57887, AT5G57910, AT5G58100, AT5G58110, AT5G58210, AT5G58250, AT5G58260, AT5G58360, AT5G58375, AT5G58470, AT5G58500, AT5G58510, AT5G58570, AT5G58630, AT5G58650, AT5G58790, AT5G58880, AT5G58920, AT5G58960, AT5G59050, AT5G59060, AT5G59080, AT5G59105, AT5G59110, AT5G59170, AT5G59210, AT5G59305, AT5G59330, AT5G59350, AT5G59360, AT5G59460, AT5G59500, AT5G59613, AT5G59616, AT5G59830, AT5G59960, AT5G60000, AT5G60030, AT5G60150, AT5G60210, AT5G60240, AT5G60260, AT5G60290, AT5G60330, AT5G60350, AT5G60400, AT5G60430, AT5G60553, AT5G60630, AT5G60650, AT5G60805, AT5G60810, AT5G60840, AT5G60880, AT5G61040, AT5G61090, AT5G61110, AT5G61120, AT5G61200, AT5G61300, AT5G61340, AT5G61360, AT5G61490, AT5G61605, AT5G61630, AT5G61660, AT5G61710, AT5G61865, AT5G61920, AT5G61940, AT5G61950, AT5G61970, AT5G62090, AT5G62140, AT5G62170, AT5G62240, AT5G62270, AT5G62330, AT5G62400, AT5G62440, AT5G62550, AT5G62575, AT5G62623, AT5G62627, AT5G62640, AT5G62750, AT5G62760, AT5G62900, AT5G62960, AT5G63000, AT5G63040, AT5G63050, AT5G63135, AT5G63320, AT5G63340, AT5G63350, AT5G63500, AT5G63540, AT5G63550, AT5G63720, AT5G63740, AT5G63820, AT5G63830, AT5G63905, AT5G64010, AT5G64090, AT5G64130, AT5G64160, AT5G64170, AT5G64180, AT5G64190, AT5G64230, AT5G64310, AT5G64400, AT5G64480, AT5G64510, AT5G64520, AT5G64540, AT5G64550, AT5G64680, AT5G64690, AT5G64770, AT5G64780, AT5G64800, AT5G64816, AT5G64820, AT5G64850, AT5G64870, AT5G64880, AT5G64890, AT5G64900, AT5G64905, AT5G64930, AT5G65120, AT5G65180, AT5G65207, AT5G65250, AT5G65300, AT5G65340, AT5G65390, AT5G65480, AT5G65495, AT5G65540, AT5G65580, AT5G65610, AT5G65660, AT5G65770, AT5G65810, AT5G65880, AT5G65925, AT5G66000, AT5G66030, AT5G66052, AT5G66230, AT5G66250, AT5G66290, AT5G66340, AT5G66440, AT5G66480, AT5G66490, AT5G66580, AT5G66640, AT5G66658, AT5G66740, AT5G66780, AT5G66800, AT5G66815, AT5G66820, AT5G66985, AT5G67020, AT5G67245, AT5G67350, AT5G67390, AT5G67410, AT5G67550, AT5G67600, AT5G67610, AT5G67620, AT5G67640, ATCG00870, ATCG01270, ATMG00010, ATMG00030, ATMG00050, ATMG00120, ATMG00130, ATMG00150, ATMG00170, ATMG00180, ATMG00200, ATMG00260, ATMG00300, ATMG00310, ATMG00320, ATMG00400, ATMG00430, ATMG00440, ATMG00450, ATMG00470, ATMG00500, ATMG00530, ATMG00540, ATMG00550, ATMG00600, ATMG00610, ATMG00620, ATMG00630, ATMG00660, ATMG00670, ATMG00680, ATMG00720, ATMG00740, ATMG00750, ATMG00760, ATMG00770, ATMG00840, ATMG00870, ATMG00880, ATMG00890, ATMG00910, ATMG00920, ATMG00970, ATMG01000, ATMG01010, ATMG01020, ATMG01030, ATMG01040, ATMG01050, ATMG01060, ATMG01090, ATMG01100, ATMG01130, ATMG01140, ATMG01150, ATMG01180, ATMG01200, ATMG01210, ATMG01220, ATMG01230, ATMG01240, ATMG01260, ATMG01290, ATMG01300, ATMG01310, ATMG01330, ATMG01350, ATMG01370, and ATMG01400. With regard to the POFs identified in *Arabidopsis*, the following POFs were identified as specific either to a single species or a single genus (referred to herein as ssPOFs): Locus ID AT1G01400, AT1G01810, AT1G01990, AT1G02320, AT1G02350, AT1G02405, AT1G02450, AT1G02490, AT1G02540, AT1G02710, AT1G02965, AT1G03106, AT1G03200, AT1G03240, AT1G03320, AT1G03420, AT1G03660, AT1G04660, AT1G04670, AT1G04800, AT1G05040, AT1G05065, AT1G05085, AT1G05330, AT1G05340, AT1G05450, AT1G05490, AT1G05575, AT1G06135, AT1G06320, AT1G06420, AT1G06475, AT1G06930, AT1G07135, AT1G07190, AT1G07473, AT1G07500, AT1G07680, AT1G07690, AT1G08035, AT1G09415, AT1G10100, AT1G10420, AT1G10990, AT1G11470, AT1G11850, AT1G12080, AT1G12660, AT1G12805, AT1G12810, AT1G12845, AT1G13605, AT1G13607, AT1G13608, AT1G13609, AT1G13620, AT1G13670, AT1G13755, AT1G14755, AT1G15385, AT1G15757, AT1G15825, AT1G15830, AT1G15840, AT1G16025, AT1G16515, AT1G16730, AT1G17090, AT1G17285, AT1G17300, AT1G17510, AT1G17780, AT1G17900, AT1G18220, AT1G18510, AT1G19394,
AT1G19397, AT1G19500, AT1G19620, AT1G19960,
AT1G20070, AT1G20100, AT1G20280, AT1G20690,
AT1G21020, AT1G21323, AT1G21395, AT1G21475,
AT1G21520, AT1G21940, AT1G21950, AT1G22010,
AT1G22120, AT1G22140, AT1G22335, AT1G22590,
AT1G22885, AT1G22890, AT1G23050, AT1G23650,
AT1G24060, AT1G24145, AT1G24390, AT1G24575,
AT1G24822, AT1G24851, AT1G24938, AT1G24996,
AT1G25025, AT1G25097, AT1G25112, AT1G25170,
AT1G25180, AT1G25425, AT1G26140, AT1G26210,
AT1G26290, AT1G26350, AT1G26710, AT1G26720,
AT1G27550, AT1G27610, AT1G27640, AT1G27670,
AT1G27695, AT1G27710, AT1G27790, AT1G28135,
AT1G28375, AT1G28630, AT1G29010, AT1G29179,
AT1G29355, AT1G29480, AT1G29530, AT1G29540,
AT1G29560, AT1G29580, AT1G29610, AT1G29620,
AT1G30250, AT1G30515, AT1G30757, AT1G30795,
AT1G30814, AT1G30835, AT1G31060, AT1G31150,
AT1G31270, AT1G31335, AT1G31520, AT1G31580,
AT1G31620, AT1G31750, AT1G31772, AT1G31835,
AT1G31960, AT1G31990, AT1G32000, AT1G32010,
AT1G32040, AT1G32290, AT1G32337, AT1G32570,
AT1G32630, AT1G32650, AT1G32670, AT1G32680,
AT1G32920, AT1G32928, AT1G32975, AT1G33135,
AT1G33607, AT1G33640, AT1G33820, AT1G33860,
AT1G34047, AT1G34095, AT1G34280, AT1G34315,
AT1G34400, AT1G34440, AT1G34590, AT1G34730,
AT1G34910, AT1G35030, AT1G35040, AT1G35080,
AT1G35100, AT1G35183, AT1G35230, AT1G35320,
AT1G35375, AT1G35435, AT1G35500, AT1G35513,
AT1G35614, AT1G35617, AT1G35640, AT1G35820,
AT1G35880, AT1G35890, AT1G35900, AT1G36100,
AT1G36230, AT1G36395, AT1G36640, AT1G36670,
AT1G36675, AT1G36745, AT1G36756, AT1G36763,
AT1G36925, AT1G36960, AT1G36970, AT1G37000,
AT1G37015, AT1G37037, AT1G37045, AT1G38380,
AT1G38630, AT1G38790, AT1G38950, AT1G39350,
AT1G40080, AT1G40115, AT1G40125, AT1G40129,
AT1G40133, AT1G40230, AT1G41650, AT1G41750,
AT1G41770, AT1G41810, AT1G41820, AT1G41855,
AT1G41870, AT1G41900, AT1G42080, AT1G42190,
AT1G42367, AT1G42393, AT1G42515, AT1G42580,
AT1G42630, AT1G42700, AT1G42740, AT1G43205,
AT1G43230, AT1G43320, AT1G43415, AT1G43720,
AT1G43777, AT1G43810, AT1G43920, AT1G43940,
AT1G43970, AT1G44085, AT1G44222, AT1G44740,
AT1G44850, AT1G44875, AT1G44930, AT1G44990,
AT1G45165, AT1G45403, AT1G46336, AT1G47280,
AT1G47317, AT1G47395, AT1G47400, AT1G47485,
AT1G47495, AT1G47660, AT1G47680, AT1G47690,
AT1G47700, AT1G47770, AT1G47813, AT1G48145,
AT1G48250, AT1G48325, AT1G48730, AT1G49110,
AT1G49150, AT1G49500, AT1G49680, AT1G49715,
AT1G49940, AT1G50080, AT1G50220, AT1G50290,
AT1G50350, AT1G50530, AT1G50800, AT1G50930,
AT1G51000, AT1G51010, AT1G51030, AT1G51430,
AT1G51915, AT1G51970, AT1G52087, AT1G52090,
AT1G52390, AT1G52410, AT1G52550, AT1G52615,
AT1G52827, AT1G52840, AT1G52905, AT1G53265,
AT1G53285, AT1G53480, AT1G53610, AT1G53620,
AT1G53625, AT1G53640, AT1G53785, AT1G53935,
AT1G53970, AT1G54420, AT1G54445, AT1G54575,
AT1G54640, AT1G54720, AT1G54880, AT1G54923,
AT1G54926, AT1G54950, AT1G55220, AT1G55330,
AT1G55400, AT1G55675, AT1G55710, AT1G55990,
AT1G56085, AT1G56270, AT1G56415, AT1G56530,
AT1G56553, AT1G56555, AT1G56660, AT1G58055,
AT1G58150, AT1G58225, AT1G58235, AT1G58242,
AT1G59535, AT1G59722, AT1G59865, AT1G59885,
AT1G60240, AT1G60983, AT1G60987, AT1G61090,
AT1G61095, AT1G61097, AT1G61200, AT1G61688,
AT1G61920, AT1G62060, AT1G62070,
AT1G62080, AT1G62210, AT1G62220, AT1G62225,
AT1G62240, AT1G62480, AT1G62690, AT1G62935,
AT1G63055, AT1G63105, AT1G63240, AT1G63522,
AT1G63535, AT1G63960, AT1G64107, AT1G64360,
AT1G64370, AT1G64405, AT1G64490, AT1G64560,
AT1G64800, AT1G65342, AT1G65352, AT1G65490,
AT1G65500, AT1G65510, AT1G65845, AT1G66145,
AT1G66245, AT1G66790, AT1G66820, AT1G67350,
AT1G67670, AT1G67775, AT1G67855, AT1G67860,
AT1G67865, AT1G67870, AT1G68250, AT1G68430,
AT1G68725, AT1G68845, AT1G68870, AT1G68875,
AT1G68905, AT1G68907, AT1G68935, AT1G68945,
AT1G69050, AT1G69470, AT1G69760, AT1G69825,
AT1G69970, AT1G70350, AT1G70470, AT1G70895,
AT1G70990, AT1G71235, AT1G71470, AT1G71910,
AT1G72080, AT1G72580, AT1G72600, AT1G72645,
AT1G73130, AT1G73177, AT1G73510, AT1G73603,
AT1G73607, AT1G74045, AT1G74055, AT1G75190,
AT1G75770, AT1G75870, AT1G76230, AT1G76820,
AT1G76840, AT1G76910, AT1G76955, AT1G76960,
AT1G76965, AT1G77655, AT1G77765, AT1G77885,
AT1G77910, AT1G77960, AT1G78030, AT1G79170,
AT1G80610, AT1G80865, AT2G01031, AT2G01175,
AT2G01310, AT2G01400, AT2G02280, AT2G02440,
AT2G02490, AT2G02515, AT2G02795, AT2G02835,
AT2G02840, AT2G03180, AT2G03310, AT2G03320,
AT2G03540, AT2G03570, AT2G03580, AT2G03830,
AT2G03932, AT2G03937, AT2G04000, AT2G04025,
AT2G04034, AT2G04045, AT2G04046, AT2G04063,
AT2G04320, AT2G04370, AT2G04380, AT2G04410,
AT2G04515, AT2G04600, AT2G04675, AT2G04800,
AT2G04870, AT2G04925, AT2G05000, AT2G05117,
AT2G05185, AT2G05270, AT2G05350, AT2G05500,
AT2G05564, AT2G05645, AT2G05647, AT2G05752,
AT2G05915, AT2G06095, AT2G06140, AT2G06166,
AT2G06230, AT2G06390, AT2G06420, AT2G06480,
AT2G06555, AT2G06570, AT2G06620, AT2G06630,
AT2G06645, AT2G06750, AT2G06775, AT2G06906,
AT2G06908, AT2G06914, AT2G07000, AT2G07190,
AT2G07215, AT2G07280, AT2G07290, AT2G07310,
AT2G07505, AT2G07669, AT2G07672, AT2G07673,
AT2G07674, AT2G07676, AT2G07678, AT2G07691,
AT2G07692, AT2G07701, AT2G07702, AT2G07705,
AT2G07706, AT2G07708, AT2G07710, AT2G07713,
AT2G07719, AT2G07721, AT2G07724, AT2G07728,
AT2G07738, AT2G07772, AT2G07774, AT2G07775,
AT2G07776, AT2G07777, AT2G07779, AT2G07787,
AT2G07795, AT2G07880, AT2G07981, AT2G08986,
AT2G09388, AT2G09840, AT2G09865, AT2G09900,
AT2G10020, AT2G10105, AT2G10110, AT2G10175,
AT2G10285, AT2G10340, AT2G10360, AT2G10380,
AT2G10390, AT2G10470, AT2G10550, AT2G10555,
AT2G10602, AT2G10608, AT2G10850, AT2G10870,
AT2G10920, AT2G10930, AT2G10965, AT2G10975,
AT2G11005, AT2G11010, AT2G11090, AT2G11135,
AT2G11370, AT2G11405, AT2G11462, AT2G11570,
AT2G11620, AT2G11626, AT2G11775, AT2G11910,
AT2G12110, AT2G12120, AT2G12130, AT2G12170,
AT2G12320, AT2G12405, AT2G12465, AT2G12475,
AT2G12505, AT2G12610, AT2G12685, AT2G12700,
AT2G12875, AT2G12905, AT2G12935, AT2G12945,
AT2G13125, AT2G13126, AT2G13270, AT2G13320,
AT2G13430, AT2G13500, AT2G13510, AT2G13550,
AT2G13660, AT2G13730, AT2G13760, AT2G13865,
AT2G13975, AT2G14000, AT2G14020, AT2G14240,
AT2G14247, AT2G14340, AT2G14390, AT2G14460,
AT2G14590, AT2G14600, AT2G14700, AT2G14774, AT2G14800, AT2G14810, AT2G14890, AT2G14935, AT2G15185, AT2G15327, AT2G15340, AT2G15345, AT2G15420, AT2G15535, AT2G15550, AT2G15600, AT2G15800, AT2G15815, AT2G15830, AT2G15930, AT2G15960, AT2G16015, AT2G16020, AT2G16170, AT2G16340, AT2G16410, AT2G16575, AT2G16586, AT2G16676, AT2G16820, AT2G17442, AT2G17540, AT2G17723, AT2G17960, AT2G18070, AT2G18200, AT2G18270, AT2G18440, AT2G18610, AT2G18920, AT2G18930, AT2G18970, AT2G19200, AT2G19290, AT2G19300, AT2G19320, AT2G19420, AT2G19700, AT2G19802, AT2G19850, AT2G19893, AT2G20150, AT2G20208, AT2G20250, AT2G20463, AT2G20595, AT2G20620, AT2G20625, AT2G20870, AT2G20970, AT2G21185, AT2G21237, AT2G21465, AT2G21725, AT2G21780, AT2G22000, AT2G22080, AT2G22121, AT2G22122, AT2G22320, AT2G22340, AT2G22470, AT2G22510, AT2G22520, AT2G22805, AT2G22807, AT2G22820, AT2G22905, AT2G22940, AT2G22941, AT2G23040, AT2G23130, AT2G23440, AT2G23490, AT2G23920, AT2G23985, AT2G24285, AT2G24310, AT2G24340, AT2G24460, AT2G24617, AT2G24625, AT2G24780, AT2G24910, AT2G24945, AT2G25185, AT2G25250, AT2G25510, AT2G25565, AT2G25685, AT2G25990, AT2G26120, AT2G26880, AT2G27250, AT2G27315, AT2G27380, AT2G27390, AT2G27535, AT2G27540, AT2G28330, AT2G28570, AT2G28625, AT2G29045, AT2G29180, AT2G29790, AT2G29920, AT2G29995, AT2G30430, AT2G30560, AT2G30760, AT2G30925, AT2G30930, AT2G30960, AT2G30985, AT2G31035, AT2G31345, AT2G31590, AT2G31700, AT2G31751, AT2G31850, AT2G32275, AT2G32890, AT2G33233, AT2G34010, AT2G34100, AT2G34110, AT2G34120, AT2G34123, AT2G34185, AT2G34220, AT2G34230, AT2G34270, AT2G34310, AT2G34330, AT2G34655, AT2G34800, AT2G34870, AT2G35070, AT2G35080, AT2G35090, AT2G35733, AT2G35750, AT2G35870, AT2G36030, AT2G36040, AT2G36255, AT2G36440, AT2G36695, AT2G36724, AT2G36920, AT2G36940, AT2G37070, AT2G37300, AT2G37910, AT2G38350, AT2G38690, AT2G38823, AT2G39160, AT2G39520, AT2G39680, AT2G40020, AT2G40085, AT2G40530, AT2G40765, AT2G40955, AT2G41230, AT2G41260, AT2G41280, AT2G41390, AT2G41400, AT2G41420, AT2G41440, AT2G41650, AT2G41780, AT2G41905, AT2G42050, AT2G42340, AT2G42395, AT2G42540, AT2G42860, AT2G42955, AT2G43450, AT2G44010, AT2G45403, AT2G45780, AT2G45860, AT2G45930, AT2G46360, AT2G46390, AT2G47200, AT2G47660, AT2G47720, AT2G47950, AT2G48075, AT2G48090, AT3G01230, AT3G01240, AT3G01250, AT3G01323, AT3G01325, AT3G01345, AT3G01700, AT3G01730, AT3G01960, AT3G02240, AT3G02390, AT3G02670, AT3G03020, AT3G04640, AT3G04903, AT3G04943, AT3G05080, AT3G05460, AT3G05727, AT3G05730, AT3G05935, AT3G06090, AT3G06360, AT3G06435, AT3G06545, AT3G06600, AT3G06710, AT3G06750, AT3G06870, AT3G06895, AT3G07005, AT3G07195, AT3G07568, AT3G07710, AT3G09032, AT3G09130, AT3G09162, AT3G09280, AT3G09750, AT3G09922, AT3G10116, AT3G10195, AT3G10525, AT3G10830, AT3G10930, AT3G11060, AT3G11160, AT3G11640, AT3G11745, AT3G11860, AT3G12510, AT3G12840, AT3G12977, AT3G13240, AT3G13370, AT3G13403, AT3G13435, AT3G13500, AT3G13630, AT3G13674, AT3G13845, AT3G13857, AT3G14340, AT3G14395, AT3G14480, AT3G14560, AT3G14670, AT3G15357, AT3G15400, AT3G15440, AT3G15780, AT3G15860, AT3G15910, AT3G16750, AT3G16895, AT3G17155, AT3G17190, AT3G18250, AT3G18485, AT3G18540, AT3G18700, AT3G19030, AT3G19055, AT3G19530, AT3G19790, AT3G20155, AT3G20362, AT3G20555, AT3G20850, AT3G20865, AT3G20900, AT3G21570, AT3G21680, AT3G22070, AT3G22090, AT3G22231, AT3G22235, AT3G22240, AT3G22415, AT3G23040, AT3G23165, AT3G23167, AT3G23172, AT3G23245, AT3G23295, AT3G23715, AT3G23720, AT3G23727, AT3G23850, AT3G24225, AT3G24250, AT3G24280, AT3G24380, AT3G24508, AT3G24510, AT3G24513, AT3G24517, AT3G24640, AT3G24770, AT3G25080, AT3G25200, AT3G25655, AT3G25727, AT3G25882, AT3G25905, AT3G26110, AT3G26235, AT3G26616, AT3G26800, AT3G27025, AT3G27370, AT3G27590, AT3G27800, AT3G27906, AT3G27990, AT3G28110, AT3G28120, AT3G28170, AT3G28190, AT3G28240, AT3G28260, AT3G28280, AT3G28420, AT3G28530, AT3G28590, AT3G29034, AT3G29080, AT3G29140, AT3G29210, AT3G29300, AT3G29305, AT3G29560, AT3G29570, AT3G29600, AT3G29610, AT3G29700, AT3G29786, AT3G29790, AT3G29796, AT3G30150, AT3G30160, AT3G30220, AT3G30250, AT3G30320, AT3G30350, AT3G30360, AT3G30490, AT3G30510, AT3G30520, AT3G30580, AT3G30590, AT3G30610, AT3G30645, AT3G30650, AT3G30660, AT3G30670, AT3G30690, AT3G30700, AT3G30720, AT3G30750, AT3G30751, AT3G30755, AT3G30816, AT3G30820, AT3G30840, AT3G30845, AT3G31300, AT3G31310, AT3G31320, AT3G31330, AT3G31350, AT3G31370, AT3G31400, AT3G31406, AT3G31540, AT3G31910, AT3G31915, AT3G31940, AT3G31955, AT3G32050, AT3G32070, AT3G32100, AT3G32120, AT3G32150, AT3G32160, AT3G32180, AT3G32190, AT3G32200, AT3G32896, AT3G32902, AT3G32903, AT3G32904, AT3G32960, AT3G33064, AT3G33073, AT3G33080, AT3G33131, AT3G33187, AT3G33230, AT3G33293, AT3G33393, AT3G33448, AT3G33494, AT3G33572, AT3G42070, AT3G42090, AT3G42120, AT3G42130, AT3G42140, AT3G42190, AT3G42200, AT3G42240, AT3G42254, AT3G42300, AT3G42310, AT3G42380, AT3G42390, AT3G42430, AT3G42436, AT3G42473, AT3G42480, AT3G42490, AT3G42510, AT3G42520, AT3G42540, AT3G42556, AT3G42590, AT3G42610, AT3G42680, AT3G42700, AT3G42723, AT3G42740, AT3G42750, AT3G42780, AT3G42786, AT3G42810, AT3G42870, AT3G42920, AT3G42970, AT3G42990, AT3G43140, AT3G43150, AT3G43153, AT3G43160, AT3G43280, AT3G43290, AT3G43410, AT3G43420, AT3G43450, AT3G43470, AT3G43480, AT3G43500, AT3G43528, AT3G43580, AT3G43583, AT3G43680, AT3G43682, AT3G43833, AT3G43863, AT3G43870, AT3G43880, AT3G43940, AT3G43970, AT3G44040, AT3G44070, AT3G44140, AT3G44170, AT3G44210, AT3G44230, AT3G44235, AT3G44430, AT3G44440, AT3G44470, AT3G44570, AT3G44580, AT3G44690, AT3G44755, AT3G44760, AT3G44770, AT3G44935, AT3G44950, AT3G44980, AT3G45093, AT3G45110, AT3G45120, AT3G45160, AT3G45230, AT3G45320, AT3G45360, AT3G45370, AT3G45443, AT3G45730, AT3G45820, AT3G45910, AT3G46150, AT3G46360, AT3G46380, AT3G46390, AT3G47100, AT3G47230, AT3G47240, AT3G47295, AT3G47320, AT3G47410, AT3G47510, AT3G47836, AT3G47920, AT3G47965, AT3G48185, AT3G48231, AT3G48640, AT3G49230, AT3G49270, AT3G49300, AT3G49305, AT3G49307, AT3G49540, AT3G49770, AT3G49820, AT3G50250, AT3G50320, AT3G50373, AT3G50540, AT3G50550, AT3G50570, AT3G50580, AT3G50925, AT3G52550, AT3G52700, AT3G53235, AT3G54520, AT3G54530, AT3G54730, AT3G55790, AT3G55860, AT3G55910, AT3G56260, AT3G56390, AT3G56610, AT3G56670, AT3G56910, AT3G57110, AT3G57160,
AT3G57210, AT3G57690, AT3G57850, AT3G58080,
AT3G58230, AT3G58280, AT3G58300, AT3G58330,
AT3G58540, AT3G58770, AT3G58870, AT3G59370,
AT3G59460, AT3G59880, AT3G59930, AT3G60560,
AT3G60760, AT3G60890, AT3G60930, AT3G61898,
AT3G62350, AT3G62400, AT3G62480, AT3G62490,
AT3G62990, AT3G63040, AT3G63050, AT3G63100,
AT3G63160, AT4G00280, AT4G00890, AT4G00930,
AT4G01340, AT4G01525, AT4G01535, AT4G01735,
AT4G01895, AT4G01915, AT4G01985, AT4G02000,
AT4G02160, AT4G02465, AT4G03165, AT4G03305,
AT4G03505, AT4G03580, AT4G03680, AT4G03740,
AT4G03750, AT4G03940, AT4G03970, AT4G03975,
AT4G03979, AT4G04155, AT4G04273, AT4G04394,
AT4G04396, AT4G04398, AT4G04423, AT4G04525,
AT4G04730, AT4G04820, AT4G04925, AT4G05290,
AT4G05523, AT4G05553, AT4G05560, AT4G05580,
AT4G05581, AT4G05616, AT4G05631, AT4G05632,
AT4G05636, AT4G05640, AT4G06490, AT4G06603,
AT4G06637, AT4G06672, AT4G06716, AT4G06724,
AT4G06728, AT4G06735, AT4G06740, AT4G07380,
AT4G07452, AT4G07460, AT4G07485, AT4G07500,
AT4G07523, AT4G07526, AT4G07666, AT4G07675,
AT4G07740, AT4G07825, AT4G07868, AT4G07932,
AT4G07943, AT4G07965, AT4G08028, AT4G08039,
AT4G08097, AT4G08098, AT4G08111, AT4G08130,
AT4G08270, AT4G08336, AT4G08395, AT4G08485,
AT4G08555, AT4G08593, AT4G08602, AT4G08710,
AT4G08730, AT4G08740, AT4G08760, AT4G08868,
AT4G08869, AT4G08874, AT4G08875, AT4G09030,
AT4G09153, AT4G09210, AT4G09220, AT4G09260,
AT4G09270, AT4G09290, AT4G09390, AT4G09647,
AT4G09840, AT4G09850, AT4G09860, AT4G09880,
AT4G09984, AT4G10820, AT4G10845, AT4G10860,
AT4G10870, AT4G11020, AT4G11100, AT4G11385,
AT4G11393, AT4G11700, AT4G11870, AT4G11940,
AT4G12005, AT4G12220, AT4G12380, AT4G12580,
AT4G12735, AT4G12930, AT4G12940, AT4G12990,
AT4G13095, AT4G13150, AT4G13195, AT4G13235,
AT4G13320, AT4G13470, AT4G13955, AT4G13968,
AT4G14104, AT4G14120, AT4G14315, AT4G14530,
AT4G14650, AT4G14810, AT4G15096, AT4G15150,
AT4G15460, AT4G15563, AT4G15650, AT4G15710,
AT4G15733, AT4G15735, AT4G15950, AT4G15990,
AT4G16000, AT4G16040, AT4G16090, AT4G16140,
AT4G16215, AT4G16240, AT4G16447, AT4G16460,
AT4G16515, AT4G16840, AT4G16980, AT4G17700,
AT4G17713, AT4G17930, AT4G17990, AT4G18000,
AT4G18080, AT4G18090, AT4G18280, AT4G18310,
AT4G18395, AT4G18420, AT4G18490, AT4G18500,
AT4G18501, AT4G18510, AT4G18580, AT4G18823,
AT4G18850, AT4G18860, AT4G19095, AT4G19200,
AT4G19240, AT4G19270, AT4G19280, AT4G19290,
AT4G19305, AT4G19320, AT4G19480, AT4G19620,
AT4G19905, AT4G20095 AT4G20250, AT4G20290,
AT4G20470, AT4G20500, AT4G20510, AT4G20690,
AT4G20715, AT4G21215, AT4G21865, AT4G21920,
AT4G21950, AT4G22210, AT4G22214, AT4G22217,
AT4G22235, AT4G22420, AT4G22430, AT4G22440,
AT4G22510, AT4G22800, AT4G23090, AT4G23110,
AT4G23493, AT4G23760, AT4G23770, AT4G23780,
AT4G23870, AT4G23970, AT4G24030, AT4G24275,
AT4G24300, AT4G24410, AT4G24600, AT4G24950,
AT4G25510, AT4G26030, AT4G26040, AT4G26290,
AT4G26320, AT4G26960, AT4G27415, AT4G27530,
AT4G27580, AT4G27652, AT4G27654, AT4G27657,
AT4G27850, AT4G27930, AT4G28085, AT4G28160,
AT4G28180, AT4G28460, AT4G28810, AT4G28870,
AT4G28920, AT4G28930, AT4G29020, AT4G29030,
AT4G29200, AT4G29273, AT4G29280, AT4G29285,
AT4G29290, AT4G29300, AT4G29305, AT4G30050,
AT4G30064, AT4G30450, AT4G30460, AT4G30662,
AT4G30670, AT4G30730, AT4G30750, AT4G30970,
AT4G31030, AT4G31260, AT4G31280, AT4G31875,
AT4G31960, AT4G32080, AT4G32230, AT4G32240,
AT4G33310, AT4G33560, AT4G33610, AT4G33660,
AT4G33666, AT4G33750, AT4G33960, AT4G34690,
AT4G35170, AT4G35400, AT4G35430, AT4G35725,
AT4G36170, AT4G36370, AT4G36460, AT4G36510,
AT4G36515, AT4G36560, AT4G36925, AT4G37295,
AT4G37450, AT4G37685, AT4G38080, AT4G38330,
AT4G38820, AT4G39320, AT4G39360, AT4G39403,
AT4G39675, AT4G39745, AT4G39917, AT4G39930,
AT4G40090, AT5G01080, AT5G01881, AT5G02000,
AT5G02520, AT5G02550, AT5G02650, AT5G02690,
AT5G03090, AT5G03060, AT5G03130, AT5G03210,
AT5G03400, AT5G03545, AT5G03550, AT5G03710,
AT5G03920, AT5G03930, AT5G03950, AT5G04030,
AT5G04045, AT5G04470, AT5G04650, AT5G04790,
AT5G05020, AT5G05640, AT5G05965, AT5G06043,
AT5G06190, AT5G06380, AT5G06980, AT5G07730,
AT5G08090, AT5G08150, AT5G08185, AT5G08210,
AT5G08220, AT5G08505, AT5G09480, AT5G09520,
AT5G09980, AT5G09990, AT5G10040, AT5G10430,
AT5G10590, AT5G10670, AT5G10745, AT5G11120,
AT5G11830, AT5G11990, AT5G12880, AT5G12990,
AT5G13825, AT5G14330, AT5G14380, AT5G14560,
AT5G14730, AT5G15000, AT5G15190, AT5G15360,
AT5G15420, AT5G15560, AT5G15725, AT5G15960,
AT5G15970, AT5G15990, AT5G17130, AT5G17340,
AT5G17360, AT5G17590, AT5G17650, AT5G18403,
AT5G18407, AT5G18690, AT5G19172, AT5G19800,
AT5G19810, AT5G20460, AT5G20760, AT5G20770,
AT5G21020, AT5G21110, AT5G21125, AT5G21910,
AT5G22150, AT5G22160, AT5G22170, AT5G22180,
AT5G22190, AT5G22520, AT5G22530, AT5G22545,
AT5G22555, AT5G22680, AT5G22970, AT5G23035,
AT5G23180, AT5G23212, AT5G23460, AT5G23640,
AT5G24250, AT5G24313, AT5G24316, AT5G24480,
AT5G24570, AT5G24590, AT5G25000, AT5G25210,
AT5G25425, AT5G25600, AT5G25750, AT5G25870,
AT5G25920, AT5G26020, AT5G26070, AT5G26080,
AT5G26100, AT5G26270, AT5G26350, AT5G26622,
AT5G26692, AT5G26717, AT5G26720, AT5G26800,
AT5G26840, AT5G26890, AT5G26970, AT5G27170,
AT5G27180, AT5G27340, AT5G27440, AT5G27500,
AT5G27590, AT5G27606, AT5G27800, AT5G27890,
AT5G28070, AT5G28090, AT5G28110, AT5G28120,
AT5G28130, AT5G28140, AT5G28170, AT5G28190,
AT5G28240, AT5G28270, AT5G28295, AT5G28410,
AT5G28430, AT5G28463, AT5G28480, AT5G28482,
AT5G28484, AT5G28560, AT5G28600, AT5G28610,
AT5G28620, AT5G28623, AT5G28630, AT5G28720,
AT5G28785, AT5G28790, AT5G28800, AT5G28810,
AT5G28820, AT5G28860, AT5G28920, AT5G28990,
AT5G29020, AT5G29050, AT5G29070, AT5G29090,
AT5G29210, AT5G29576, AT5G29602, AT5G29613,
AT5G30341, AT5G30520, AT5G31685, AT5G31752,
AT5G31753, AT5G31787, AT5G31838, AT5G31873,
AT5G32161, AT5G32169, AT5G32312, AT5G32405,
AT5G32410, AT5G32590, AT5G32600, AT5G32605,
AT5G32610, AT5G32619, AT5G32775, AT5G33230,
AT5G33355, AT5G33380, AT5G33390, AT5G33393,
AT5G33715, AT5G33806, AT5G33898, AT5G34358,
AT5G34450, AT5G34581, AT5G34820, AT5G34830,
AT5G34910, AT5G34970, AT5G34980, AT5G35010,
AT5G35020, AT5G35035, AT5G35090, AT5G35195,
AT5G35230, AT5G35270, AT5G35290, AT5G35300,
AT5G35470, AT5G35480, AT5G35490, AT5G35510, AT5G35540, AT5G35603, AT5G35604, AT5G35646, AT5G35737, AT5G35760, AT5G35792, AT5G35880, AT5G35890, AT5G35945, AT5G36020, AT5G36035, AT5G36040, AT5G36060, AT5G36070, AT5G36080, AT5G36190, AT5G36650, AT5G36720, AT5G36735, AT5G36900, AT5G36920, AT5G36925, AT5G36960, AT5G37120, AT5G37240, AT5G37385, AT5G37473, AT5G37474, AT5G37880, AT5G38080, AT5G38090, AT5G38190, AT5G38310, AT5G38400, AT5G38595, AT5G38790, AT5G38980, AT5G39140, AT5G39170, AT5G39205, AT5G39365, AT5G39570, AT5G39880, AT5G40070, AT5G40110, AT5G40155, AT5G40180, AT5G40595, AT5G40620, AT5G40730, AT5G40855, AT5G41320, AT5G41640, AT5G41660, AT5G42110, AT5G42146, AT5G42223, AT5G42232, AT5G42235, AT5G42242, AT5G42530, AT5G42635, AT5G42797, AT5G42825, AT5G43000, AT5G43185, AT5G43285, AT5G43401, AT5G43405, AT5G43480, AT5G43510, AT5G43513, AT5G43770, AT5G44005, AT5G44313, AT5G44565, AT5G44570, AT5G44575, AT5G44580, AT5G44880, AT5G44973, AT5G45573, AT5G46115, AT5G46120, AT5G46300, AT5G46310, AT5G46320, AT5G46500, AT5G46730, AT5G46770, AT5G46871, AT5G46873, AT5G46874, AT5G46877, AT5G47170, AT5G48175, AT5G48200, AT5G48280, AT5G48420, AT5G48515, AT5G48530, AT5G48595, AT5G48605, AT5G48657, AT5G48860, AT5G48953, AT5G49015, AT5G49090, AT5G49250, AT5G49260, AT5G49280, AT5G49440, AT5G49590, AT5G49640, AT5G49790, AT5G50190, AT5G50335, AT5G50500, AT5G50540, AT5G50565, AT5G50610, AT5G50645, AT5G50665, AT5G50710, AT5G50880, AT5G50910, AT5G51090, AT5G51105, AT5G51195, AT5G51390, AT5G51580, AT5G51650, AT5G51845, AT5G52080, AT5G52130, AT5G52547, AT5G52965, AT5G53410, AT5G53740, AT5G53895, AT5G53905, AT5G53960, AT5G54067, AT5G54095, AT5G54145, AT5G54215, AT5G54350, AT5G54410, AT5G54460, AT5G54585, AT5G54790, AT5G54970, AT5G55010, AT5G55131, AT5G55132, AT5G55135, AT5G55420, AT5G55430, AT5G55507, AT5G55650, AT5G55680, AT5G55750, AT5G55790, AT5G55870, AT5G55893, AT5G56100, AT5G56368, AT5G56369, AT5G56795, AT5G56880, AT5G57310, AT5G57400, AT5G57650, AT5G57730, AT5G57760, AT5G57790, AT5G57887, AT5G58570, AT5G58650, AT5G59060, AT5G59105, AT5G59170, AT5G59330, AT5G59360, AT5G60000, AT5G60240, AT5G60260, AT5G60290, AT5G60330, AT5G60350, AT5G60400, AT5G60553, AT5G60650, AT5G60805, AT5G60810, AT5G61110, AT5G61120, AT5G61360, AT5G61605, AT5G61660, AT5G61710, AT5G62330, AT5G62400, AT5G62623, AT5G62627, AT5G62750, AT5G63340, AT5G63720, AT5G63820, AT5G63905, AT5G64540, AT5G64690, AT5G64770, AT5G64800, AT5G64890, AT5G64900, AT5G64905, AT5G65300, AT5G65390, AT5G65495, AT5G65580, AT5G65610, AT5G65880, AT5G65925, AT5G66000, AT5G66052, AT5G66340, AT5G66658, AT5G66985, AT5G67245, AT5G67350, AT5G67600, AT5G67640, ATCG00870, ATCG01270, ATMG00030, ATMG00050, ATMG00120, ATMG00130, ATMG00150, ATMG00200, ATMG00260, ATMG00320, ATMG00400, ATMG00430, ATMG00440, ATMG00450, ATMG00470, ATMG00500, ATMG00530, ATMG00540, ATMG00600, ATMG00610, ATMG00630, ATMG00670, ATMG00680, ATMG00720, ATMG00740, ATMG00760, ATMG00770, ATMG00840, ATMG00870, ATMG00880, ATMG00890, ATMG00920, ATMG00970, ATMG01000, ATMG01010, ATMG01020, ATMG01030, ATMG01040, ATMG01050, ATMG01060, ATMG01090, ATMG01100, ATMG01130, ATMG01140, ATMG01150, ATMG01180, ATMG01200, ATMG01210, ATMG01230, ATMG01240, ATMG01260, ATMG01290, ATMG01300, ATMG01310, ATMG01350, ATMG01370, and ATMG01400. Such POFs can be analyzed (e.g., knock-out mutation, over-expression; etc.) for their ability to modify the amount of at least one biochemical component in the plant species in which it was found, i.e., *Arabidopsis* for the POFs identified above. After it has been determined that a POF can modify the amount of at least one biochemical component in the plant species in which it was found, the POF can be introduced (e.g., in accordance with the methods described herein and known in the art) into another plant species, which is preferably from another genus and the WT of which does not contain the POF, and analyzed for its ability to modify the amount of at least one biochemical component in that plant species. When the protein database was searched with a protein query using the NCBI BLAST program, QQS had an Expect value of 4e-29 to itself only as determined using the method of compositional matrix adjust.

EXAMPLES

The following examples serve to illustrate the present disclosure. The examples are not intended to limit the scope of the claimed invention.

Example 1

This example describes the construction of a vector for expression of QQS in plants other than *Arabidopsis*.

Figure 3:
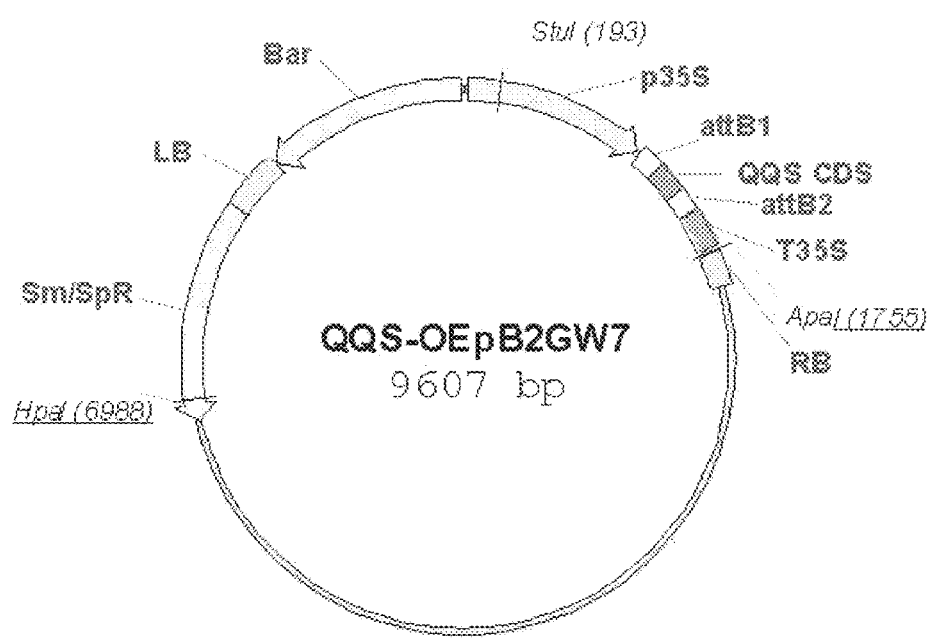
FIG. 3 is a drawing of the construction of a vector (QQS-OE At3g30720) for expression of QQS in plants other than *Arabidopsis*, wherein Hpa I, Stu I and Apa I are restriction endonuclease sites, Sm/SpR is a gene resistant to spectinomycin, LB is the left transfer-DNA border, Bar is a gene that confers resistance to the herbicide bialaphos, p35S is the Cauliflower mosaic virus (CaMV) 35S promoter, attB1 and attB2 are Gateway DNA recombination sites B1 and B2, T35S is the terminator of the CaMV 35S promoter, RB is the right transfer-DNA border, and QQS CDS is the coding sequence for QQS (180 nts; nucleotides 301-480 of SEQ ID NO: 1).

A 35S::QQS fusion construct was made by cloning the amplified, full-length, coding sequence into a binary vector pB2GW7 as shown in FIG. 3. QQS was expressed under the control of the 35S promoter. 35S::QQS-pB2GW7 vector was transformed into *Agrobacterium tumefaciens* strain EHA101.

Example 2

This example describes the transformation and selection of transgenic, QQS-expressing soybean lines.

The cultivar Williams 82 was transformed by *Agrobacterium*-mediated transformation using the half-seed explants method (Paz et al., Euphytica 136: 167-179 (2004)). The transformation and selection of R1 plants were performed in the Plant Transformation Facility at Iowa State University. Soybean plants from independent transformations were selected based on Bar resistance.

Example 3

This example describes the analysis of starch content of the leaves of soybean expressing QQS as compared to WT soybean.

Transgenic, QQS-expressing soybean lines (ST94-32#1, ST94-32#2 and ST94-16#1) and a WT soybean line (Williams 82) were grown in pots with three plants/pot under controlled environmental conditions of 16 hours of light at 27° C. and 8 hours of dark at 20° C. in a growth chamber. The pots were placed randomly in the growth chamber.

Leaves from the top nodes of three individual plants (500-1,000 mg fresh weight) were pooled and boiled in 50 mL 80% (v/v) ethanol. The boiled leaves were then ground with a mortar and pestle in 80% ethanol and centrifuged for 10 min at 13,000 rpm. The resulting pellet was washed twice with 80% ethanol. After washing, the insoluble material was suspended in 10 mL of distilled water and boiled for 30 min. Total starch (D-glucose) in each leaf sample was quantified using amyloglucosidase and Megazyme's GOPOD format (Megazyme International Ireland Ltd., Wicklow, Ireland). This analysis was conducted in triplicate. The results are shown in Table 1 and FIG. 2.

Example 4

This example describes the analysis of oil, protein and moisture contents of the seeds of soybean expressing QQS as compared to WT soybean.

The oil, protein, and moisture contents of seeds were measured by nuclear magnetic resonance (NMR) with the Minispec-mq-one (BRUKER Optics Inc., The Woodlands, Tex.). Seeds were placed in a 10 mm glass tube and weighed. The tube was placed in the Minispec-mq-one and on-screen instructions were followed. The software provided with the Minispec-mq-one calculates the % of oil, protein, and moisture as desired. Data were transformed from fresh weight to dry weight. The results are shown in Table 1 and FIG. 2.

Example 5

This example describes the analysis of total RNA of the leaves of soybean expressing QQS as compared to WT soybean.

Total RNA was extracted from the pooled leaf samples of Example 1 using the TRIzol RNA isolation method. Total RNA was purified using the QIAGEN RNeasy Mini Kit (QIAGEN, Valencia, Calif.).

One microgram of total RNA was reverse-transcribed using 200 ng random hexamers (Invitrogen, Paisley, UK) and Superscript II reverse transcriptase (Invitrogen) according to the supplier's instructions. cDNA was stored at 4° C. until amplified using polymerase chain reaction (PCR).

Specific primers and fluorogenic probes for QQS were purchased from Applied Biosystems (At03403756_sH UBQ10; Warrington, UK) for use in PCR. The 18S ribosomal RNA (18S rRNA) control Reagent (Applied Biosystems) was used as an endogenous control to normalize for differences in the amount of total RNA in each sample and for RNA quality control (Zhong et al., Biochem. Biophys. Res. Comm. 259: 523-526 (1999); Schmittgen et al., J. Biochem. Biophys. Meth. 46: 69-81 (2000); and Bhatia et al., Anal. Biochem. 216: 223-226 (1994)). PCR reactions were performed using the 7500 Fast Real-Time PCR System (Applied Biosystems). Each reaction was performed in 25 µl reactions and contained the equivalent of 5 ng of reverse-transcribed RNA (1 ng RNA for the 18S analyses), 50% TaqMan 2×PCR Master Mix (PE Applied Biosystems), and 1.25 µl of primer/probe mix as recommended by the manufacturer. Conditions for the PCR reaction were 10 min at 95° C. and then 40 cycles, each consisting of 15 sec at 95° C., and 1 min at 60° C.

The relative RNA levels within the samples were determined by generating standard curves for the PCR reaction by using the cDNA from one sample and making 2-fold serial dilutions covering the range equivalent to 100 ng-3.125 ng of total RNA (for 18S rRNA analyses, the range was 4 ng-0.125 ng). Samples were analysed using the standard curve method described by Applied Biosystems. Those samples, which showed more than 2 cycle threshold (Ct) variation from the median 18S rRNA Ct value, were excluded so that expression profiles were not distorted. The results are shown in Table 1.

TABLE 1

| Sample | QQS/18S rRNA (by RT-PCR) | Starch (mg/g fresh wt; % decrease) | Oil (% of dry wt; % decrease) | Protein (% of dry wt; % increase) | Fresh Weight (mean g per seed) |
|---|---|---|---|---|---|
| QQS-Williams 82 #1 | 81.78 | 4.64*; 70.18% | 19.05*; 5.00% | 51.24**; 60.63% | 0.162 |
| QQS-Williams 82 #2 | 4.57 | 2.71*; 82.58% | 16.76**; 16.41% | 42.31**; 32.63% | 0.161 |
| QQS-Williams 82 #11 | 15.81 | 7.51*; 51.74% | 17.39**; 13.27% | 46.92**; 47.08% | 0.156 |
| Williams 82 | 0.00 | 15.56 | 20.05 | 31.9 | 0.159 |

*Student's t-test, P < 0.05
**Student's t-test, P < 0.01

As shown in Table 1 and FIG. 2, the starch content of leaves of soybean lines expressing QQS is significantly lower than the starch content of leaves of WT soybean (Williams 82). The oil content of seeds of QQS-expressing soybean is also lower than the oil content of seeds of WT soybean. In distinct contrast to the starch content of leaves and the oil content of seeds, however, the protein content of seeds of QQS-expressing soybean is significantly higher than the protein content of seeds of WT soybean.

Example 6

This example describes the analysis of oil, protein and moisture contents of the seeds of soybean expressing QQS as compared to WT soybean and grown in a growth chamber, a greenhouse, or a field.

Transgenic, QQS-expressing soybean lines (ST94-32#1, ST94-32#2 and ST94-16#1) and a WT soybean line (Williams 82) were grown in pots with three plants/pot under controlled environmental conditions of 16 hours of light at 27° C. and 8 hours of dark at 20° C. in a growth chamber. The pots were placed randomly in the growth chamber.

Transgenic, QQS-expressing soybean lines (ST94-32#1, ST94-32#2 and ST94-16#1) and a WT soybean line (Williams 82) were grown in pots with three plants/pot under controlled environmental conditions of 16 hours of light at 27° C. and 8 hours of dark at 20° C. in a greenhouse. The pots were placed randomly in the greenhouse.

Transgenic, QQS-expressing soybean lines (ST94-32#1, ST94-32#2 and ST94-16#1) and a WT soybean line (Williams 82) were grown in a field in Ames, Iowa Five replicates, each containing one row of each line, were planted.

The oil, protein, and moisture contents of seeds were measured by near-infrared spectroscopy (NIRS). Data were adjusted to a moisture content of 10.97%. The data are shown in Tables 2-4. As shown in Table 2, protein is increased (up to 16.85%) and oil and fiber are decreased in QQS-expressing mutant soybean plants grown in a growth chamber. As shown in Table 3, protein is increased (up to 13.5%), and oil, fiber and carbohydrates are decreased in QQS-expressing mutant soybean plants grown in a green house. As shown in Table 4, protein is increased (up to 9.5%), and oil, fiber and carbohydrates are decreased in QQS-expressing mutant soybean plants grown in a field.

TABLE 2

Growth Chamber Data for R2 Seeds (Year 2010)

| | Mean | | | | | Change (% WT) | | | | QQS | Leaf |
|---|---|---|---|---|---|---|---|---|---|---|---|
| | Moisture (%) | Protein* | Oil* | Fiber* | P + O* | Protein | Oil | Fiber | P + O | Transcripts[+] | Starch^ |
| QQS-Williams 82 #1 | 7.83 | 38.47 | 18.49 | 4.88 | 56.96 | 9.93 | −5.25 | −4.72 | 4.49 | 81.7844 | 4.6401 |
| QQS-Williams 82 #2 | 6.57 | 39.33 | 18.18 | 4.81 | 57.51 | 12.37 | −6.81 | −6.06 | 5.51 | 5.11354 | 5.2615 |
| QQS-Williams 82 #3 | 5.93 | 40.90 | 17.57 | 4.78 | 58.47 | 16.85 | −9.96 | −6.72 | 7.26 | 2.73198 | 13.638 |
| QQS-Williams 82 #4 | 6.93 | 37.90 | 18.73 | 4.81 | 56.62 | 8.28 | −4.01 | −6.06 | 3.88 | 45.3269 | 14.94 |
| QQS-Williams 82 #5 | 5.97 | 37.56 | 18.73 | 4.88 | 56.28 | 7.30 | −4.01 | −4.73 | 3.25 | 4.57207 | 2.7128 |
| QQS-Williams 82 #6 | 6.40 | 39.54 | 17.98 | 4.74 | 57.51 | 12.96 | −7.86 | −7.39 | 5.51 | 2.62104 | 5.7704 |
| QQS-Williams 82 #7 | 7.50 | 38.89 | 18.32 | 4.78 | 57.20 | 11.11 | −6.11 | −6.73 | 4.94 | 2.87029 | 11.014 |
| QQS-Williams 82 #8 | 10.97 | 40.01 | 19.07 | 4.57 | 59.08 | 14.32 | −2.27 | −10.72 | 8.38 | 2.19775 | 5.6369 |
| Williams 82 | 6.73 | 35.00 | 19.51 | 5.12 | 54.51 | 0.00 | 0.00 | 0.00 | 0.00 | 0 | 15.561 |

*data shown for mean protein, oil, fiber, and P + O (protein and oil) are based on % of dry weight
[+]data shown for QQS transcripts are based on QQS/18S rRNA
^data shown for leaf starch are based on mg/g fresh weight

TABLE 3

Green House Data for R2 Seeds (Year 2011)

| | Mean | | | | | | Change (% WT) | | | | | QQS | Leaf |
|---|---|---|---|---|---|---|---|---|---|---|---|---|---|
| | Moisture (%) | Protein* | Oil* | Fiber* | CHO* | P + O* | Protein | Oil | Fiber | CHO | P + O | Transcripts[+] | Starch^ |
| QQS-Williams 82 #10 Plant 4 | 7.30 | 40.57 | 20.35 | 4.54 | 19.83 | 60.92 | 10.39 | −2.35 | −7.04 | −13.06 | 5.78 | 0.745933 | |
| QQS-Williams 82 #10 Plant 8 | 7.20 | 39.25 | 19.63 | 4.75 | 21.67 | 58.88 | 6.80 | −5.84 | −2.78 | −5.00 | 2.23 | 0.745933 | |
| QQS-Williams 82 #1 | 7.70 | 41.72 | 18.24 | 4.65 | 20.70 | 59.95 | 13.51 | −12.51 | −4.92 | −9.26 | 4.09 | 81.78443 | 4.64013 |
| QQS-Williams 82 #1 Plant 5 | 7.10 | 39.49 | 20.04 | 4.68 | 21.53 | 59.08 | 6.24 | −3.85 | −4.20 | −5.61 | 2.59 | 81.78443 | 4.64013 |
| QQS-Williams 82 #4 | 7.47 | 39.74 | 18.34 | 4.82 | 22.40 | 58.08 | 8.12 | −12.00 | −1.36 | −1.81 | 0.84 | 45.32694 | 14.9403 |
| QQS-Williams 82 #5 | 10.90 | 39.49 | 19.00 | 4.89 | 21.91 | 58.49 | 7.46 | −8.84 | 0.06 | −3.94 | 1.56 | 4.572071 | 2.71278 |
| QQS-Williams 82 #2 Plant 1 | 9.17 | 38.94 | 18.93 | 4.82 | 22.61 | 57.87 | 5.95 | −9.17 | −1.36 | −0.90 | 0.48 | 2.621037 | 5.77036 |

TABLE 3-continued

Green House Data for R2 Seeds (Year 2011)

| | Mean | | | | | | Change (% WT) | | | | | QQS Transcripts[+] | Leaf Starch[^] |
|---|---|---|---|---|---|---|---|---|---|---|---|---|---|
| | Moisture (%) | Protein* | Oil* | Fiber* | CHO* | P + O* | Protein | Oil | Fiber | CHO | P + O | | |
| QQS-Williams 82 #3 | 7.70 | 38.08 | 20.04 | 4.819 | 22.363 | 58.12 | 3.6 | −3.9 | −1.4 | −2.0 | 0.9 | 2.870293 | 11.014 |
| Williams 82 #5 | 7.60 | 40.01 | 19.244 | 4.681 | 21.359 | 59.26 | 8.9 | −7.7 | −4.2 | −6.4 | 2.9 | 2.197754 | 5.63693 |
| Williams 82 | 9.43 | 36.75 | 20.84 | 4.89 | 22.82 | 57.59 | 0.00 | 0.00 | 0.00 | 0.00 | 0.00 | 0 | 15.5605 |

*data shown for mean protein, oil, fiber, CHO (carbohydrates), and P + O (protein and oil) are based on % of dry weight
[+]data shown for QQS transcripts are based on QQS/18S rRNA
[^]data shown for leaf starch are based on mg/g fresh weight

TABLE 4

Field Data for R2/R3 Seeds (Year 2011)

| | Mean | | | | | | Change (% WT) | | | | | QQS Transcripts[+] | Leaf Starch[^] |
|---|---|---|---|---|---|---|---|---|---|---|---|---|---|
| | Moisture (%) | Protein* | Oil* | Fiber* | CHO* | P + O* | Protein | Oil | Fiber | CHO | P + O | | |
| QQS-Williams 82 #1 | 8.5 | 35.99 | 17.91 | 5.15 | 24.87 | 53.90 | 3.33 | −0.57 | −1.95 | −3.70 | 2.00 | 81.78443 | 4.64013 |
| QQS-Williams 82 #6 | 9.7 | 36.98 | 17.19 | 5.08 | 24.66 | 54.17 | 6.17 | −4.55 | −3.25 | −4.49 | 2.52 | 2.621037 | 5.77036 |
| QQS-Williams 82 #7 | 7.0 | 35.78 | 17.91 | 5.12 | 25.11 | 53.69 | 2.74 | −0.57 | −2.60 | −2.77 | 1.61 | 2.870293 | 11.014 |
| QQS-Williams 82 #9 | 7.3 | 38.17 | 16.20 | 5.05 | 24.49 | 54.37 | 9.50 | −10.23 | −3.90 | −4.89 | 2.78 | 0.031645 | 8.73995 |
| Williams 82 | 7 | 34.83 | 18.01 | 5.25 | 25.82 | 52.84 | 0.00 | 0.00 | 0.00 | 0.00 | 0.00 | 0 | 15.5605 |

*data shown for mean protein, oil, fiber CHO (carbohydrates), and P + O (protein and oil) are based on % of dry weight
[+]data shown for QQS transcripts are based on QQS/18S rRNA
[^]data shown for leaf starch are based on mg/g fresh weight While protein content and total protein+oil content increased under all conditions, the increases in protein content and total protein+oil content were greater under growth chamber/green house conditions compared to field conditions. The differences may reflect the fact that the soil in the growth chamber and the green house was supplemented with fertilizer (i.e., Miracle Gro Excel 15-5-15), whereas the soil in the field was not. This study will be repeated with supplementation of soil under all growth conditions.

Example 7

This example describes the effects of over-expression and under-expression of QQS on the expression of genes involved in plant defense.

Total RNA was extracted from pooled leaf samples using TRIzol (Life Technologies, Carlsbad, Calif.). The RNA was further purified using the QIAGEN RNeasy Mini Kit (QIAGEN, Valencia, Calif.) with the DNAse I (Life Technologies, Carlsbad, Calif.) treatment to remove DNA contamination.

A 200-bp short-insert library was constructed. Transcriptome sequencing was performed with an Illumina HiSeq2000 system using V3 Reagent (91 air end sequencing). Low-quality reads were filtered out by removing reads with adaptors, reads with more than 5% unknown nucleotides, and reads with more than 20% bases having a quality of ≤10. The cleaned reads were aligned to the reference *Arabidopsis thaliana* genome in Phytozome version 8.0 (phytozome.net) using TopHat. The mapped reads were counted by htseq-count (huber.embl.de/users/anders/HTSeq/doc/count.html).

Analysis of RNA-Seq data from QQS RNAi (down-regulating QQS), QQS OE (over-expressing QQS) and wild-type Col-0 *Arabidopsis* plants revealed that plant defense-related marker genes had perturbed transcript levels relative to wild-type *Arabidopsis* as shown in Table 5.

TABLE 5

|  |  | Mean (three replicates) | | | Ratio | | P value | |
| --- | --- | --- | --- | --- | --- | --- | --- | --- |
| Locus | Gene | QQS RNAi | QQS OE | WT (Col-0) | QQS RNAi to WT | QQS OE to WT | QQS RNAi vs WT | QQS OE vs WT |
| AT1G19640 | JMT jasmonic acid carboxyl methyltransferase | 34.5 | 35 | 19.7 | 1.75 | 1.78 | 0.06 | 0.03 |
| AT1G32640 | MYC2 transcription factor MYC2 | 323.5 | 439 | 285.7 | 1.13 | 1.54 | 0.67 | 0.04 |
| AT1G43160 | RAP2.6 ethylene-responsive transcription factor RAP2-6 | 4.5 | 11.5 | 1.3 | 3.38 | 8.63 | 0.45 | 0.09 |
| AT1G56650 | PAP1 transcription factor MYB75 | 117 | 119.5 | 82.3 | 1.42 | 1.45 | 0.04 | 0.01 |
| AT1G64280 | NPR1 Regulatory protein NPR1 | 113 | 89 | 112.3 | 1.01 | 0.79 | 0.87 | 0.18 |
| AT1G80840 | WRKY40 putative WRKY transcription factor 40 | 20 | 36.5 | 18.3 | 1.09 | 1.99 | 0.89 | 0.07 |
| AT2G14610 | PR1 pathogenesis-related protein 1 | 128.5 | 620.5 | 307.3 | 0.42 | 2.02 | 0.16 | 0.19 |
| AT2G26020 | PDF1.2b putative defensin-like protein | 1 | 9.5 | 4.3 | 0.23 | 2.19 | 0.14 | 0.19 |
| AT2G43790 | MPK6 MAP kinase 6 | 169.5 | 125.5 | 162.0 | 1.05 | 0.77 | 0.87 | 0.09 |
| AT3G05500 | AT3G05500 Rubber elongation factor protein; stress related protein | 74.5 | 102.5 | 70.7 | 1.05 | 1.45 | 0.90 | 0.04 |
| AT3G14620 | CYP72A8 cytochrome P450, family 72, subfamily A, polypeptide 8 | 304.5 | 311 | 316.0 | 0.96 | 0.98 | 0.67 | 0.81 |
| AT4G01720 | WRKY47 putative WRKY transcription factor 47 | 19.5 | 15.5 | 35.0 | 0.56 | 0.44 | 0.01 | 0.00 |
| AT5G22570 | WRKY38 putative WRKY transcription factor 38 | 7.5 | 29.5 | 18.0 | 0.42 | 1.64 | 0.06 | 0.14 |

The patterns can be categorized into three groups. The first group is comprised of one gene with decreased expression in both mutants, namely WRKY47, which is highly activated by bacterial infection and is involved in the induction of basal defense (Truman et al., Plant J. 46(1): 14-33 (2006)). The second group is comprised of four genes with increased expression in both mutants. The four genes are JMT, which is a key metabolic enzyme of jasmonate (JA)-regulated plant responses (Seo et al., PNAS USA 98(8): 4788-4793 (2001)), MYC2, which is a JA-responsive transcriptional factor that modulates antagonism between jasmonate and ethylene (ET) signaling (Chico et al., Plant Cell 26(5): 1967-1980 (2014); Song et al., Plant Cell 26(1): 263-279 (2014); and Zhang et al., Plant Cell 26(3): 1105-1117 (2014)), PAP1, a JA-responsive transcriptional factor that activates anthocyanin biosynthesis depending on the activation of Col1 by JA (Shan et al., J. Exp. Bot. 60(13): 3849-3860 (2009)), and RAB2-6, which is an ET-responsive transcriptional factor that triggers callose deposition in planta (Ali et al., BMC Plant Biol. 13: 47 (2013)). The third group is comprised of three genes with decreased expression in mutants in which QQS is down-regulated and increased expression in mutants in which QQS is over-expressed. The three genes are WRKY38, which is an NPR-dependent basal defense negative regulator that regulates SA-triggered immunity (Caillaud et al., PLoS Biol. 11(12): e1001732 (2013); Kim et al., Plant Cell 20(9): 2357-2371 (2008); Pre et al., Plant Physiol. 147(3): 1347-1357 (2008); and Seo et al. (2001), supra), NPR1 regulatory protein, and PR1 pathogenesis-related protein.

Example 8

This example demonstrates that viral infection decreased in transgenic *Arabidopsis thaliana* plants overexpressing NF-YC4 or QQS.

Turnip mosaic virus carrying green fluorescent protein (TuMV-GFP) inoculation assay was performed as previously described (Yang et al., Molecular Plant-Microbe Interactions 20(4): 358-370 (2007)) with some minor modifications. Frozen TuMV-GFP-infected turnip (Seven Top) leaves were ground in 20 mM sodium phosphate buffer (pH 7.2, 1:6 wt/vol) and filtered through Miracloth (Calbiochem, San Diego, Calif.) to obtain the inoculum. The titer of the inoculum was adjusted to yield well-separated GFP loci.

*Arabidopsis thaliana* plants were grown for seven weeks in 10 hr of light at 22° C. to allow large rosette leaves to develop. Rosette leaves were dusted with Carborundum and rub-inoculated with TuMV-GFP using a cotton-stick applicator. At 120 hr after inoculation (hai), GFP foci on the inoculated rosette leaves were counted under UV illumination (100-W Blak-Ray longwave UV lamp; UVP, Upland, Calif.). Each line had three biological replicates of 10 randomly selected plants. The average foci number of 10 plants for each line was calculated, and the significance of foci number differences between lines was determined using the Student's t-test (P<0.01 or 0.05).

For each genotype, 40 single GFP foci were randomly selected and photographed on a Zeiss Stemi SV11 fluorescence dissecting microscope using a Zeiss AxioCam MRc5 digital camera (Hewezi et al., Plant Cell 20(11): 3080-3093 (2008)). The digital files were then processed using Zeiss AxioVision software. Each photographed GFP focus was processed with the ImageJ measure tool (NIH) and calibrated against the correct scaling of the original image from the Stemi SV11. The total area for the GFP focus was calculated as square millimeters. The individual measurements for the GFP focus of each line were used to calculate an average focus size for each line tested. Significance of size differences between lines was determined via the Student's t-test (P<0.01 or 0.05).

TuMV-GFP was inoculated on *A. thaliana* plants with different genetic backgrounds of QQS and NF-YC4. GFP foci (number indicates the ability of TuMV to initiate the infection process) were counted and the sizes of GFP foci (size indicates the ability of TuMV to reproduce in planta) were measured at five days after inoculation. *Arabidopsis thaliana* Col-0 lines with altered QQS expression and altered expression of the QQS interactor NF-YC4 were used in all infection assays. The lines used were Col-0 (few trichomes, control for transformants) for AtQQS RNAi (QQS-downregulating), AtQQS OE (QQS-overexpressing), and AtNF-YC4 OE (NF-YC4-overexpressing) and Col-0 (trichomes, control for T-DNA knock-out (KO) mutants) for AtQQS KO and AtNF-YC4 KO.

Figure 4A:
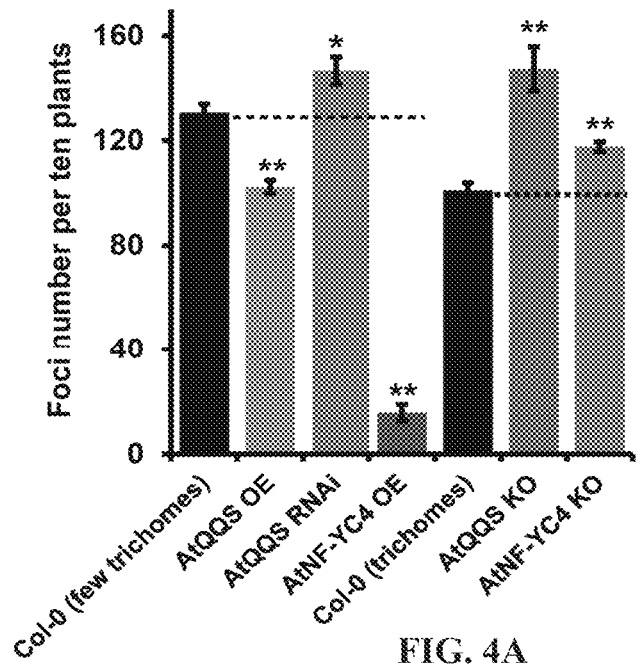
FIG. 4a is a graph of mutant vs. controls for average foci number per 10 plants (±standard error at 120 hours after inoculation (hai)).
Figure 4B:
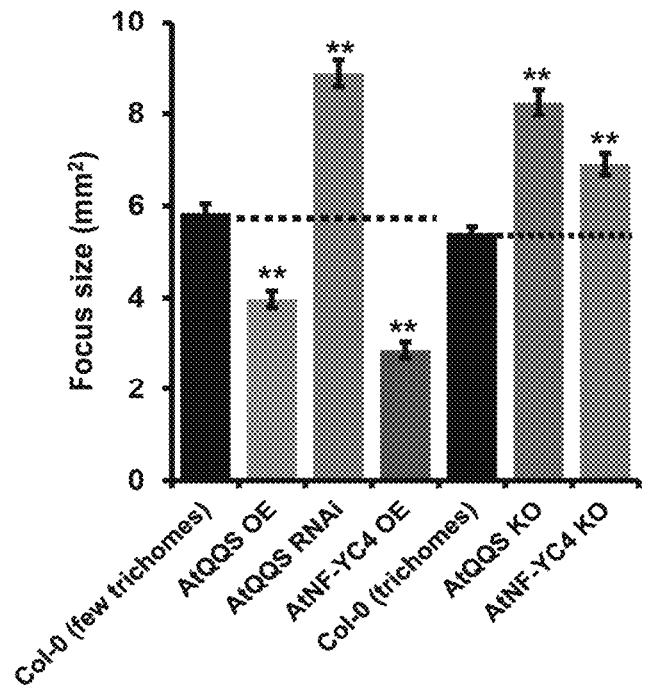
FIG. 4b is a graph of mutant vs. controls for average focus size ($mm^2$) (±standard error at 120 hai (n=40)).

As shown in FIGS. 4a (a graph of mutant vs. average foci number per 10 plants (±standard error at 120 hours after inoculation (hai)) and 4b (graph of mutant vs. average focus size ($mm^2$) (±standard error at 120 hai (n=40)), AtNF-YC4 OE plants had significantly decreased numbers of GFP foci, approximately 88% fewer than the controls. In contrast, AtNF-YC4 KO plants had slightly increased foci numbers, approximately 16.5% more than the controls; though small, the Student's t-test suggested that the difference was significant. Similarly, the AtQQS OE plants had 21.7% fewer foci compared to the control plants, while the AtQQS RNAi plants had 12.2% more foci than the control plants, and the AtQQS KO plants had 45.9% more foci than the controls. These results showed that over-expressing either AtQQS or AtNF-YC4 impaired the viral infection initiation, while silencing or knocking-out AtQQS or AtNF-YC4 facilitated the viral infection initiation. YC4 over-expression almost blocked the viral infection.

The changes in foci sizes had a similar trend. The foci in AtNF-YC4 KO, AtQQS KO and AtQQS-silenced plants were 27.8%, 52.5% and 51.9% larger, respectively, than the controls, whereas the foci in AtNF-YC4 OE and AtQQS OE plants were 51% and 32% smaller, respectively. than the controls.

These results showed that overexpressing AtNF-YC4 or AtQQS impairs viral reproduction, while silencing or knocking-out AtNF-YC4 or AtQQS facilitates viral reproduction. The assays indicate that QQS and its interactor, NF-YC4, decrease initiation of infection and decrease viral reproduction in planta. Thus, they are positive regulators of plant immune response, since over-expression of each increases plant resistance to virus.

Example 9

This example demonstrates that bacterial growth decreased in transgenic *Arabidopsis thaliana* plants overexpressing NF-YC4 or QQS.

*A. thaliana* plants were grown in growth chamber under 10 hr of light and 14 hr of dark at 22° C. for 4-5 weeks. *Pseudomonas syringae* were washed and re-suspended in inoculation buffer (10 mM $MgCl_2$, 0.05% Silwet L-77). Plants were sprayed with a bacterial inoculum with the bacterial level adjusted to $10^8$ colony-forming units (CFU)/mL (Katagiri et al., The *Arabidopsis thaliana*—*Pseudomonas syringae* Interaction. The *Arabidopsis* Book/American Society of Plant Biologists, 1, e0039.http://doi.org/10.1199/tab.0039 (2002)). Bacterial levels in planta were determined by cutting leaf disks with a cork borer (inner diameter 0.5 cm) and completely homogenizing them in 500 μl of the inoculation buffer. The resulting suspensions containing the bacteria was diluted and plated on KB plates with the appropriate antibiotics.

Bacterial growth in planta of Pst DC3000 and the ΔCEL strain in the same set of *A. thaliana* plants listed in Example 8 was examined. Pst DC3000 is a bacterial pathogen that robustly infects *A. thaliana* plants, while ΔCEL, a mutated Pst DC3000 strain with mutations in multiple effector genes, is a non-virulent strain that grows slowly in planta. Pst DC3000 grew approximately 1,000-fold in four days, while ΔCEL grew approximately 10-fold. The growth of Pst DC3000 was greatly impaired in plants over-expressing AtNF-YC4 or AtQQS, with 88% and 63% decreases, respectively. In contrast, in the AtQQS or AtNF-YC4 RNAi and KO lines, the growth of Pst DC3000 was increased by approximately 30%. The increased growth of Pst DC3000 was quite significant in the AtQQS RNAi plants, while that in AtQQS or AtNF-YC4 KO lines was not significant at the level of p=0.05.

On the other hand, it was quite obvious that the growth of ΔCEL in the AtQQS or AtNF-YC4 RNAi or KO lines was strongly enhanced with approximately a 2.6-fold increase. The growth change of ΔCEL was not similarly significant in the AtQQS or AtNF-YC4 over-expression plants. Overall, the data about the altered growth of both bacterial strains in *A. thaliana* plants of different genetic backgrounds indicate that over-expressing AtNF-YC4 or AtQQS enhances the plant immune responses, making the robustly infectious bacterial pathogen less virulent and slow-growing, while silencing or knocking out AtNF-YC4 or AtQQS impairs the plant immune responses, making the non-virulent bacterial pathogen grow better. So, these data consistently suggest that AtNF-YC4 and AtQQS are positive regulators of plant immune responses.

Figure 5:
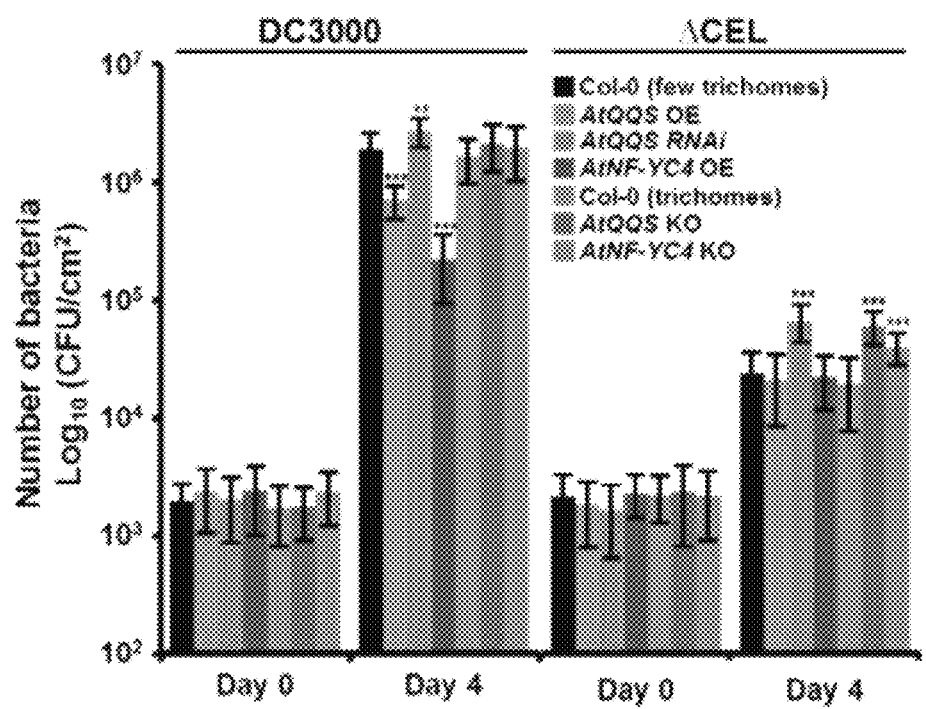
FIG. 5 is a graph of Day 0 (0 dpi) and Day 4 (4 dpi) for Pst DC3000 and Δ CEL vs. number of bacteria ($log_{10}$ ($CFU/cm^2$)). Error bars indicate the standard errors.  $p<0.01$. * $p<0.001$.

The results are summarized in FIG. 5. FIG. 5 is a graph of Day 0 (0 dpi) and Day 4 (4 dpi) for Pst DC3000 and Δ CEL vs. number of bacteria ($log_{10}$ ($CFU/cm^2$)). Error bars indicate the standard errors. Initial inoculum was adjusted uniformly to $10^8$ CFU/mL. Pairwise Student's t-test was used to compare mutants with their corresponding controls.

Example 10

This example demonstrates that bacterial growth decreased in transgenic soybean plants overexpressing NF-YC4 or expressing QQS.

Stable, transgenic soybean lines expressing AtQQS (AtQQS E) or over-expressing GmNF-YC4 (Glyma06g17780; GmNF-YC4 OE) were generated and grown in growth chamber under 14 hrs of light and 10 hrs of dark at 22° C. The soybean mutant plants of QQS E, GmNF-YC4 OE, and empty vector control were selected by PCR-screening of leaf DNA. The first trifoliates on 23-day-old soybeans were used for inoculation. Freshly cultured *P. savastanoi* pv. *glycinea* Race 4 (PsgR4) was suspended in the inoculation buffer (see Example 22) to the final concentration of around $10^7$ CFU/mL. The leaflets of each trifoliate leaf were pricked by needle before 5 μL of the inoculum were placed onto each wound (10/leaflet). Bacterial levels in planta were determined at 10 days after inoculation as described above.

Psg causes bacterial blight on soybean, which was considered as a great threat to soybean production. PsgR4 is one of the most virulent strains, since it can infect almost all commercial soybean cultivars. Using the soybean line carrying the empty vector as control, PsgR4 grew much slower in the soybean GmNF-YC4 OE line and the soybean AtQQS E line, with a 62.4% and a 55.3% decrease, respectively. The impaired bacterial growth of PsgR4 in soybean lines over-expressing GmNF-YC4 or expressing AtQQS indicated that GmNF-YC4 and AtQQS enhance soybean immune response as well, which is consistent with the above data that NF-YC4 and QQS are positive regulators of plant immune responses.

Figures 6A, 6B:
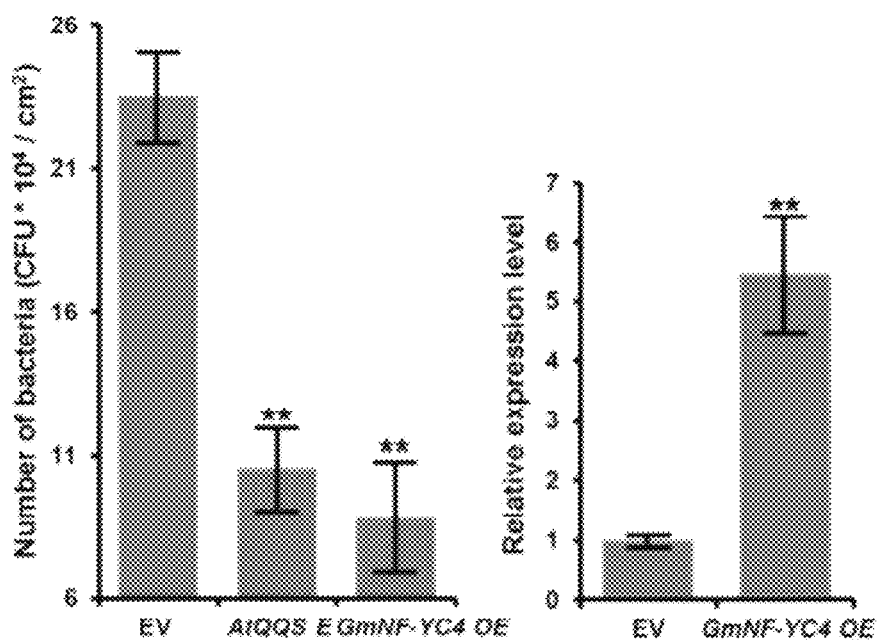
FIG. 6a is a graph of soybean line for number of bacteria ($CFU*10^4/cm^2$). Error bars indicate the standard errors. ** $p<0.01$. (EV=empty vector)
FIG. 6b is a graph of soybean line for relative expression level. Error bars indicate the standard errors. ** $p<0.01$. (EV=empty vector)

The results are summarized in FIG. 6a. FIG. 6a is a graph of soybean line vs. number of bacteria ($CFU*10^4/cm^2$; EV=empty vector). Error bars indicate the standard errors. ** p<0.01. Initial inoculum was adjusted uniformly to $10^7$ CFU/mL. Pairwise Student's t-test was used to compare mutants with their corresponding controls.

To confirm that GmNF-YC4 was over-expressed in the transgenic soybean lines, the expression level of GmNF-YC4 was determined using quantitative real-time PCR. Approximately 100 mg soybean leaves were used for RNA isolation using the RNeasy Plant Mini Kit (Qiagen) according to the manufacturer's instructions. Two μg of RNA and SuperScript® III First Strand kit (Invitrogen) were used for cDNA synthesis. Quantitative real-time PCR (qRT-PCR) was performed using the cDNA and gene-specific primers (GmNF-YC4Fd: 5'-CCTCCCAGGCATGGCAGTCC-3' [SEQ ID NO: 3] and GmNF-YC4Rev: 5'-CCAT-CAAGGCTCCGCTGG-3' [SEQ ID NO: 4]. Each cDNA was amplified by quantitative PCR using iQ™ SYBR® Green Supermix (Bio-Rad) and iCycler real-time PCR system (Bio-Rad). GmACTIN expression was used to normalize the expression value in each sample, and the relative expression values were determined against mock samples using the comparative Ct method ($2^{-\Delta\Delta Ct}$).

GmACTIN (Glyma 15g050200) was used as the reference gene (Liu et al., Mol. Plant Microbe Interact. 27(8): 824-834 (2014)). The expression level of GmNF-YC4 in the GmNF-YC4 OE line was 4.47-fold higher than expression in the soybean control line.

The results are summarized in FIG. 6b. FIG. 6b is a graph of soybean line vs. relative expression level (EV=empty vector). Error bars indicate the standard errors. ** $p<0.01$.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of increasing resistance to a pathogen or a pest in a plant, said method comprising the steps of: (a) transforming plant cells with a polynucleotide comprising a nucleotide sequence encoding an *Arabidopsis* Qua-Quine Starch (QQS) polypeptide, wherein the nucleotide sequence is operably linked to a promoter; (b) regenerating transgenic plants from the transformed plant cells; and (c) identifying and selecting a transgenic plant that exhibits increased resistance to the pathogen or the pest as compared to an untransformed plant of the same species lacking the QQS polypeptide and grown under similar conditions, wherein the pathogen or the pest is a bacterium, a virus, or a fungus and the increased resistance to the pathogen or the pest is due to the expression of the QQS polypeptide in the selected transgenic plant.

2. The method of claim 1, wherein the QQS polypeptide has the amino acid sequence as set forth in SEQ ID NO: 2.

3. The method of claim 1, wherein the promoter is a constitutive promoter, an inducible promoter, a developmentally specific promoter, a synthetic promoter, or a hybrid promoter.

4. The method of claim 3, wherein the constitutive promoter is the cauliflower mosaic virus 35S promoter or the developmentally specific promoter is a seed-specific promoter.

5. The method of claim 1, wherein the plant is a crop plant.

6. The method of claim 5, wherein the crop plant is soybean.

7. The method of claim 1, wherein the plant is a monocot.

8. The method of claim 1, wherein the plant is a dicot.

9. A method of producing a plant with increased resistance to a pathogen or a pest, which method comprises crossing a transgenic plant, which comprises and expresses a polynucleotide comprising a nucleotide sequence encoding an *Arabidopsis* Qua-Quine Starch (QQS) polypeptide and operably linked to a promoter and wherein, due to the expression of the QQS polypeptide, the transgenic plant exhibits increased resistance to the pathogen or the pest as compared to a plant of the same species, which does not comprise and express the QQS polypeptide and is grown under similar conditions, with a second plant of the same species to produce progeny plants and selecting progeny plants that express the QQS polypeptide, and wherein the pathogen or the pest is a bacterium, a virus, or a fungus.

10. The method of claim 9, wherein the QQS polypeptide has the amino acid sequence as set forth in SEQ ID NO: 2.

11. The method of claim 9, wherein the promoter is a constitutive promoter, an inducible promoter, a developmentally specific promoter, a synthetic promoter, or a hybrid promoter.

12. The method of claim 11, wherein the constitutive promoter is the cauliflower mosaic virus 35S promoter or the developmentally specific promoter is a seed-specific promoter.

13. The method of claim 9, wherein the plant is a crop plant.

14. The method of claim 13, wherein the crop plant is soybean.

15. The method of claim 9, wherein the plant is a monocot.

16. The method of claim 9, wherein the plant is a dicot.

17. The method of claim 1, wherein the virus is spread by a plasmodiophorid, a mite, or a nematode.

18. The method of claim 9, wherein the virus is spread by a plasmodiophorid, a mite, or a nematode.

* * * * *